(12) United States Patent
Straubinger et al.

(10) Patent No.: US 8,468,667 B2
(45) Date of Patent: Jun. 25, 2013

(54) DEVICE FOR COMPRESSING A STENT

(75) Inventors: Helmut Straubinger, Aschheim (DE); Johannes Jung, Pforzheim (DE); Arnulf Mayer, Markt Schwaben (DE); Michael J. Girard, Lino Lakes, MN (US); Randy Lane, Langley (CA); Amir Miller, Richmond (CA)

(73) Assignee: JenaValve Technology, Inc., Wilmington, DE (US)

( * ) Notice: Subject to any disclaimer, the term of this patent is extended or adjusted under 35 U.S.C. 154(b) by 455 days.

(21) Appl. No.: 12/778,625

(22) Filed: May 12, 2010

(65) Prior Publication Data
US 2010/0292780 A1 Nov. 18, 2010

Related U.S. Application Data

(60) Provisional application No. 61/178,701, filed on May 15, 2009.

(51) Int. Cl.
*B21D 39/04* (2006.01)

(52) U.S. Cl.
USPC ................................. 29/237; 29/263; 29/280

(58) Field of Classification Search
USPC .................. 29/237, 238, 270, 278, 263, 280; 600/407–408; 604/104–109; 606/108, 200, 606/205–208; 623/1.11, 1.12, 1.23; 72/402
See application file for complete search history.

(56) References Cited

U.S. PATENT DOCUMENTS

| | | | | |
|---|---|---|---|---|
| 388,776 A | * | 8/1888 | Hall | 294/22 |
| 944,214 A | * | 12/1909 | Rydquist | 294/22 |
| 4,922,905 A | | 5/1990 | Strecker | |
| 5,002,566 A | | 3/1991 | Carpentier et al. | |
| 5,061,277 A | | 10/1991 | Carpentier et al. | |
| 5,094,661 A | | 3/1992 | Levy et al. | |
| 5,104,407 A | | 4/1992 | Lam et al. | |
| 5,197,979 A | | 3/1993 | Quintero et al. | |
| 5,279,612 A | | 1/1994 | Eberhardt | |

(Continued)

FOREIGN PATENT DOCUMENTS

| | | |
|---|---|---|
| AU | 2006308187 A1 | 5/2007 |
| AU | 2006310681 A1 | 5/2007 |

(Continued)

OTHER PUBLICATIONS

Aortenklappenbioprothese erfolgreich in der Entwicklung, May 16, 2003 (1 page).

(Continued)

*Primary Examiner* — Brian Glessner
*Assistant Examiner* — Beth Stephan
(74) *Attorney, Agent, or Firm* — Bookoff McAndrews, PLLC

(57) ABSTRACT

The present disclosure relates to a device for compressing a stent or a stent with a prosthetic heart valve affixed thereto, as well as a method for loading a stent into a medical delivery system. The device may comprise a compressing mechanism designed so as to exert a compressive force in radial direction on at least parts of a stent accommodated within the compressing mechanism such that the cross-section of the stent is reduced to a predefinable value at least at certain areas. The device may further comprise a manipulating mechanism moveable relative to the compressing mechanism for moving at least one clamping means in the radial direction in order to adjust the internal cross-sectional diameter of the compressing mechanism.

20 Claims, 49 Drawing Sheets

U.S. PATENT DOCUMENTS

| | | | |
|---|---|---|---|
| 5,332,402 A | 7/1994 | Teitelbaum | |
| 5,336,258 A | 8/1994 | Quintero et al. | |
| 5,352,240 A | 10/1994 | Ross | |
| 5,368,608 A | 11/1994 | Levy et al. | |
| 5,380,054 A * | 1/1995 | Galvis | 294/1.4 |
| 5,411,552 A | 5/1995 | Andersen et al. | |
| 5,456,713 A | 10/1995 | Chuter | |
| 5,509,930 A | 4/1996 | Love | |
| 5,549,666 A | 8/1996 | Hata et al. | |
| 5,595,571 A | 1/1997 | Jaffe et al. | |
| 5,613,982 A | 3/1997 | Goldstein | |
| 5,632,778 A | 5/1997 | Goldstein | |
| 5,674,298 A | 10/1997 | Levy et al. | |
| 5,679,112 A | 10/1997 | Levy et al. | |
| 5,683,451 A | 11/1997 | Lenker et al. | |
| 5,697,972 A | 12/1997 | Kim et al. | |
| 5,713,953 A | 2/1998 | Vallana et al. | |
| 5,746,775 A | 5/1998 | Levy et al. | |
| 5,755,777 A | 5/1998 | Chuter | |
| 5,824,041 A | 10/1998 | Lenker et al. | |
| 5,824,080 A | 10/1998 | Lamuraglia | |
| 5,840,081 A | 11/1998 | Andersen et al. | |
| 5,841,382 A | 11/1998 | Walden et al. | |
| 5,843,181 A | 12/1998 | Jaffe et al. | |
| 5,876,434 A | 3/1999 | Flomenblit et al. | |
| 5,880,242 A | 3/1999 | Hu et al. | |
| 5,899,936 A | 5/1999 | Goldstein | |
| 5,911,752 A * | 6/1999 | Dustrude et al. | 623/1.1 |
| 5,928,281 A | 7/1999 | Huynh et al. | |
| 5,935,163 A | 8/1999 | Gabbay | |
| B15,104,407 I5 | 9/1999 | Lam et al. | |
| 6,001,126 A | 12/1999 | Nguyen-Thien-Nhon | |
| B15,061,277 I5 | 2/2000 | Carpentier et al. | |
| 6,077,297 A | 6/2000 | Robinson et al. | |
| 6,093,530 A | 7/2000 | McIlroy et al. | |
| 6,102,944 A | 8/2000 | Huynh et al. | |
| 6,117,169 A | 9/2000 | Moe | |
| 6,126,685 A | 10/2000 | Lenker et al. | |
| 6,167,605 B1 * | 1/2001 | Morales | 29/282 |
| 6,168,614 B1 | 1/2001 | Andersen et al. | |
| 6,177,514 B1 | 1/2001 | Pathak et al. | |
| 6,183,481 B1 | 2/2001 | Lee et al. | |
| 6,200,336 B1 | 3/2001 | Pavcnik et al. | |
| 6,214,055 B1 | 4/2001 | Simionescu et al. | |
| 6,231,602 B1 | 5/2001 | Carpentier et al. | |
| 6,254,564 B1 | 7/2001 | Wilk et al. | |
| 6,254,636 B1 | 7/2001 | Peredo | |
| 6,257,634 B1 * | 7/2001 | Wei | 294/111 |
| 6,283,995 B1 | 9/2001 | Moe et al. | |
| 6,287,338 B1 | 9/2001 | Sarnowski et al. | |
| 6,338,740 B1 | 1/2002 | Carpentier | |
| 6,342,070 B1 | 1/2002 | Nguyen-Thien-Nhon | |
| 6,344,044 B1 | 2/2002 | Fulkerson et al. | |
| 6,350,278 B1 | 2/2002 | Lenker et al. | |
| 6,379,740 B1 | 4/2002 | Rinaldi et al. | |
| 6,391,538 B1 | 5/2002 | Vyavahare et al. | |
| 6,425,916 B1 | 7/2002 | Garrison et al. | |
| 6,454,799 B1 | 9/2002 | Schreck | |
| 6,471,723 B1 | 10/2002 | Ashworth et al. | |
| 6,478,819 B2 | 11/2002 | Moe | |
| 6,508,496 B1 * | 1/2003 | Huang | 294/115 |
| 6,508,833 B2 | 1/2003 | Pavcnik et al. | |
| 6,509,145 B1 | 1/2003 | Torrianni | |
| 6,521,179 B1 | 2/2003 | Girardot et al. | |
| 6,540,782 B1 | 4/2003 | Snyders | |
| 6,558,417 B2 | 5/2003 | Peredo | |
| 6,558,418 B2 | 5/2003 | Carpentier et al. | |
| 6,572,642 B2 | 6/2003 | Rinaldi et al. | |
| 6,582,462 B1 | 6/2003 | Andersen et al. | |
| 6,585,766 B1 | 7/2003 | Huynh et al. | |
| 6,613,086 B1 | 9/2003 | Moe et al. | |
| 6,682,559 B2 | 1/2004 | Myers et al. | |
| 6,730,118 B2 | 5/2004 | Spenser et al. | |
| 6,736,845 B2 | 5/2004 | Marquez et al. | |
| 6,767,362 B2 | 7/2004 | Schreck | |
| 6,790,230 B2 | 9/2004 | Beyersdorf et al. | |
| 6,808,529 B2 | 10/2004 | Fulkerson | |
| 6,821,211 B2 | 11/2004 | Otten et al. | |
| 6,821,297 B2 | 11/2004 | Snyders | |
| 6,824,970 B2 | 11/2004 | Vyavahare et al. | |
| 6,830,584 B1 | 12/2004 | Seguin | |
| 6,861,211 B2 | 3/2005 | Levy et al. | |
| 6,872,226 B2 | 3/2005 | Cali et al. | |
| 6,881,199 B2 | 4/2005 | Wilk et al. | |
| 6,893,460 B2 | 5/2005 | Spenser et al. | |
| 6,908,481 B2 | 6/2005 | Cribier | |
| 6,911,043 B2 | 6/2005 | Myers et al. | |
| 6,920,674 B2 * | 7/2005 | Thornton | 29/270 |
| 6,926,732 B2 * | 8/2005 | Derus et al. | 623/1.12 |
| 6,945,997 B2 | 9/2005 | Huynh et al. | |
| 6,974,474 B2 | 12/2005 | Pavcnik et al. | |
| 7,014,655 B2 | 3/2006 | Barbarash et al. | |
| 7,018,406 B2 | 3/2006 | Seguin et al. | |
| 7,037,333 B2 | 5/2006 | Myers et al. | |
| 7,050,276 B2 | 5/2006 | Nishiyama | |
| 7,078,163 B2 | 7/2006 | Torrianni | |
| 7,081,132 B2 | 7/2006 | Cook et al. | |
| 7,137,184 B2 | 11/2006 | Schreck et al. | |
| 7,141,064 B2 | 11/2006 | Scott et al. | |
| 7,163,556 B2 | 1/2007 | Xie et al. | |
| 7,189,259 B2 | 3/2007 | Simionescu et al. | |
| 7,198,646 B2 | 4/2007 | Figulla et al. | |
| 7,201,772 B2 | 4/2007 | Schwammenthal et al. | |
| 7,238,200 B2 | 7/2007 | Lee et al. | |
| 7,252,682 B2 | 8/2007 | Seguin | |
| 7,318,278 B2 | 1/2008 | Zhang et al. | |
| 7,318,998 B2 | 1/2008 | Goldstein et al. | |
| 7,322,932 B2 | 1/2008 | Xie et al. | |
| 7,329,278 B2 | 2/2008 | Seguin et al. | |
| 7,381,218 B2 | 6/2008 | Schreck | |
| 7,393,360 B2 | 7/2008 | Spenser et al. | |
| 7,399,315 B2 | 7/2008 | Iobbi | |
| 7,452,371 B2 | 11/2008 | Pavcnik et al. | |
| 7,473,275 B2 | 1/2009 | Marquez | |
| 7,743,481 B2 * | 6/2010 | Lafont et al. | 29/516 |
| 7,896,915 B2 | 3/2011 | Guyenot et al. | |
| 7,914,575 B2 | 3/2011 | Guyenot et al. | |
| 2001/0011187 A1 | 8/2001 | Pavcnik et al. | |
| 2001/0039450 A1 | 11/2001 | Pavcnik et al. | |
| 2002/0032481 A1 | 3/2002 | Gabbay | |
| 2002/0055775 A1 | 5/2002 | Carpentier et al. | |
| 2002/0123790 A1 | 9/2002 | White et al. | |
| 2002/0133226 A1 | 9/2002 | Marquez et al. | |
| 2002/0193871 A1 | 12/2002 | Beyersdorf et al. | |
| 2002/0198594 A1 | 12/2002 | Schreck | |
| 2003/0027332 A1 | 2/2003 | Lafrance et al. | |
| 2003/0036791 A1 | 2/2003 | Philipp et al. | |
| 2003/0036795 A1 | 2/2003 | Andersen et al. | |
| 2003/0040792 A1 | 2/2003 | Gabbay | |
| 2003/0050694 A1 | 3/2003 | Yang et al. | |
| 2003/0055495 A1 | 3/2003 | Pease et al. | |
| 2003/0065386 A1 | 4/2003 | Weadock | |
| 2003/0114913 A1 | 6/2003 | Spenser et al. | |
| 2003/0125795 A1 | 7/2003 | Pavcnik et al. | |
| 2003/0139796 A1 | 7/2003 | Sequin et al. | |
| 2003/0139803 A1 | 7/2003 | Sequin et al. | |
| 2003/0149476 A1 | 8/2003 | Damm et al. | |
| 2003/0149478 A1 | 8/2003 | Figulla et al. | |
| 2003/0153974 A1 | 8/2003 | Spenser et al. | |
| 2003/0195620 A1 | 10/2003 | Huynh et al. | |
| 2003/0236570 A1 | 12/2003 | Cook et al. | |
| 2004/0006380 A1 | 1/2004 | Buck et al. | |
| 2004/0039436 A1 | 2/2004 | Spenser et al. | |
| 2004/0049262 A1 | 3/2004 | Obermiller et al. | |
| 2004/0073289 A1 | 4/2004 | Hartley et al. | |
| 2004/0078950 A1 | 4/2004 | Schreck et al. | |
| 2004/0117004 A1 | 6/2004 | Osborne et al. | |
| 2004/0117009 A1 | 6/2004 | Cali et al. | |
| 2004/0148018 A1 | 7/2004 | Carpentier et al. | |
| 2004/0153145 A1 | 8/2004 | Simionescu et al. | |
| 2004/0186558 A1 | 9/2004 | Pavcnik et al. | |
| 2004/0186563 A1 | 9/2004 | Lobbi | |
| 2004/0186565 A1 | 9/2004 | Schreck | |
| 2004/0193244 A1 | 9/2004 | Hartley et al. | |
| 2004/0210301 A1 | 10/2004 | Obermiller et al. | |
| 2004/0210304 A1 | 10/2004 | Seguin et al. | |
| 2004/0260389 A1 | 12/2004 | Case et al. | |

| | | |
|---|---|---|
| 2005/0009000 A1 | 1/2005 | Wilhelm et al. |
| 2005/0033220 A1 | 2/2005 | Wilk et al. |
| 2005/0033398 A1 | 2/2005 | Seguin |
| 2005/0043790 A1 | 2/2005 | Seguin |
| 2005/0049692 A1 | 3/2005 | Numamoto et al. |
| 2005/0075725 A1 | 4/2005 | Rowe |
| 2005/0075776 A1 | 4/2005 | Cho |
| 2005/0085890 A1* | 4/2005 | Rasmussen et al. ......... 623/1.11 |
| 2005/0096726 A1 | 5/2005 | Sequin et al. |
| 2005/0096735 A1 | 5/2005 | Hojeibane et al. |
| 2005/0096736 A1 | 5/2005 | Osse et al. |
| 2005/0098547 A1 | 5/2005 | Cali et al. |
| 2005/0113910 A1 | 5/2005 | Paniagua et al. |
| 2005/0119728 A1 | 6/2005 | Sarac |
| 2005/0119736 A1 | 6/2005 | Zilla et al. |
| 2005/0137687 A1 | 6/2005 | Salahieh et al. |
| 2005/0137688 A1 | 6/2005 | Salahieh et al. |
| 2005/0137690 A1 | 6/2005 | Salahieh et al. |
| 2005/0137697 A1 | 6/2005 | Salahieh et al. |
| 2005/0137698 A1 | 6/2005 | Salahieh et al. |
| 2005/0137702 A1 | 6/2005 | Haug et al. |
| 2005/0143804 A1 | 6/2005 | Haverkost |
| 2005/0143807 A1 | 6/2005 | Pavcnik et al. |
| 2005/0149166 A1 | 7/2005 | Schaeffer et al. |
| 2005/0150775 A1 | 7/2005 | Zhang et al. |
| 2005/0171597 A1 | 8/2005 | Boatman et al. |
| 2005/0171598 A1 | 8/2005 | Schaeffer |
| 2005/0192665 A1 | 9/2005 | Spenser et al. |
| 2005/0197695 A1 | 9/2005 | Stacchino et al. |
| 2005/0222668 A1 | 10/2005 | Schaeffer et al. |
| 2005/0234546 A1 | 10/2005 | Nugent et al. |
| 2005/0267560 A1 | 12/2005 | Bates |
| 2006/0009842 A1 | 1/2006 | Huynh et al. |
| 2006/0025857 A1 | 2/2006 | Bergheim et al. |
| 2006/0047343 A1 | 3/2006 | Oviatt et al. |
| 2006/0058864 A1 | 3/2006 | Schaeffer et al. |
| 2006/0074484 A1 | 4/2006 | Huber |
| 2006/0111770 A1 | 5/2006 | Pavcnik et al. |
| 2006/0142846 A1 | 6/2006 | Pavcnik et al. |
| 2006/0149360 A1 | 7/2006 | Schwammenthal et al. |
| 2006/0155366 A1 | 7/2006 | LaDuca et al. |
| 2006/0167543 A1 | 7/2006 | Bailey et al. |
| 2006/0178740 A1 | 8/2006 | Stacchino et al. |
| 2006/0193885 A1 | 8/2006 | Neethling et al. |
| 2006/0210597 A1 | 9/2006 | Hiles |
| 2006/0224183 A1 | 10/2006 | Freudenthal |
| 2006/0229718 A1 | 10/2006 | Marquez |
| 2006/0229719 A1 | 10/2006 | Marquez et al. |
| 2006/0246584 A1 | 11/2006 | Covelli |
| 2006/0259134 A1 | 11/2006 | Schwammenthal et al. |
| 2006/0259136 A1 | 11/2006 | Nguyen et al. |
| 2006/0259137 A1 | 11/2006 | Artof et al. |
| 2006/0265056 A1 | 11/2006 | Nguyen et al. |
| 2006/0287717 A1 | 12/2006 | Rowe et al. |
| 2006/0287719 A1 | 12/2006 | Rowe et al. |
| 2006/0290027 A1 | 12/2006 | O'Connor et al. |
| 2006/0293745 A1 | 12/2006 | Carpentier et al. |
| 2007/0005129 A1 | 1/2007 | Damm et al. |
| 2007/0005131 A1 | 1/2007 | Taylor |
| 2007/0005132 A1 | 1/2007 | Simionescu et al. |
| 2007/0020248 A1 | 1/2007 | Everaerts et al. |
| 2007/0021826 A1 | 1/2007 | Case et al. |
| 2007/0027535 A1 | 2/2007 | Purdy, Jr. et al. |
| 2007/0038291 A1 | 2/2007 | Case et al. |
| 2007/0038295 A1 | 2/2007 | Case et al. |
| 2007/0043435 A1 | 2/2007 | Seguin et al. |
| 2007/0050014 A1 | 3/2007 | Johnson |
| 2007/0088431 A1 | 4/2007 | Bourang et al. |
| 2007/0093887 A1 | 4/2007 | Case et al. |
| 2007/0100435 A1 | 5/2007 | Case et al. |
| 2007/0100440 A1 | 5/2007 | Figulla et al. |
| 2007/0112422 A1 | 5/2007 | Dehdashtian |
| 2007/0123700 A1 | 5/2007 | Ueda et al. |
| 2007/0123979 A1 | 5/2007 | Perier et al. |
| 2007/0142906 A1 | 6/2007 | Figulla et al. |
| 2007/0162103 A1 | 7/2007 | Case et al. |
| 2007/0173932 A1 | 7/2007 | Cali et al. |
| 2007/0179592 A1 | 8/2007 | Schaeffer |
| 2007/0185565 A1 | 8/2007 | Schwammenthal et al. |
| 2007/0203576 A1 | 8/2007 | Lee et al. |
| 2007/0213813 A1 | 9/2007 | Von Segesser et al. |
| 2007/0239271 A1 | 10/2007 | Nguyen |
| 2007/0244551 A1 | 10/2007 | Stobie |
| 2007/0260327 A1 | 11/2007 | Case et al. |
| 2007/0288087 A1 | 12/2007 | Fearnot et al. |
| 2008/0004688 A1 | 1/2008 | Spenser et al. |
| 2008/0021546 A1 | 1/2008 | Patz et al. |
| 2008/0033534 A1 | 2/2008 | Cook et al. |
| 2008/0065011 A1 | 3/2008 | Marchand et al. |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0071369 A1 | 3/2008 | Tuval et al. |
| 2008/0077236 A1 | 3/2008 | Letac et al. |
| 2008/0086205 A1 | 4/2008 | Gordy et al. |
| 2008/0097586 A1 | 4/2008 | Pavcnik et al. |
| 2008/0102439 A1 | 5/2008 | Tian et al. |
| 2008/0133003 A1 | 6/2008 | Seguin et al. |
| 2008/0140189 A1 | 6/2008 | Nguyen et al. |
| 2008/0154355 A1 | 6/2008 | Benichou et al. |
| 2008/0200977 A1 | 8/2008 | Paul et al. |
| 2008/0215143 A1 | 9/2008 | Seguin |
| 2008/0255661 A1 | 10/2008 | Straubinger et al. |
| 2008/0262602 A1 | 10/2008 | Wilk et al. |
| 2008/0269878 A1 | 10/2008 | Iobbi |
| 2008/0275549 A1 | 11/2008 | Rowe |
| 2009/0054976 A1* | 2/2009 | Tuval et al. .................. 623/2.11 |
| 2009/0222076 A1 | 9/2009 | Figulla et al. |
| 2009/0287290 A1* | 11/2009 | Macaulay et al. ........... 623/1.11 |
| 2010/0249915 A1 | 9/2010 | Zhang |
| 2010/0249916 A1 | 9/2010 | Zhang |
| 2010/0249917 A1 | 9/2010 | Zhang |
| 2010/0249918 A1 | 9/2010 | Zhang |

FOREIGN PATENT DOCUMENTS

| | | |
|---|---|---|
| CA | 2436258 A1 | 1/2005 |
| CA | 2595233 A1 | 7/2006 |
| CA | 2627555 A1 | 5/2007 |
| DE | 19546692 A1 | 6/1997 |
| DE | 20003874 U1 | 6/2000 |
| DE | 19857887 A1 | 7/2000 |
| DE | 10010073 A1 | 9/2001 |
| DE | 10010074 A1 | 10/2001 |
| DE | 101 21 210 A1 | 11/2002 |
| DE | 19546692 C2 | 11/2002 |
| DE | 10301026 A1 | 2/2004 |
| DE | 10335948 B3 | 7/2004 |
| DE | 10302447 A1 | 2/2005 |
| DE | 10010074 B4 | 4/2005 |
| DE | 19857887 B4 | 5/2005 |
| DE | 10010073 B4 | 12/2005 |
| DE | 10 2005 051 849 | 5/2007 |
| DE | 10 2005 052628 A1 | 5/2007 |
| DE | 202007005491 U1 | 7/2007 |
| EP | 0084395 A1 | 7/1983 |
| EP | 0402036 B1 | 12/1990 |
| EP | 0402176 B1 | 12/1990 |
| EP | 0458877 B1 | 4/1991 |
| EP | 0515324 A1 | 11/1992 |
| EP | 0547135 B1 | 6/1993 |
| EP | 0 592 410 B1 | 11/1995 |
| EP | 0729364 B1 | 9/1996 |
| EP | 0756498 B1 | 5/1997 |
| EP | 0778775 B1 | 6/1997 |
| EP | 0928615 A1 | 7/1999 |
| EP | 0986348 B1 | 3/2000 |
| EP | 1041942 B1 | 10/2000 |
| EP | 1041943 B1 | 10/2000 |
| EP | 1117446 B1 | 7/2001 |
| EP | 1251804 B1 | 10/2002 |
| EP | 0 971 649 B1 | 12/2002 |
| EP | 1281357 A2 | 2/2003 |
| EP | 1281375 A2 | 2/2003 |
| EP | 1 017 868 B1 | 9/2003 |
| EP | 1354569 A1 | 10/2003 |
| EP | 1 519 697 A0 | 1/2004 |

| | | | |
|---|---|---|---|
| EP | 1452153 A1 | 9/2004 |
| EP | 0987998 B1 | 10/2004 |
| EP | 1 087 727 B1 | 11/2004 |
| EP | 1 233 731 B1 | 12/2004 |
| EP | 1499366 B1 | 1/2005 |
| EP | 1 253 875 B1 | 4/2005 |
| EP | 1 251 803 B1 | 6/2005 |
| EP | 1469797 B1 | 11/2005 |
| EP | 1 690 515 A1 | 8/2006 |
| EP | 1 251 805 B1 | 3/2007 |
| EP | 1 255 510 B1 | 3/2007 |
| EP | 1112042 B1 | 11/2007 |
| EP | 1878407 A1 | 1/2008 |
| EP | 1886649 A2 | 2/2008 |
| EP | 1 900 343 A2 | 3/2008 |
| EP | 1259195 B1 | 10/2008 |
| EP | 1980220 A1 * | 10/2008 |
| EP | 1994913 A2 | 11/2008 |
| EP | 2 000 115 A2 | 12/2008 |
| FR | 2828263 A1 | 2/2003 |
| GB | 2433700 A | 7/2007 |
| GB | 2440809 A | 2/2008 |
| JP | 2003-523262 | 8/2003 |
| JP | 2003-524504 | 8/2003 |
| JP | 2005-118585 | 5/2005 |
| JP | 2007-296375 | 11/2007 |
| WO | WO-90/09102 | 8/1990 |
| WO | WO 95/11055 A1 | 4/1995 |
| WO | WO-95/24873 | 9/1995 |
| WO | WO-95/28183 | 10/1995 |
| WO | WO-96/13227 | 5/1996 |
| WO | WO-97/32615 | 9/1997 |
| WO | WO-98/43556 | 10/1998 |
| WO | WO-98/46165 | 10/1998 |
| WO | WO-99/37337 | 7/1999 |
| WO | WO-99/66863 | 12/1999 |
| WO | WO 00/15148 | 3/2000 |
| WO | WO-00/18445 | 4/2000 |
| WO | WO 00/25702 A1 | 5/2000 |
| WO | WO 00/47139 A1 | 8/2000 |
| WO | WO-00/53125 | 9/2000 |
| WO | WO-00/62714 | 10/2000 |
| WO | WO-01/10209 A1 | 2/2001 |
| WO | WO 01/35870 A1 | 5/2001 |
| WO | WO-01/41679 A1 | 6/2001 |
| WO | WO-01/51104 A1 | 7/2001 |
| WO | WO 01/54625 A1 | 8/2001 |
| WO | WO 01/58503 A1 | 8/2001 |
| WO | WO 01/62189 A1 | 8/2001 |
| WO | WO 01/64137 A1 | 9/2001 |
| WO | WO 02/36048 A1 | 5/2002 |
| WO | WO-02/058745 A1 | 8/2002 |
| WO | WO-02/100301 A1 | 12/2002 |
| WO | WO-02/102286 A1 | 12/2002 |
| WO | WO 03/003949 A2 | 1/2003 |
| WO | WO-03/007795 A2 | 1/2003 |
| WO | WO-03/009785 A1 | 2/2003 |
| WO | WO 03/011195 A2 | 2/2003 |
| WO | WO 03/013239 | 2/2003 |
| WO | WO 03/028592 A1 | 4/2003 |
| WO | WO 03/047468 A1 | 6/2003 |
| WO | WO-03/079928 A2 | 10/2003 |
| WO | WO 03/096935 A1 | 11/2003 |
| WO | WO 2004/004597 A2 | 1/2004 |
| WO | WO 2004/016200 A1 | 2/2004 |
| WO | WO 2004/016201 A2 | 2/2004 |
| WO | WO 2004/019825 A1 | 3/2004 |
| WO | WO-2004/026117 A2 | 4/2004 |
| WO | WO 2004/026173 A2 | 4/2004 |
| WO | WO 2004/028399 A2 | 4/2004 |
| WO | WO 2004/043301 A1 | 5/2004 |
| WO | WO 2004/082527 A2 | 9/2004 |
| WO | WO 2004/082528 A2 | 9/2004 |
| WO | WO 2004/096100 A1 | 11/2004 |
| WO | WO 2005/021063 A2 | 3/2005 |
| WO | WO 2005/034812 A1 | 4/2005 |
| WO | WO 2005/062980 A2 | 7/2005 |
| WO | WO-2005/072654 A1 | 8/2005 |
| WO | WO-2006/066327 A1 | 6/2006 |
| WO | WO 2006/076890 A1 | 7/2006 |
| WO | WO-2006/102063 A2 | 9/2006 |
| WO | WO 2006/108090 A2 | 10/2006 |
| WO | WO 2006/124649 A2 | 11/2006 |
| WO | WO-2006/124649 A2 | 11/2006 |
| WO | WO 2006/127756 A2 | 11/2006 |
| WO | WO 2006/127765 A1 | 11/2006 |
| WO | WO-2006/132948 A1 | 12/2006 |
| WO | WO 2007/047488 A2 | 4/2007 |
| WO | WO 2007/047945 A2 | 4/2007 |
| WO | WO2007/048529 A1 | 5/2007 |
| WO | WO 2007/051620 A1 | 5/2007 |
| WO | WO 2007/059252 A1 | 5/2007 |
| WO | WO-2007/071436 A2 | 6/2007 |
| WO | WO 2007/098232 A2 | 8/2007 |
| WO | WO 2007/120543 A1 | 10/2007 |
| WO | WO-2008/028569 A1 | 3/2008 |
| WO | WO 2008/035337 A | 3/2008 |
| WO | WO 2008/045949 | 4/2008 |
| WO | WO 2008/070797 A2 | 6/2008 |
| WO | WO 2008/079962 A1 | 7/2008 |
| WO | WO 2008/101083 A2 | 8/2008 |
| WO | WO 2008/125153 A1 | 10/2008 |
| WO | WO 2008/138584 A1 | 11/2008 |
| WO | WO 2008/150529 A | 12/2008 |

OTHER PUBLICATIONS

Screen shots from http://www.fraunhofer.de/presse/filme/2006/index.jsp, 2006 (2 pages).
Liang, Ma, et al., "Double-crowned valved stents for off-pump mitral valve replacement," *Eu. J. Cardio-Thoracic Surgery*, vol. 28, pp. 194-198 (2005) (5 pages).
Huber, Christoph H., et al. "Direct Access Valve Replacement (DAVR)—are we entering a new era in cardiac surgery?" *Eur. J. Cardio-Thoracic Surgery*, vol. 29, pp. 380-385 (2006) (6 pages).
English translation of DE 19546692 A1 (3 pages), Jun. 19, 1997.
English translation of EP 1469797 B1 (15 pages), Nov. 2, 2005.
File history for German Patent DE 195 46 692 filed Dec. 14, 1995 and patented Jul. 11, 2002 (111 pages).
English abstract for DE 19857887 A1 (1 page). Jul. 6, 2000.
English abstract for DE 10335948 B3 (1 page), Jul. 29, 2004.
Klein, Allan L. et al., "Age-related Prevalence of Valvular Regurgitation in Normal Subjects: A Comprehensive Color Flow Examination of 118 Volunteers," *J. Am. Soc. Echocardiography*, vol. 3, No. 1, pp. 54-63 (1990) (10 pages).
Gummert, J.F. et al., "Cardiac Surgery in Germany During 2007: A Report on Behalf of the German Society for Thoracic and Cardiovascular Surgery," *Thorac. Cardiov, Surg.*, vol. 56, pp. 328-336 (2008) (9 pages).
Gummert, J.F. et al., "Cardiac Surgery in Germany During 2006: A Report on Behalf of the German Society for Thoracic and Cardiovascular Surgery," *Thorac. Cardiov. Surg.*, vol. 55, pp. 343-350 (2007) (8 pages).

* cited by examiner

DEVICE FOR COMPRESSING A STENT

CROSS-REFERENCE TO RELATED APPLICATIONS

This application claims priority to U.S. Provisional Patent Application No. 61/178,701, filed May 15, 2009, the entire contents of which are hereby incorporated herein by reference.

The present disclosure relates to a device for compressing a stent, as needed with a prosthetic heart valve affixed thereto, as well as a system for loading a stent, as needed with a prosthetic heart valve affixed thereto, into a medical delivery system, in particular the tip of a catheter of a medical delivery system. The disclosure further relates to a method for loading a stent, as needed with a prosthetic heart valve affixed thereto, into a medical delivery system, in particular the tip of a catheter of a medical delivery system.

BACKGROUND OF THE INVENTION

Medical technology has long since endeavored to correct valvular defects such as, for example, aortic valve insufficiencies or aortic valve stenosis, by means of non-surgical, transarterial access; i.e. without requiring open heart surgery, with implantation by way of catheter. In the process, various different stent systems with various different advantages and disadvantages have been proposed, some which can also be inserted transarterially into the body of a patient via a catheter delivery system.

The terms "aortic valve stenosis and/or aortic valve insufficiency" as used herein generally refer to a congenital or acquired dysfunction of one or more cardiac valves. Such valvular disorders can affect any of the four cardiac valves, whereby the valves in the left ventricle or left chamber (aortic and mitral valve) are typically more affected than those on the right side of the heart (pulmonary and tricuspid valve). The dysfunction can be a constriction (stenosis), an incompetence (insufficiency) or a combination of the two (combined vitium).

Minimally invasive forms of treatment have recently been developed which are in particular characterized by allowing the procedure to be performed under local anesthesia. One approach provides for using a catheter system to implant an expandable stent, to which a collapsible prosthetic heart valve has been affixed, into a human body. Such an expandable prosthetic heart valve can be guided via a delivery or catheter system to the implantation site within the heart through an inguinal artery or vein. After reaching the implantation site, the stent can then be unfolded. After unfolding, the prosthetic heart valve can be anchored in the respective blood vessel at least in an area close to the heart, for example with the aid of anchoring hooks. The actual prosthetic heart valve is usually positioned in the proximal area of the stent.

For example, the WO 2004/019825 A1 printed publication describes a heart valve stent for a heart valve prosthesis. This stent can be introduced into the site of implantation in the patient's heart via a medical delivery system to treat an aortic valve stenosis and/or aortic valve insufficiency in a minimally invasive manner.

Known conventional systems for implanting a prosthetic heart valve introduce an expandable stent system transarterially/transfemorally or transapically into the body of the patient using a medical delivery system. This type of stent system consists for example of an expandable anchoring support (hereinafter also referred to as "cardiac valve stent" or simply "stent"), to which the actual prosthetic heart valve is affixed or can be affixed, preferably at the end region nearest the heart (proximal end).

The explanations disclosed herein with respect to a "stent system" are also applicable to a "stent".

The term "medical delivery system" as used herein generally refers to a medical system with which a stent system can be advanced in minimally invasive fashion to the site of implantation in the patient's heart, for example to treat an aortic valve stenosis and/or aortic valve insufficiency. In the present context, "minimally invasive" means a heart-lung machine is not needed when performing the procedure on the anaesthetized patient such that not only can the medical procedure be performed at reasonable cost, but there is also less physical and psychological strain on the patient.

A medical delivery system usually comprises a catheter system by means of which a stent, as needed with a prosthetic heart valve affixed thereto in folded state, can be introduced into the patient's body in its folded state. For example, the medical delivery system can exhibit a catheter tip having at least one manipulatable receiving area at a proximal end section of the catheter system; i.e. closest to the heart. It is moreover conceivable for the medical delivery system to exhibit a handle at the distal end section of the catheter system; i.e. at the end section of the catheter system farthest from the heart and the catheter tip, with which the at least one receiving area of the caterer tip can be appropriately manipulated such that the expandable stent accommodated in the catheter tip, as needed with a prosthetic heart valve affixed thereto, can be incrementally released from the catheter tip according to a predefined or predefinable sequence of events.

In this disclosure, the expression "catheter system" means a system that can be inserted into a body cavity, duct or vessel. A catheter system thereby allows access by surgical instruments. The process of inserting a catheter system is catheterisation. In most uses a catheter system is a thin, flexible tube: a "soft" catheter system; in some uses, it is a larger, solid tube: a "hard" catheter system.

To introduce the stent system, the stent together with the prosthetic heart valve affixed as needed thereto, is loaded into the tip of the medical delivery system's catheter. In order to do so, the stent, as needed with the prosthetic heart valve affixed thereto, needs to exhibit a first predefinable shape in which the stent or the stent and the prosthetic heart valve affixed thereto is/are in a compressed or folded state. In its first predefined state, the stent, as needed with the prosthetic heart valve affixed thereto, exhibits a diameter which is essentially determined by the diameter of the catheter tip of the medical delivery system.

For the majority of patients undergoing treatment, it is preferable for the stent, as needed with the prosthetic heart valve affixed thereto, to have an outer diameter of approximately 7.0 mm to approximately 5.0 mm in its first shape so that the stent system can be introduced with a 21F delivery system (given an external diameter of 7.0 mm) or with a 15F delivery system (given an external diameter of 5.0 mm).

After the stent system has been released from the catheter tip, in the implanted state respectively, the stent system exhibits a second predefined shape in which the stent or the stent and the prosthetic heart valve affixed thereto is/are in an expanded state. Depending on the patient being treated, it is preferable for the stent to exhibit a diameter of between 19.0 mm and 27.0 mm in its second shape and implanted state.

Thus, the first shape transitions to the second shape by a cross-sectional widening, wherein the stent stretches radially and presses against the vascular wall of a blood vessel near the heart and thus fixes a prosthetic heart valve affixed as needed to the stent at the site of implantation. The cross-sectional widening can be effected by a balloon system when the stent is implanted with the help of a so called balloon catheter system.

On the other hand, it is also known from medical technology to construct the stent from a superelastic shape memory material which is designed such that the stent can transform from a temporary shape into a permanent shape under the influence of an external stimulus. The temporary shape thereby corresponds to the stent's first shape when the stent, as needed with the prosthetic heart valve affixed thereto, is in its folded state. The permanent shape corresponds to the stent's second shape when in its expanded state. An example of a suitable shape memory material would be nitinol, e.g., an equiatomic alloy of nickel and titanium.

Turning out to be disadvantageous with conventional systems for implanting a prosthetic heart valve as known to date, however, has been that not only the actual implantation of the stent, as needed with the prosthetic heart valve affixed thereto, but also the preparation needed for the implant procedure is relatively complicated, difficult and laborious. Apart from the complicated implanting of the stent, as needed with a prosthetic heart valve affixed thereto, to replace an insufficient native heart valve, for example, there is also the fundamental problem of the stent and/or the stent and a prosthetic heart valve affixed thereto being damaged when the stent, as needed with a prosthetic heart valve affixed thereto, is loaded into the tip of the catheter of the medical delivery system in preparation for the surgery. In particular with self-expanding stent systems, the stent, as needed with a prosthetic heart valve affixed thereto, has to be compressed so that it will then be in its first shape and be able to be introduced into the tip of the catheter of a medical delivery system. This subjects the stent to considerable compressive forces in order to overcome the self-expanding stent structure's expansion forces and achieve the desired reduction in cross-section.

Similar circumstances however also apply to stent systems which are implanted using balloon catheter systems.

In conjunction hereto, often likewise regarded as problematic is that when preparing for the implant procedure, the stent, as needed with a prosthetic heart valve affixed thereto, can often only be loaded into the tip of the catheter of a medical delivery system by an experienced perfusionist or by product specialists so as to avoid damaging the stent system and so that the stent system can be properly transformed into its defined first shape.

Without special compressing mechanisms or loading systems, the known systems are thus coupled with the fundamental risk of damage to the stent system or it not properly being transformed into its defined first shape, for example due to an oversight on the part of the perfusionist or product specialist or some other incident occurring during the compressing of the stent system. Damage which occurs when compressing the stent system or when loading the compressed stent system into the catheter tip of the medical delivery system are often not noted until the actual implant procedure is underway, for example when the positioning and/or fixing of the prosthetic heart valve at the site of implantation at the heart by means of the stent is imprecise, when the stent will not properly expand at the implantation site in the heart, or when it is for example determined that the implanted prosthetic heart valve cannot or not adequately enough assume the function of the native heart valve to be replaced.

BRIEF SUMMARY OF THE INVENTION

On the basis of the problems outlined above, the present disclosure relates to a device as well as a system for compressing a stent with which the stent, as needed with a prosthetic heart valve affixed thereto, can be readily compressed to a desired diameter, in particular without the risk of the stent and/or the stent and a prosthetic heart valve affixed thereto being damaged when compressed.

Embodiments of the present disclosure may provide a simplified method for loading a stent, as needed with a prosthetic heart valve affixed thereto, into the catheter tip of a medical delivery system, in particular wherein the proper loading of the stent into the tip of the catheter no longer depends to a significant extent on the finesse and experience of the given perfusionist or product specialist.

Embodiments of the present disclosure may include a device for compressing a stent, as needed with a prosthetic heart valve affixed thereto, whereby the device comprises a compressing mechanism and a manipulating mechanism. The compressing mechanism is designed such that a stent to be compressed can at least partly be accommodated in the compressing mechanism. The compressing mechanism is adapted to exert a compressive force in radial direction on at least parts of the stent accommodated within the compressing mechanism such that the cross-section of the stent is reduced to a predefinable value at least at certain areas. For this purpose, the compressing mechanism may comprise externally manipulatable clamping means, said clamping means being moveable in the radial direction of the device in order to adjust the internal cross-sectional diameter of the compressing mechanism. For moving the clamping means in the radial direction, the device according to the present invention may comprise a manipulating mechanism. The manipulating mechanism is moveable relative to the compressing mechanism for moving the at least one clamping means in the radial direction in order to adjust the internal cross-sectional diameter of the compressing mechanism.

Embodiments of the present disclosure allows for compressing a stent, as needed with a prosthetic heart valve affixed thereto, to a desired diameter. The term "desired diameter" means a diameter of the stent which allows a proper loading of the stent into the tip of a catheter.

The compressing mechanism is on the one hand configured such that the stent to be compressed can be at least partly accommodated inside the compressing mechanism. On the other hand, the compressing mechanism of the is designed to exert a compressive force radial to the stent at least on certain areas of the outer surface of the stent such that the stent's cross-section is reduced to a predefinable value at least at certain areas.

Although not mandatory, a gripping mechanism may be used for forming a releasable connection with the stent to be compressed, and in particular with an end section of said stent. In case a gripping mechanism comes into operation, it shall be realized separately from the compressing mechanism and axial displaceable to be at least partly accommodated within the compressing mechanism. The gripping mechanism may comprise an actuating element attached to a claw for grasping the stent.

At least one clamping means, for example, an externally actuatable clamping jaw is provided in the interior of the compressing mechanism which is movable in the radial direction to set the internal cross-section diameter of at least one area of the compressing mechanism.

For this purpose, the compressing mechanism may comprise at least one externally manipulatable clamping means. The at least one clamping means is manipulatable by the already mentioned manipulating mechanism. In particular, according to some embodiments of the device, the manipulating mechanism is movable relative to the compressing mechanism in order to move the at least one clamping means in the radial direction to adjust the internal cross-sectional diameter of the compressing mechanism.

In some embodiments of the device, the at least one clamping means of the compressing mechanism may comprise at least one, in particular externally actuatable clamping jaw which is provided in the interior of the comprising mechanism and which is movable in the radial direction to set the internal cross-section diameter of at least one area of the compressing mechanism.

In another embodiment of the present disclosure, the at least one, in particular externally actuatable clamping means may comprise a preferably flat strip which is looped such as to form a clamping noose within which the stent to be compressed can be at least partly accommodated. Again, this preferably flat strip acting as clamping means is provided in the interior of the compressing mechanism and is movable in the radial direction to set the internal cross-section diameter of at least one area of the compressing mechanism.

According to another embodiment of the present disclosure, the device for compressing a stent may comprise a compressing mechanism and a gripping mechanism. The gripping mechanism may be used for forming a releasable connection with a stent to be compressed, and in particular with an end section of said stent. The gripping mechanism is thereby realized separately from the compressing mechanism and is axial displaceable to be at least partly accommodated within the compressing mechanism. The gripping mechanism comprises an actuating element attached to a claw for grasping the stent.

With respect to the specified disclosure, a system is further disclosed with which a stent, as needed with a prosthetic heart valve affixed thereto, can be loaded into a medical delivery system, in particular into the tip of a catheter of a medical delivery system. The system comprises a device for precompressing at least parts of the stent and a supplementary compressing mechanism for further compressing at least parts of the stent. The structure of the supplementary compressing mechanism may be the same or at least similar to the structure of one of the hereafter further described compressing mechanisms.

To solve the cited second task, a method is disclosed to load a stent, as needed with a prosthetic heart valve affixed thereto, into a medical delivery system, in particular into the tip of a catheter of a medical delivery system, whereby the method comprises the method steps as specified in claim 58.

The explanations disclosed herein with respect to a stent are also applicable to a stent with a prosthetic heart valve affixed thereto.

As already mentioned, a gripping mechanism may be used for forming a releasable connection with the stent to be compressed. Providing a gripping mechanism which is designed to create a releasable connection to the stent to be compressed, and in particular to an end section of the stent, may eliminate directly touching the stent by hand when compressing the stent or loading it into the tip of the catheter of the medical delivery system. In this respect, the risk of a contamination and damaging of the stent and/or the stent with the prosthetic heart valve affixed thereto can be avoided or reduced. Instead, to grasp the stent to be compressed, the claw of the gripping mechanism only comes into contact with those areas of the stent to be compressed provided for the purpose such that the risk of damaging the stent during grasping may be significantly reduced or eliminated.

Specifically, the gripping mechanism may comprise a claw, or gripping forceps respectively, with which the stent to be compressed can be grasped, preferably at the end section of said stent. It is thereby preferable for the releasable connection between the claw and the stent to occur preferably at an end section of the stent at which the prosthetic heart valve is not sewn or to be sewn and which serves to connect to a fastening section in the catheter tip of the medical delivery system. This end section of the stent is usually the distal end section of said stent.

The terms "distal" and "proximal" as used herein are positional or directional identifiers for the stent, each referring to the stent in the implanted state. With a heart valve stent used for example to treat aortic or pulmonary valve insufficiency, the proximal end section of the stent thus faces the left or right chamber when the stent is in its implanted state.

The gripping mechanism may further comprise an actuating element by means of which the claw can be manipulated accordingly so as to grasp the stent to be compressed. The gripping mechanism is thus suited to form a releasable connection with the stent to be compressed without the stent thereby needing to be touched by hand.

Since the gripping mechanism is axially displaceable when being received in the compressing mechanism, this ensures that the stent grasped with the claw of the gripping mechanism can be loaded into the compressing mechanism. Specifically, the compressing mechanism is designed such that the stent grasped by the gripping mechanism can be received within the compressing mechanism and can be displaced longitudinally relative the compressing mechanism. It is in this way possible to load a stent releasably connected to the claw of the gripping mechanism into the compressing mechanism such that the stent to be compressed is at least partly accommodated within said compressing mechanism.

The device thus allows the stent to be compressed to be loaded into the compressing mechanism, whereby the gripping mechanism only comes into contact with the areas of the stent so intended for the purpose.

One possible realization of the disclosed device provides for the gripping mechanism to comprise a guide sleeve in which the claw can be at least partly accommodated. In so doing, the claw should be movable relative the guide sleeve upon actuation of the actuating element. This provides an effective solution for realizing interaction of the gripping mechanism's actuating element with the claw in order to create a releasable connection between the gripping mechanism and the stent to be compressed in the compressing mechanism. Other embodiments of the gripping mechanism are also conceivable.

In order to have the gripping mechanism be accommodated at least partly within the compressing mechanism in defined manner, it is preferable for the guide sleeve to comprise at least one guiding element configured complementary to at least one of the guiding elements allocated to the compressing mechanism. For example, it is conceivable for at least one guiding element designated for the guide sleeve to be configured as a guide rail extending longitudinally to the guide sleeve.

The at least one guiding element allocated to the compressing mechanism may be configured as a guiding groove designed correspondingly complementary to the guide rail. The gripping mechanism accommodated in the compressing mechanism can thus be aligned relative to the compressing mechanism by the guiding element allocated to the guide sleeve on the one hand and the compressing mechanism on the other. The guiding elements extend preferably in the longitudinal direction to the guide sleeve, the compressing mechanism respectively, so that same allow a longitudinal movement of the gripping mechanism relative the compressing mechanism and thereby guide the gripping mechanism.

It is also conceivable for at least one guiding element allocated to the guide sleeve to be configured as a guiding groove and at least one guiding element allocated to the compressing mechanism to be configured as a guide rail. Other embodiments of the guiding elements designated for the guide sleeve, the compressing mechanism respectively, are likewise conceivable and covered by the present disclosure.

One possible realization of the gripping mechanism provides for the gripping mechanism to comprise a retaining section arranged coaxially to the guide sleeve and connected to said guide sleeve. The retaining section preferably serves to receive the actuating element with which the claw of the gripping mechanism can be correspondingly manipulated. It is for example conceivable for the actuating element to comprise a preferably manually actuatable pushbutton held in the retaining section and movable in the longitudinal direction of the gripping mechanism relative the retaining section and relative the guide sleeve.

The pushbutton can, for example, be connected to the claw of the gripping mechanism so that upon actuation of said pushbutton, the claw of the gripping mechanism moves in the longitudinal direction of the gripping mechanism relative the guide sleeve.

The present disclosure is however not limited to the specific embodiments in which the actuating element comprises a preferably manually actuatable pushbutton. Rather, this would only be one possible realization of the actuating element for appropriately manipulating the claw of the gripping mechanism as needed.

In one possible realization of the device, the claw for grasping the stent to be compressed comprises at least one and preferably three gripper arms, whereby fastening means are provided preferably on the first end section of the at least one gripper arm which are designed to create a releasable connection with the stent to be compressed. The number of gripper arms which the claw is to comprise should conform to the number of fastening means provided on the stent to be compressed and thereby serve to connect the stent to the catheter tip of a medical delivery system.

Usually the fastening means of the stent to be compressed are provided on the distal end section of the stent. Accordingly, the fastening means provided at the first end section of the at least one gripper arm are preferably designed to create a releasable connection with the distal end section of a stent to be compressed.

The fastening means provided on the at least one gripper arm should be designed complementary to a retaining section, the corresponding fastening means respectively, of the stent to be compressed. In particular, the fastening means provided on the at least one gripper arm are designed to form a releasable engagement with the retaining section, the corresponding fastening means respectively, of the stent to be compressed. For example, it is conceivable for the fastening means provided on the at least one gripper arm to comprise at least one projecting element, for example at least one hook-shaped element, which can be brought into releasable engagement with a retaining grommet of a stent to be compressed designed correspondingly complementary thereto.

Alternatively or additionally hereto, it is likewise conceivable for the fastening means provided on the at least one gripper arm to comprise at least one recess formed in the first end section of the gripper arm which can for example be configured in the shape of a preferably oblong grommet. This recess formed in the first end section of the gripper arm should thereby be able to be brought into releasable engagement with a projecting retaining element of a stent to be compressed designed correspondingly complementary thereto. Other embodiments are also conceivable for the fastening means provided at the first end section of the at least one gripper arm.

In order to achieve the corresponding manipulating of the claw upon actuation of the actuating element of the gripper means so as to enable a grasping of the stent to be compressed, a preferred realization of the device provides for the at least one gripper arm to comprise the above mentioned fastening means at its first end section, whereby the at least one gripper arm is connected to the actuating element of the gripping mechanism by its second end section opposite its first end section. It is hereby in principle possible for the at least one gripper arm to be directly connected to the actuating element of the gripping mechanism by its second end section.

A possible realization of the device, however, may provide for the claw of the gripping mechanism to comprise a guide shaft, whereby the first end of the guide shaft is connected to the second end section of the at least one gripper arm, and whereby the second end of the guide shaft is connected to the actuating element of the gripping mechanism. The guide shaft can for example be configured as a cylindrical body.

The providing of a guide shaft connecting the at least one gripper arm to the actuating element of the gripper mechanism allows for a particularly secure manipulating of the gripper arms of the claw for grasping the stent to be compressed upon the actuating of the actuating element. Yet other solutions for connecting the at least one gripper arm to the actuating element of the gripping mechanism are also conceivable.

Preferred with the latter embodiment, in which the claw comprises a guide shaft in order to connect the at least one gripper arm to the actuating element of the gripper mechanism, is for the guide shaft to be accommodated within a guide sleeve provided for the gripping mechanism. Specifically, the guide shaft is to be accommodated within the guide sleeve such that the guide shaft together with the at least one gripper arm connected thereto is displaceable relative the guide sleeve. It is thereby further preferred for guide means to be provided to guide the guide shaft within the guide sleeve upon the displacing of the guide shaft relative the guide sleeve. Such guide means can for example be designed in the form of guiding surfaces.

An exemplary embodiment of the device disclosed herein provides for the at least one gripper arm of the claw to be connected via its second end section to the guide shaft such that the at least one gripper arm protrudes from the guide shaft at an angle relative to the longitudinal direction of the guide shaft. In so doing, the at least one gripper arm and/or a connecting area between the second end section of the at least one gripper arm and the guide shaft are configured so as to be elastically deformable such that upon a displacement of the guide shaft relative the guide sleeve, the at least one gripper arm connected to the guide shaft is at least partly received in the guide sleeve by simultaneous radial deformation. In this embodiment, the gripper arms of the claw accordingly span outward like an umbrella when the guide shaft is moved away from the actuating element relative the guide sleeve. It is thereby effortlessly possible to form a releasable connection to the stent which exhibits different respective cross-sections in the uncompressed state with one and the same gripping mechanism.

On the other hand, this embodiment allows a precompressing of the stent after the releasable connection to the stent having been formed, and does so in that the guide shaft is displaced in the direction of the actuating element relative the guide sleeve, in consequence of which the umbrella-like stretched gripper arm contracts radially. Since a retaining element preferably provided on the distal end section of the stent is respectively connected to the respective first end section of the gripper arm, a displacement of the guide shaft relative the guide sleeve precompresses at least the distal end section of the stent. The precompressing of the distal end section of the stent is effected to a maximum diameter definable by the internal diameter of the guide sleeve. Accordingly, an internal diameter should be selected for the guide sleeve which reflects a desired precompressing of the distal end of the stent.

Another embodiment of the device disclosed herein provides for the gripping mechanism to comprise a spring mechanism which interacts with the claw such that the claw can be spring-locked. It is hereby particularly preferred for the spring mechanism to comprise a spring, preferably a helical compression spring, arranged in the retaining section of the actuating element such that it pretensions the pushbutton of the actuating element against the guide sleeve. As noted above, it is preferred for the pushbutton to be designed as a manually actuatable pushbutton accommodated in the retaining section of the gripper mechanism and movable relative the guide sleeve in the longitudinal direction of the gripper mechanism.

In the latter embodiment in which the gripper mechanism comprises a spring mechanism having a spring, in particular a helical compression spring, it is preferable for the pretensioning exerted by the spring on the pushbutton of the actuating element to be selected such that without impacting the compressive force exerted externally on the pushbutton, the claw—with the exception of the fastening means provided at the first end section of the at least one gripper arm—is accommodated completely within the guide sleeve. This configuration accordingly allows the claw, the at least one gripper arm of the gripper mechanism respectively, to grasp the stent to be compressed, as well as the precompressing of the stent at least in certain areas.

In so doing, when the at least one gripper arm is driven out from the guide sleeve, said at least one gripper arm spans evenly in the radial direction. In order to achieve this, it is preferable to select the spring's stroke to be shorter than the length of the at least one gripper arm.

The gripping mechanism of the kind as disclosed herein is not mandatory for the devices described herein. Rather, providing a gripping mechanism is only a possible solution, by way of which directly touching the stent to be compressed by hand can be eliminated. Instead of a gripping mechanism as described herein, however, other mechanism are also possible.

The compressing mechanism is designed so as to exert a radially acting compressive force on at least one area of the stent accommodated in the compressing mechanism so that the cross-section of the stent to be compressed can in this way be reduced at least at certain areas. To this end, at least one clamping means, for example a clamping jaw or a clamping noose which may be formed by a looped flat strip, is provided in the interior of the compressing mechanism. The at least one clamping means is movable in the radial direction by appropriately manipulating the compressing mechanism in order to in this way adjust the internal cross-sectional diameter of the compressing mechanism at least at one area of the compressing mechanism.

By having at least certain areas of the internal cross-sectional diameter of the compressing mechanism being able to be changed by the at least one actuatable clamping means, it is possible to have a compressive force act on the outer surface of the stent at least partly accommodated in the compressing mechanism. This compressive force counters the stent's tensioning force acting in the radial direction so as to overcome it and reduce the cross-section of the stent accommodated in the compressing mechanism attachment to the catheter tip of the medical delivery system according to a sequence of events.

It is conceivable for the compressing mechanism to comprise a funnel-shaped area on at least one end. Providing a funnel-shaped area simplifies the insertion of the stent to be compressed into the interior of the compressing mechanism configured as a hollow cylindrical body. The funnel-shaped area can further be accorded the function of precompressing the stent when the stent is being inserted into the compressing mechanism through the funnel-shaped area. Accordingly, at least the end of the compressing mechanism through which the stent to be compressed is inserted into said compressing mechanism is configured as a funnel-shaped area.

Additionally to the at least one funnel-shaped area at an end of the compressing mechanism, it is also conceivable for the compressing mechanism to additionally comprise a clamping area aligned coaxially to the funnel-shaped area and connected to said funnel-shaped area. The stent to be compressed is at least partly accommodated in this clamping area after having passed through the previously mentioned funnel-shaped area. The actual compression of the stent thereby occurs in the clamping area. Accordingly, the at least one externally manipulatable clamping jaw, which is movable in the radial direction for adjusting the internal cross-sectional diameter of the compressing mechanism, is accommodated in the clamping area.

The funnel-shaped area at an end of the compressing mechanism not mandatory for the device according to the present invention.

The clamping area of the compressing mechanism may comprise a mechanism for actuating the at least one clamping means which can, for example, correspond to the mechanism of a clamping chuck. It is thus, for example, conceivable to provide a clamping area which functions according to the principle of traction.

With such a clamping area, the compressing mechanism can, for example, exhibit a tensioning screw accommodated in the clamping area which is rotatable about the longitudinal axis of the compressing mechanism relative the at least one clamping means, for example, the clamping jaw and which interacts with the at least one clamping means, for example, clamping jaw such that upon a rotation of the tensioning screw, the at least one clamping means is displaced in the longitudinal direction of the compressing mechanism relative to a clamping cone accommodated in the clamping area. Such a mechanism enables the at least one clamping means to be manipulated by rotating the tensioning screw such that it can move in the radial direction relative to the longitudinal axis of the compressing mechanism so as to enable the internal cross-sectional diameter in the clamping area of the compressing mechanism to be set to a value.

Alternatively hereto, however, it is also conceivable for the compressing mechanism to comprise a tensioning screw accommodated in the clamping area or another tensioning element which is movable in the direction of the longitudinal axis of the compressing mechanism relative the at least one clamping means, for example, clamping jaw and interacts with the at least one clamping means, for example, clamping jaw such that upon the tensioning screw moving relative the at least one clamping means, for example, clamping jaw, the at least one clamping means, for example, clamping jaw is displaced in the longitudinal direction of the compressing mechanism relative a clamping cone accommodated in the clamping area. This type of mechanism likewise enables the at least one clamping means, for example, clamping jaw to be manipulated by moving the tensioning screw or tensioning element such that it can be radially moved relative the longitudinal axis of the compressing mechanism, thus allowing the internal cross-sectional diameter to be set to a value in the clamping area of the compressing mechanism.

In general, a tensioning element shall be an element which is movable in the direction of the longitudinal axis of the compressing mechanism relative the at least one clamping means, for example, clamping jaw and which interacts with the at least one clamping means, for example, clamping jaw such that upon the tensioning screw moving relative the at least one clamping means, for example, clamping jaw, the at least one clamping means, for example, clamping jaw is displaced in the longitudinal direction of the compressing mechanism relative a clamping cone accommodated in the clamping area.

Specifically, in the latter embodiments of the clamping area, the at least one clamping means is to interact with the clamping cone such that upon a movement of the at least one clamping means, for example, clamping jaw into the clamping cone, the at least one clamping means, for example, clamping jaw is moved in the radial direction relative to the longitudinal axis of the compressing mechanism, relative to the longitudinal axis of the clamping area of the compressing mechanism respectively. As already noted above, the movement of the at least one clamping means, for example, clamping jaw into the clamping cone can be effected by rotating the tensioning screw or moving the tensioning screw in the direction of the longitudinal axis of the compressing mechanism. The clamping jaw can be moved out of the clamping cone in the same way—by rotating the tensioning screw in the opposite direction or by moving the tensioning screw in the opposite direction in the direction of the longitudinal axis of the compressing mechanism—as a consequence of which, the at least one clamping means, for example, clamping jaw is moved outward perpendicular to the radial direction away from the longitudinal axis of the clamping area of the compressing mechanism.

Alternatively to the above described realizations of the clamping area, it is equally conceivable to configure the clamping area of the compressing mechanism so as to be for example rotatable about the longitudinal axis of the compressing mechanism relative the at least one clamping means, for example, clamping jaw and interact with the at least one clamping means, for example, clamping jaw such that the at least one clamping means, for example, clamping jaw moves in the radial direction upon a rotation of the clamping area relative the at least one clamping means, for example, clamping jaw.

In a possible configuration of the latter embodiment of the clamping area, it is conceivable to configure the clamping area as a hollow cylinder exhibiting a substantially uniform external diameter, whereby the wall thickness to the clamping area configured as a hollow cylinder, however, varies along its periphery so that the internal diameter of the clamping area likewise varies. Conceivable here, for example, is for the inner lateral surface of the clamping area configured as a hollow cylinder to be of sinuous or sawtooth-like form in the unfolded state. In the case of a clamping area designed as a hollow cylinder and having a wall thickness which varies along its periphery, the at least one clamping means, for example, clamping jaw of the compressing mechanism is to abut against the inner lateral surface of the clamping area designed as a hollow cylinder such that when the clamping area is rotated relative the at least one clamping means, for example, clamping jaw, the at least one clamping means, for example, clamping jaw is moved—in dependence on the wall thickness of the hollow cylinder in the contact area with the at least one clamping means, for example, clamping jaw—in the radial direction.

Alternatively to the above described realizations of the clamping area, it is equally conceivable for the clamping area to be movable in the direction of the longitudinal axis of the compressing mechanism relative the at least one clamping means, for example, clamping jaw and to interact with the at least one clamping means, for example, clamping jaw such that upon the clamping area moving relative the at least one clamping means, for example, clamping jaw, the at least one clamping means, for example, clamping jaw is moved in the radial direction.

In one configuration of the latter embodiment of the clamping area, the clamping area is configured as a hollow cylinder, the wall thickness of which varies along its periphery, whereby the at least one clamping means, for example, clamping jaw abuts the inner lateral surface of the clamping area configured as a hollow cylinder such that upon the clamping area moving relative the at least one clamping means, for example, clamping jaw, the at least one clamping means, for example, clamping jaw is moved—in dependence on the wall thickness of the hollow cylinder in the contact area with the at least one clamping means, for example, clamping jaw—in the radial direction.

Particularly conceivable with the latter embodiments of the clamping area is for the clamping area to be movable in the direction of the longitudinal axis of the compressing mechanism relative the funnel-shaped area.

In the cited possible configurations of the clamping area of the compressing mechanism, the degree of compressive force exerted radially by the at least one clamping means, for example, clamping jaw on the stent accommodated in the compressing mechanism, in the clamping area of the compressing mechanism respectively, can be adjusted by appropriately selecting the configuration of the inner lateral surface of the clamping area configured as a hollow cylinder. Specifically, the greater degree to which the wall thickness along the periphery of the clamping area configured as a hollow cylinder increases, the larger the compressive force acting radially on the outer surface of the stent accommodated in the clamping area of the compressing mechanism by the at least one clamping means, for example, clamping jaw.

It is in principle preferred for the compressing mechanism to exhibit a plurality of actuatable clamping jaws so as to enable the most even distribution possible of the compressive force exerted on the outer surface of the stent to be compressed accommodated in the clamping area. If a hollow cylinder is used as the clamping area, its wall thickness varying along its periphery, wherein the respective clamping jaws abut the inner lateral surface of the clamping area configured as a hollow cylinder such that upon rotating the clamping area relative to the clamping jaws or upon moving of the clamping area in the direction of the longitudinal axis of the compressing mechanism relative to the clamping jaws, the clamping jaws are moved radially—in dependence on the wall thickness of the hollow cylinder in the contact area with the respective clamping jaws—it is preferred for the inner lateral surface of the clamping area configured as a hollow cylinder to be configured such that the clamping jaws move uniformly in the radial direction upon the rotating of the clamping area relative to the clamping jaws or upon the moving of the clamping area in the direction of the longitudinal axis of the compressing mechanism relative to the clamping jaws. In this way, upon the compressing of the stent in the clamping area of the compressing mechanism, this allows the achieving of the stent being radially subjected to even compressive forces from all sides in order to thus ensure an uniformly even compressing of the stent without stress peaks.

In the latter cited embodiment of the clamping area in which the clamping area is rotatable or movable relative the at least one clamping means, for example, clamping jaw about the longitudinal axis of the compressing mechanism and interacts with the at least one clamping means, for example, clamping jaw such that upon a rotation or movement of the clamping area or upon displacement in the direction of the longitudinal axis of the compressing mechanism, the at least one clamping means, for example, clamping jaw is moved in the radial direction, it is preferred for the clamping area to not only be rotatable about the longitudinal axis of the compressing mechanism relative the at least one clamping means, for example, clamping jaw or movable in the direction of the longitudinal axis of the compressing mechanism relative the at least one clamping means, for example, clamping jaw, but also relative the funnel-shaped area of the compressing mechanism. So doing simplifies the manipulating of the compressing mechanism since e.g. the user of the compressing mechanism can hold the funnel-shaped area of the compressing mechanism with his one hand while he rotates the clamping area of the compressing mechanism about the longitudinal axis of the compressing mechanism relative the funnel-shaped area or moves it in the direction of the longitudinal axis of the compressing mechanism relative the funnel-shaped area with his other hand and thus manipulates the at least one clamping means, for example, clamping jaw such that it moves in the radial direction and enables a compressing of the stent accommodated in the clamping area of the compressing mechanism.

The compressing mechanism and the gripping mechanism need not be respectively configured as separate components. The disclosure is however not limited to the previously described device for compressing a stent to which a prosthetic heart valve is affixed as needed. Rather, another object of the present disclosure also comprises a system for loading a stent, as needed with a prosthetic heart valve affixed thereto, into a medical delivery system, in particular into the catheter tip of a medical delivery system. The system may comprise a device consisting of a compressing mechanism and a gripping mechanism. Additionally to the compressing mechanism, the system further comprises a supplementary compressing mechanism.

In another embodiment of the system for loading a stent or a stent with a prosthetic heart valve affixed thereto into a medical delivery system, in particular a catheter tip of a medical delivery system, the system comprises a compressing device without a dedicated gripping mechanism. In particular, the system may comprise a device consisting only of a compressing mechanism and manipulating mechanism. Additionally to the compressing mechanism, the system further comprises a supplementary compressing mechanism, wherein the supplementary compressing mechanism may be configured analogously to the compressing mechanism.

As will be described below in detail making reference to the accompanying figures, the compressing mechanism serves to compress in particular the distal end section of the stent to be loaded into the catheter tip of a medical delivery system and to load it into a first sleeve-shaped element (receiving area) of the catheter tip. The supplementary compressing mechanism is then employed in order to compress in particular the proximal end section of the stent and load said compressed proximal end section of the stent into a further sleeve-shaped element (receiving area) of the catheter tip.

Structurally and functionally, the supplementary compressing mechanism can be configured similar to the compressing mechanism employed in the device to compress a stent. Since the supplementary compressing mechanism does not come into use until the distal end section of the stent has already been compressed and loaded into the first sleeve-shaped element of the catheter tip, it is thus in principle conceivable to make use of the compressing mechanism which was already used to compress the distal end section of the stent as the supplementary compressing mechanism. It is however also conceivable for the system to be provided with two compressing mechanisms for loading a stent into a medical delivery system, whereby one of the two compressing mechanisms is then used as the supplementary compressing mechanism.

Thus, both the above described device, with which a stent, as needed with a prosthetic heart valve affixed thereto, can be readily compressed, as well as the above described system thereto, provides for loading a stent, as needed with a prosthetic heart valve affixed thereto, into a medical delivery system, in particular into a catheter tip of a medical delivery system.

The present disclosure further relates to a method for loading a stent, as needed with a prosthetic heart valve affixed thereto, into a medical delivery system, in particular into the tip of a catheter of a medical delivery system. The method comprises the following method steps:

i) furnishing a device, i.e. a device consisting of a compressing mechanism and a manipulating mechanism, or a system, i.e. a system comprising a device consisting of a compressing mechanism and manipulating mechanism;

ii) inserting a stent or a stent with a prosthetic heart valve affixed thereto into the compressing mechanism such that the stent is at least partly accommodated in the compressing mechanism;

iii) moving the manipulating mechanism of the device relative to the compressing mechanism thereby moving the at least one clamping means in the radial direction for adjusting the internal cross-sectional diameter of the compressing mechanism such that at least parts of the stent, in particular parts of the upper end section of the stent, are at least partly compressed; and iv) inserting the at least partly compressed stent into a first sleeve-shaped element of the catheter tip of the medical delivery system.

Prior to the inserting at least partly compressed stent into a first sleeve-shaped element of the catheter tip, it is conceivable to further reduce the cross-sectional diameter of the stent. For this purpose, a compressing mechanism as described hereinafter may be used. In particular, the operator may insert the at least partly compressed stent into a supplementary compressing mechanism of a compressing device which is configured analogously to the inventive device. Thereafter, the operator shall move the manipulating mechanism of the supplementary compressing device relative to the compressing mechanism of the supplementary compressing device in order to move the at least one clamping means of the supplementary compressing device in the radial direction for adjusting the internal cross-sectional diameter of the compressing mechanism of the supplementary compressing device and for at least partly further compressing the stent by exerting a compressive force in radial direction on at least parts of the stent accommodated in the compressing mechanism of the supplementary compressing device.

Furthermore, it is conceivable to force the at least party compressed stent such as that the at least party compressed stent passes through a cone thereby further reducing the cross-sectional diameter of the stent. For example, the at least partly compressed stent may be pushed through the cone by using a push rod.

Of course, the method for loading a stent into e.g. the catheter tip of a medical delivery system is also realizable when furnishing a device consisting of a compressing mechanism and gripping mechanism. In this case, the gripping mechanism of the device is first connected with the compressing mechanism such that the gripping mechanism is at least partly accommodated within the compressing mechanism. It is hereby preferred for at least one guiding element to be designated for the gripping mechanism which is configured to be complementary to at least one guiding element designated for the compressing mechanism and which engages with the guiding element of the compressing mechanism when the gripping mechanism connects to the compressing mechanism.

After the gripping mechanism connects to the compressing mechanism, the stent to be accommodated for example in the catheter tip of the medical delivery system is grasped, and is done so in that by actuating the actuating element of the gripping mechanism, the claw of the gripping mechanism is accordingly manipulated so that a releasable connection is formed between a distal end section of the stent and the claw of the gripping mechanism. As already detailed in conjunction with the device for compressing a stent, it is preferred for a precompressing of at least the distal end section of the stent to occur upon the grasping of the stent. This can be realized when following the forming of a releasable connection between the distal end section of the stent and the claw of the gripping mechanism, the claw is moved toward the actuating element relative the preferably provided guide sleeve by the actuating of the actuating element.

A further precompressing of the stent occurs in a subsequent method step in which the gripping mechanism with the claw, to which the distal end section of the stent is releasably affixed, is moved in the longitudinal direction relative the compressing mechanism such that the stent is at least partly accommodated within the compressing mechanism. By the gripping mechanism moving in the longitudinal direction of the compressing mechanism relative said compressing mechanism, the stent releasably connected to the claw of the gripping mechanism is thus introduced into the interior of the compressing mechanism. It is hereby advantageous for the compressing mechanism to exhibit the previously described funnel-shaped area at the insertion end of the compressing mechanism in order to facilitate the insertion of the stent into the compressing mechanism, the clamping area of the compressing mechanism respectively.

After the stent, as needed with a prosthetic heart valve affixed thereto, has been at least partly accommodated inside the compressing mechanism, the connection between the stent and the gripping mechanism is disengaged. This ensues by a re-actuating of the actuating element of the gripping mechanism so that the claw of the gripping mechanism can be manipulated such that it moves relative to the gripping mechanism and the connection between the distal end section of the stent and the claw is disengaged.

After the gripping mechanism releases from the stent, the actual compressing of at least the distal end section of the stent occurs in the clamping area of the compressing mechanism. To this end, the at least one clamping means, for example, clamping jaw of the compressing mechanism is manipulated such that the at least one clamping means, for example, clamping jaw moves radially relative the compressing mechanism perpendicular to the direction of the longitudinal axis of the compressing mechanism. As previously described in conjunction with the device, the manipulating of the at least one clamping means, for example, clamping jaw can ensue for example by the corresponding actuating of a clamping chuck-like mechanism of the compressing mechanism which effects a movement of the at least one clamping means, for example, clamping jaw in the direction of the longitudinal axis of the compressing mechanism.

After at least the distal end section of the stent being thus so compressed in defined manner in the compressing mechanism such that the diameter of at least the distal end section of the stent exhibits a predefinable value, the compressed distal end section of the stent is introduced into a first sleeve-shaped element (receiving area) of the catheter tip of the medical delivery system.

The method for loading a stent into the catheter tip of a medical delivery system preferably provides for the compressing mechanism to introduce at least the distal end section of the stent into at least one area of the catheter tip of the medical delivery system prior to the manipulation of the at least one clamping means, for example, clamping jaw during the actual compressing. Only after the compressing mechanism with the stent accommodated therein is inserted into the tip of the catheter of the medical delivery system does the actual compressing of at least the distal end section of the stent occur by the appropriate manipulating of the at least one clamping means, for example, clamping jaw of the compression mechanism. This occurs because the diameter of the compressed distal end section of the stent is normally smaller than the external diameter of the catheter tip of the medical delivery system such that the actual compressing of the distal end section of the stent is to occur in direct proximity to the first sleeve-shaped element of the catheter tip.

In order to achieve that also the proximal end section of the stent can be accommodated in compressed manner in the catheter tip of the medical delivery system, a preferred embodiment of the method makes use of the above noted supplementary compressing mechanism. Specifically, it is thereby provided that at least one area of the catheter tip of the medical delivery system is inserted through the supplementary compressing mechanism configured as a hollow cylindrical body such that the supplementary compressing mechanism abuts against the (not yet fully compressed) proximal end section of the stent at least partly accommodated within the compressing mechanism.

Before the supplementary compressing mechanism is used to compress the proximal end section of the stent, however, it is preferable to remove the compressing mechanism, with which the distal end section of the stent is compressed, from the catheter tip of the medical delivery system. This should occur after the compressed distal end section of the stent has been loaded into the first sleeve-shaped element of the catheter tip.

To remove the compressing mechanism, the at least one clamping means, for example, clamping jaw of the compressing mechanism is manipulated such that the at least one clamping means, for example, clamping jaw is moved radially outward relative the compressing mechanism away from the longitudinal axis of the compressing mechanism. Because the distal end section of the stent is already loaded into the first sleeve-shaped element of the catheter tip, the distal end section of the stent remains in its compressed form although the at least one clamping means, for example, clamping jaw of the compressing mechanism now no longer exerts a radially acting compressive force on the stent.

After the at least one clamping means, for example, clamping jaw of the compressing mechanism being manipulated so as to no longer exert any radial compressive force on the outer surface of the stent, the compressing mechanism can be removed from the catheter tip of the medical delivery system.

The supplementary compressing mechanism can thereafter be used to compress the not yet fully compressed proximal end section of the stent such that the proximal end section of the stent can be loaded into a further sleeve-shaped element of the catheter tip.

To this end, the supplementary compressing mechanism is moved toward the proximal end section of the stent such that at least the proximal end section of the stent is at least partly received within the supplementary compressing mechanism configured as a hollow cylindrical body. In this position, the supplementary compressing mechanism can effect a compressing of at least the proximal end section of the stent.

In detail, at least the proximal end section of the stent is compressed in that the at least one clamping means, for example, clamping jaw of the supplementary compressing mechanism is manipulated such that the at least one clamping means, for example, clamping jaw is radially moved relative the supplementary compressing mechanism perpendicular to the direction of the longitudinal axis of said supplementary compressing mechanism. It is readily apparent that the degree of compression of the proximal end section of the stent is selectable at will, and this is done by correspondingly selecting the extent of manipulation for the at least one clamping means, for example, clamping jaw of the supplementary compressing mechanism. The same also applies figuratively to the compressing of the distal end section of the stent.

After the supplementary compressing mechanism compressing the proximal end section of the stent, the compressed proximal end section of the stent is introduced into at least one second sleeve-shaped element (receiving area) of the catheter tip of the medical delivery system.

The supplementary compressing mechanism can thereafter also be removed from the catheter tip of the medical delivery system. This ensues by correspondingly manipulating the at least one clamping means, for example, clamping jaw of the supplementary compressing mechanism such that the at least one clamping means, for example, clamping jaw is radially moved outward relative the supplementary compressing mechanism perpendicular to the radial direction of the longitudinal axis of said supplementary compressing mechanism.

BRIEF DESCRIPTION OF THE DRAWINGS

The following will make reference to the accompanying drawings in describing examples of the disclosed solution. Shown are.

DETAILED DESCRIPTION

Figure 1:
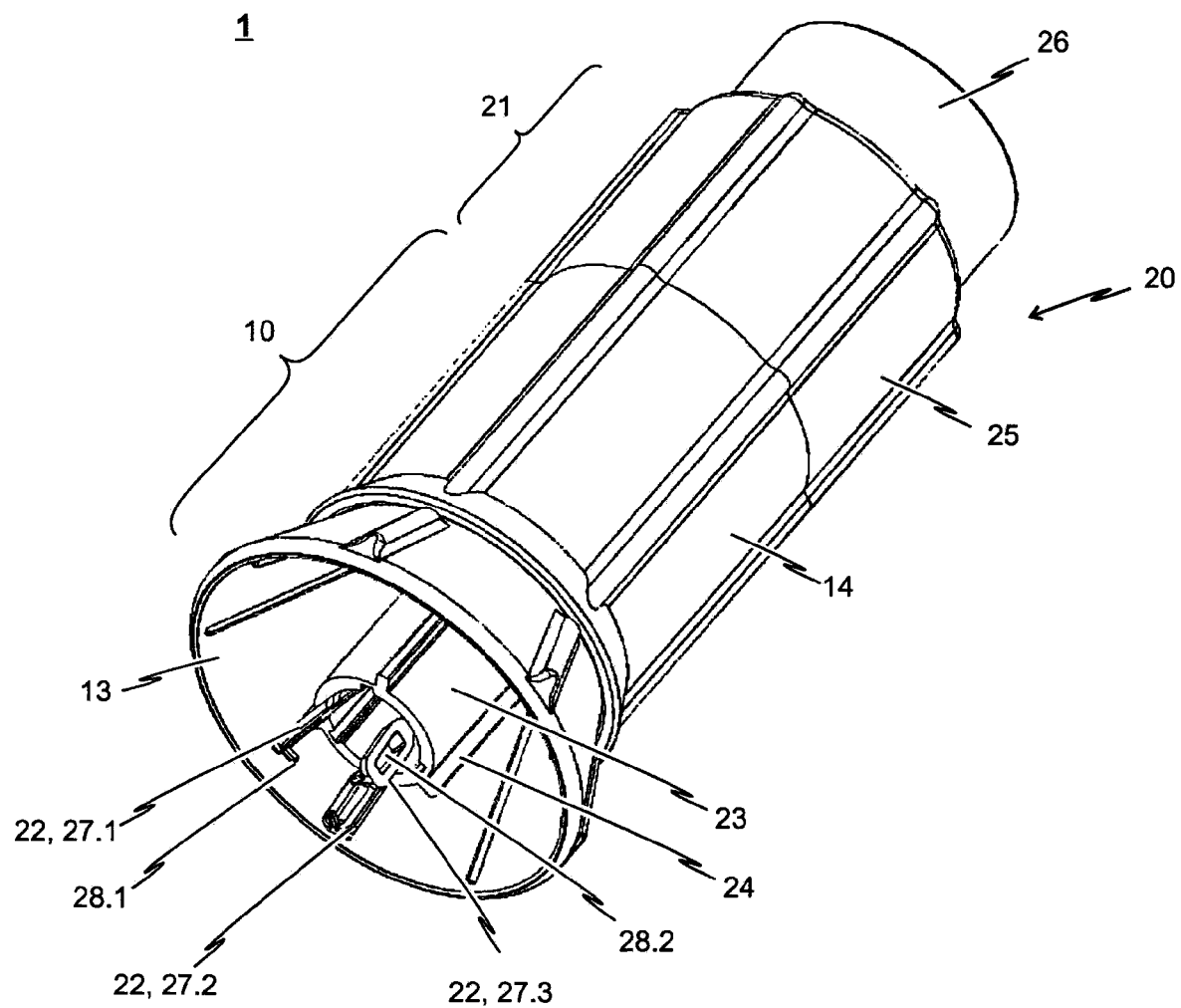
FIG. 1 a perspective view of a first exemplary embodiment of the disclosed device for compressing a stent, wherein the device is shown in its initial state.

Reference will be made in the following to FIGS. 1 to 10 in describing a first exemplary embodiment of the device 1 for compressing a stent 100. FIG. 1 shows a perspective view of the first exemplary embodiment of the device 1 in its initial state; i.e. a state in which the device 1 is received from the factory.

The device 1 substantially comprises a compressing mechanism 10 in the form of a hollow cylindrical body, within which a stent, not shown in FIG. 1, can be at least partly received. Particular reference will be made in the following to the representations shown in FIGS. 6 to 9 in describing the structure and the functioning of the compressing mechanism 10 in greater detail.

The first exemplary embodiment of device 1 depicted in FIG. 1 further comprises a gripping mechanism 20 which in the initial state of device 1 is at least partly accommodated within the compressing mechanism 10 configured as a hollow cylinder. Particular reference will be made in the following to the representations shown in FIGS. 3 to 5 in describing the structure and the functioning of the gripping mechanism 20 in greater detail.

As will subsequently be described in detail in the following, the compressing mechanism 10 serves the device 1 with respect to the exerting of a compressive force acting in the radial direction (relative the longitudinal direction of said compressing mechanism 10) on a stent accommodated in the compressing mechanism 10 in defined manner so as to reduce the cross-section of the stent to a predefinable value. In doing so, it is first required for the stent to be compressed to be at least partly inserted into the compressing mechanism 10 configured as a hollow cylinder. This task is assumed by the gripping mechanism 20 of the device 1 which—as will be described below in greater detail—is designed so as to create a releasable connection with the stent to be compressed. In particular, the gripping mechanism 20 serves to create a releasable connection with the distal end section of the stent to be compressed and thereafter introduce the stent into the compressing mechanism 10 configured as a hollow cylinder.

To this end, the gripping mechanism 20 is displaceably receivable within the compressing mechanism 10 configured as a hollow cylinder in the longitudinal direction relative said compressing mechanism 10. The gripping mechanism 20 further comprises an actuating element 21 provided with a claw 22 for grasping the stent to be compressed.

In the first exemplary embodiment depicted in FIGS. 1 to 10, the actuating element 21 of the gripping mechanism 20 exhibits a manually actuatable pushbutton 26 accommodated in a retaining section 25 and displaceable in the longitudinal direction of the gripping mechanism 20 relative a guide sleeve 23.

Figure 2:
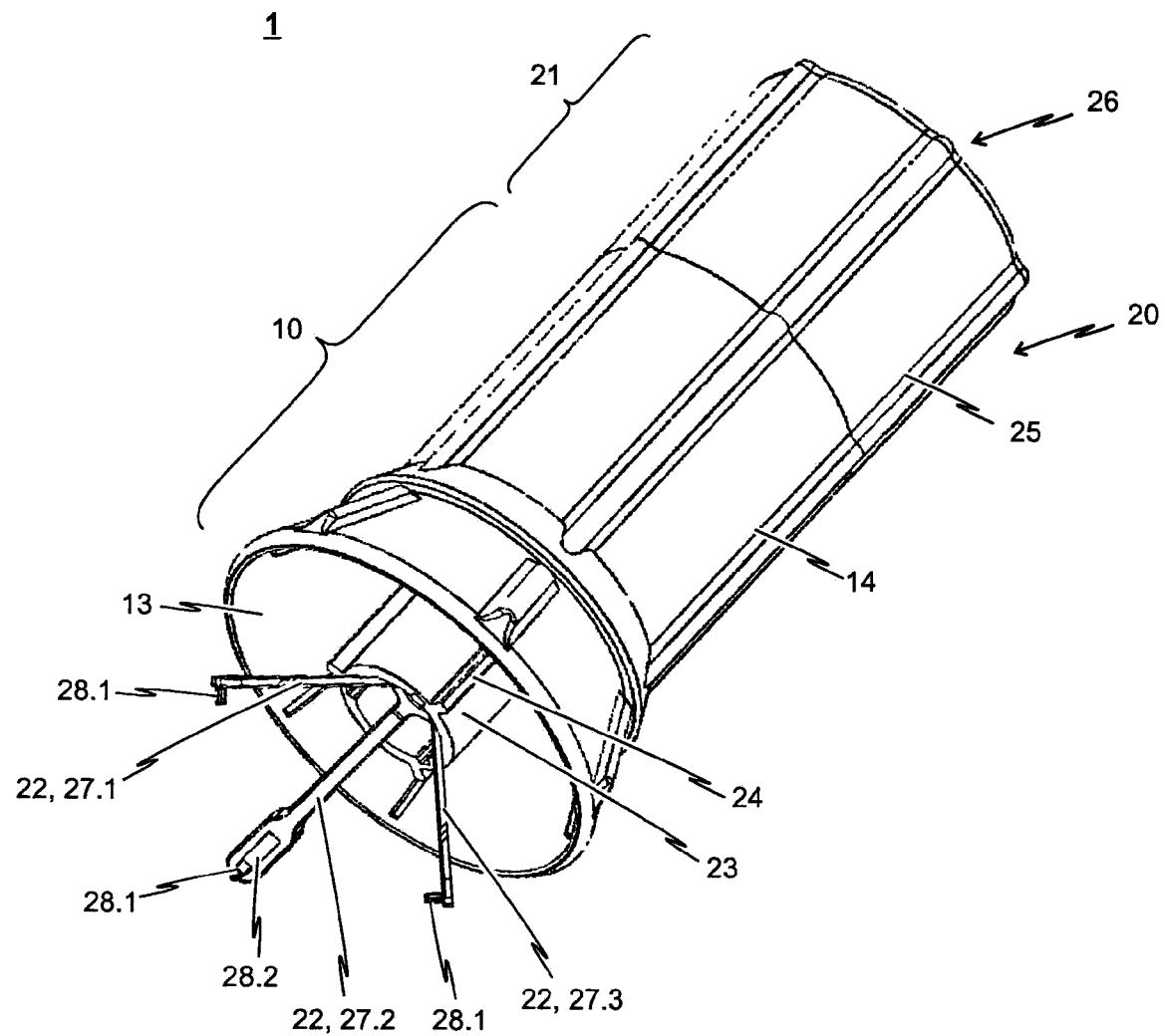
FIG. 2 a perspective view of the first exemplary embodiment of the disclosed device for compressing a stent in a stent-grasping state.

To be seen in conjunction hereto from the representation provided in FIG. 2 is that upon the actuating of actuating element 21; i.e. upon an external compressive force being exerted on the manually actuatable pushbutton 26, the pushbutton 26 is moved in the longitudinal direction of the gripping mechanism 20 relative retaining section 25. The pushbutton 26 is directly connected to the claw 22 of the gripping mechanism 20 so that upon the pushbutton 26 being actuated, actuating element 21 moves the claw 22 in the longitudinal direction of the gripping mechanism 20 relative the guide sleeve 23.

By actuating element 21 being pressed by the pushbutton 26—as shown in FIG. 2—the claw 22 of gripping mechanism 20 is thus at least partly moved out of the guide sleeve 23. The distance by which the claw 22 is moved out of the guide sleeve 23 depends on the actuated travel of the pushbutton 26.

In the first exemplary embodiment of device 1, the claw 22 exhibits three gripper arms 27.1, 27.2, 27.3, whereby each gripper arm 27.1, 27.2, 27.3 comprises respective fastening means 28.1, 28.2 at its first end section. These fastening means 28.1, 28.2 serve to form a releasable connection with a stent to be compressed, as will be subsequently described in detail referencing the representations provided in FIGS. 10a to 10f.

The fastening means 28.1, 28.2 respectively provided on the first end sections of the gripper arms 27.1, 27.2, 27.3 are designed in complementary fashion to a retaining section formed on the stent to be compressed so that the fastening means 28.1, 28.2 are designed to releasably engage with a retaining section of the stent to be compressed. In detail, and as can particularly be seen from the representations provided in FIGS. 1 to 5, the respective fastening means 28.1, 28.2 provided on the respective gripper arms 27.1, 27.2, 27.3 in the first exemplary embodiment of the device 1 exhibit a projecting element 28.1 which can be brought into releasable engagement with a correspondingly complementary-configured retaining grommet of a stent to be compressed. Additionally to this projecting element 28.1, recesses 28.2 particularly in the form of a preferably oblong grommet are formed in the respective first end sections of the gripper arms 27.1, 27.2, 27.3. Each of said recesses 28.2 can be brought into releasable engagement with a correspondingly complementary-configured projecting retaining element of a stent to be compressed.

The gripping mechanism 20 used in the first exemplary embodiment of the device 1 will be described in greater detail in the following referencing the representations provided in FIGS. 3 to 5. Specifically, FIG. 3 shows a perspective view of the gripping mechanism 20 in its initial state; i.e. in a state in which the pushbutton 26 of actuating element 21 has not been actuated.

As already described in conjunction with the FIG. 1 representation, the claw 22 with gripper arms 27.1, 27.2, 27.3 is accommodated so far into the guide sleeve 23 in the initial state of the gripping mechanism 20 that only the fastening means 28.1, 28.2 provided on the first end sections of the gripper arms 27.1, 27.2, 27.3 protrude from the open ends of the guide sleeve 23. The remaining parts of the gripper arms 27.1, 27.2, 27.3, the claw 22 respectively, are accommodated within the guide sleeve 23 configured as a hollow cylindrical body.

Figure 3:
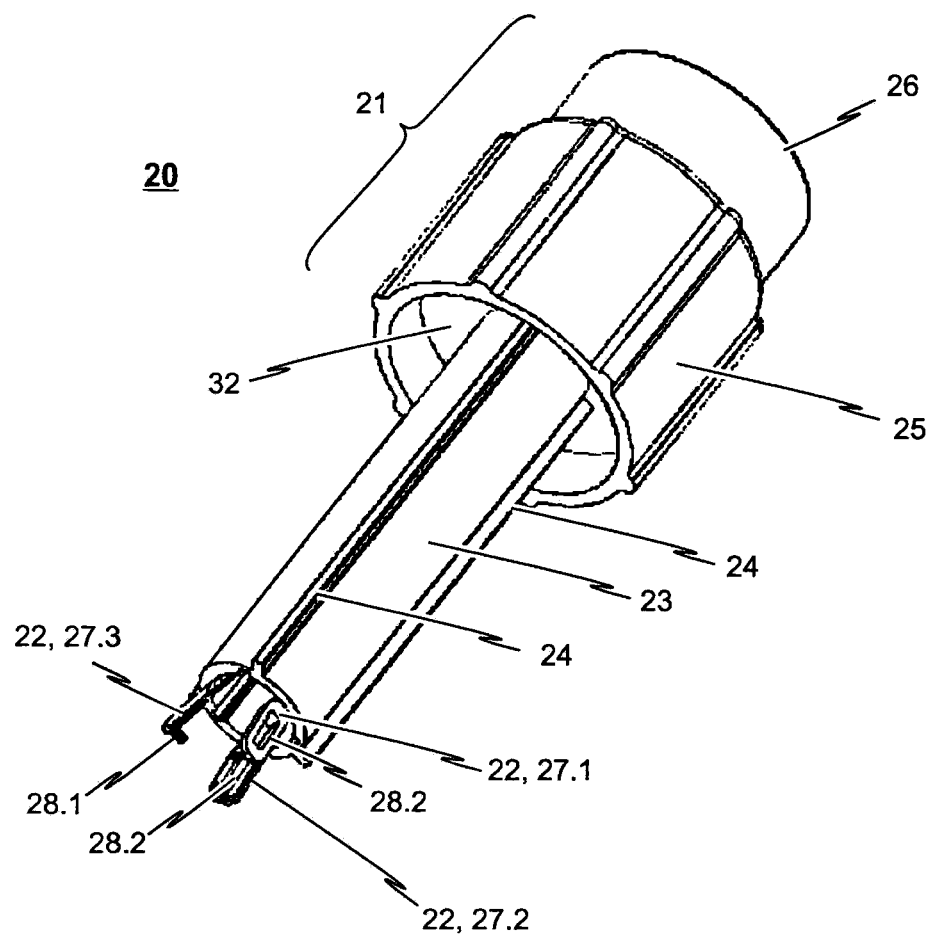
FIG. 3 a perspective view of the initial state of the gripping mechanism used in the first exemplary embodiment of the disclosed device for compressing a stent.
Figure 4:
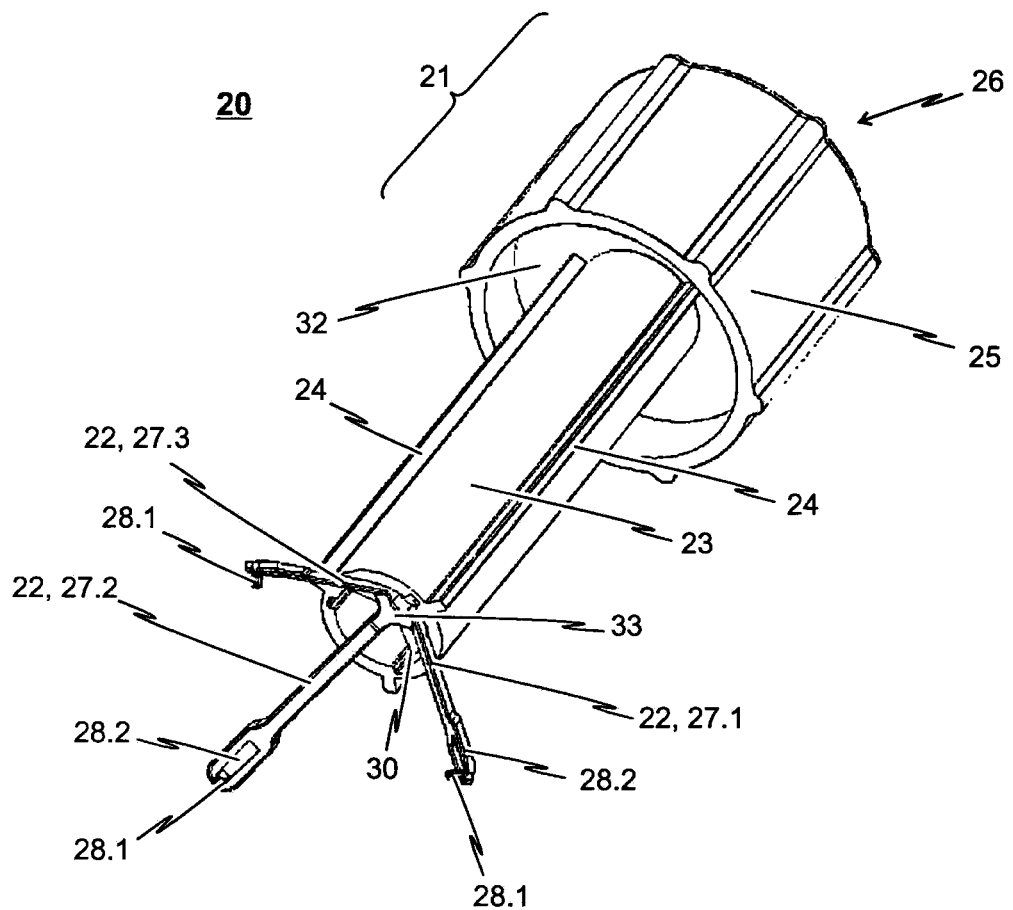
FIG. 4 a perspective view of the gripping mechanism used in the first exemplary embodiment of the disclosed device in a stent-grasping state.

FIG. 4 shows the gripping mechanism 20 depicted in FIG. 3 in a state prepared to grasp a not explicitly shown stent. Specifically, in the state of the gripping mechanism 20 shown in FIG. 4, the pushbutton 26 of actuating element 21 has been actuated such that the claw 22 with the gripper arms 27.1, 27.2, 27.3 will be displaced in the longitudinal direction of the gripping mechanism 20 relative the guide sleeve 23 and the retaining section 25 to which the guide sleeve 23 is fixedly connected such that not only the respective fastening means 28.1, 28.2 of gripper arms 27.1, 27.2, 27.3 protrude out of the open end of the guide sleeve 23, but also the actual gripper arms 27.1, 27.2, 27.3 themselves. When the gripper arms 27.1, 27.2, 27.3 are extended out of the end of the guide sleeve 23, they radially span outward like an umbrella—as can in particular be seen in the FIG. 4 representation—such that the effective gripping area of claw 22, gripper arms 27.1, 27.2, 27.3 respectively, is increased.

It is preferred for the maximum gripping area of claw 22, gripper arms 27.1, 27.2, 27.3 respectively, to be such so as to be able to grasp stents up to an external diameter of 30.0 mm. However, it is of course also possible to dimension the gripping area of claw 22 for stents having larger external diameters.

As will be described in greater detail referencing the representations provided in FIGS. 10a-f, the gripping mechanism 20 already effects a precompressing of a stent grasped by the claw 22. If the gripping mechanism 20 namely transforms back to its state as shown in FIG. 3 from that as shown in FIG. 4 by the releasing of pushbutton 26 of actuating element 21, the gripper arms 27.1, 27.2, 27.3 will pull claw 22 back into the guide sleeve 23 configured as a hollow cylinder, which will have the consequence of the stent releasably connected via the fastening means 28.1, 28.2 provided at the first end sections of the gripper arms 27.1, 27.2, 27.3 also being moved along therewith in the radial direction. In this way, at least the area of the stent to be compressed at which the gripper arms 27.1, 27.2, 27.3 of the gripping mechanism 20 are connected can be precompressed. The extent of precompression effected via the gripping mechanism 20 is dependent on the internal diameter of the guide sleeve 23 configured as a hollow cylinder.

Figure 5:
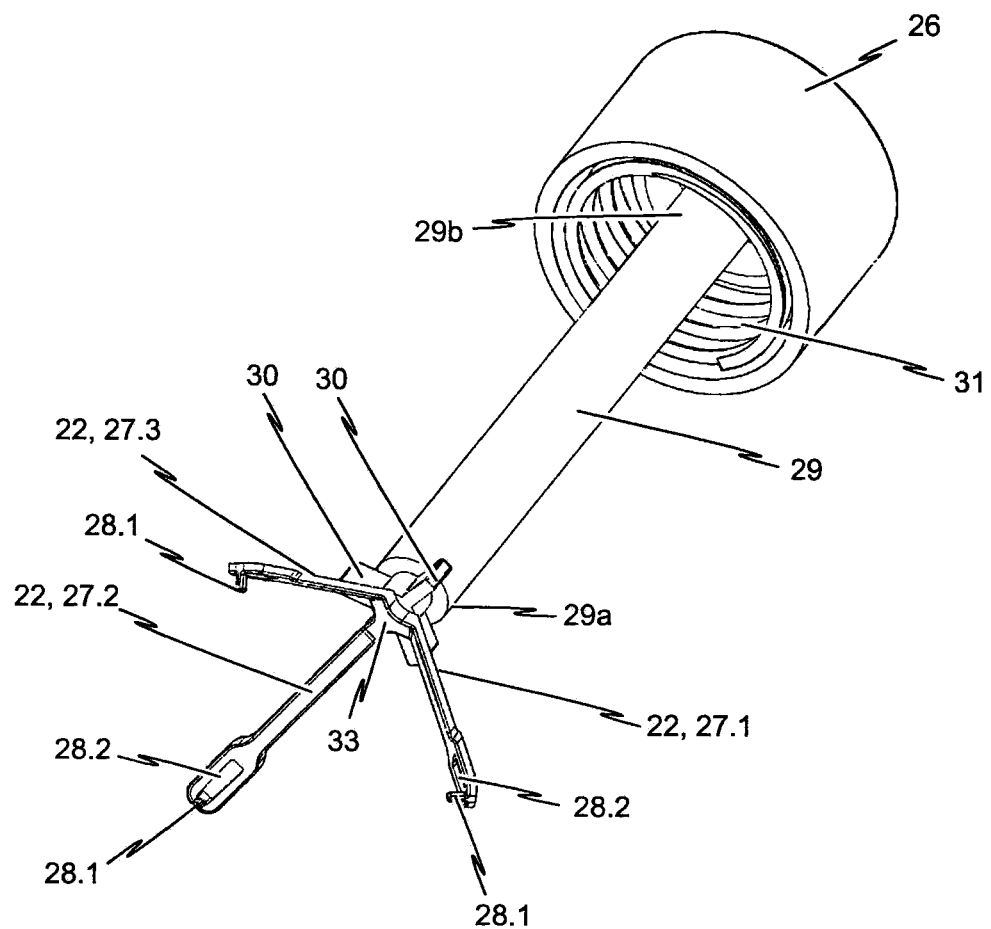
FIG. 5 a perspective view of the gripping mechanism used in the first exemplary embodiment of the disclosed device for compressing a stent without a guide sleeve.

FIG. 5 shows a perspective view of a gripping mechanism 20 used in the first exemplary embodiment of the device 1 without guide sleeve 23. It is especially to be seen from the representation of FIG. 5 that the claw 22 of gripping mechanism 20 comprises a guide shaft 29 additionally to gripper arms 27.1, 27.2, 27.3 which can, for example, be of substantially cylindrical design. The first end 29a of guide shaft 29 is connected to the respective second end sections of gripper arms 27.1, 27.2, 27.3, whereby the second end 29b of guide shaft 29 is connected to the actuating element 21 of gripper mechanism 20 and specifically to the pushbutton 26 of the actuating element 21.

It is of course also conceivable to dispense with the guide shaft 29 and directly connect the second end sections of the respective gripper arms 27.1, 27.2, 27.3 to the actuating element 21 of the gripping mechanism 20, respectively to the pushbutton 26 of said actuating element 21. However, the guide shaft 29 enables the claw 22 to be moved with as little resistance as possible relative the guide sleeve 23 upon actuating element 21 being actuated.

In order to prevent the possible canting or wedging of the guide shaft 29 in its movement relative to the guide sleeve 23 upon the actuating element 21 being actuated, the first exemplary embodiment of device 1 provides guiding means 30 to guide the guide shaft 29 within the guide sleeve 23 when the guide shaft 29—as depicted for example in FIGS. 3 and 4—is accommodated within the guide sleeve such that the guide shaft 29 together with the gripper arms 27.1, 27.2, 27.3 connected to said guide shaft 29 can be displaced relative to guide sleeve 23.

To be noted from the FIG. 5 representation is that the guide means 30 are designed as protruding guiding surfaces provided at the first end section 29a of guide shaft 29. However, it is of course also conceivable to dispose guiding means 30 in another area of guide shaft 29.

As can be noted from the perspective representation according to FIG. 5, the gripping mechanism 20 further comprises a spring mechanism in the form of a helical compression spring 31 accommodated in the retaining section 25 and pretensioning the pushbutton 26 of actuating element 21 against the guide sleeve 23 via the underface 32 of the retaining section 25 in the assembled state of gripping mechanism 20 (cf. FIGS. 3 and 4). It is thereby specifically provided for the guide sleeve 23 to be fixedly connected to the underface 32 of retaining section 25.

Providing the spring mechanism in retaining section 25 of actuating element 21 as realized by means of the spring 31 thus ensures that the gripping mechanism 20 will be held in the initial state as shown in FIG. 3 in the assembled state of said gripping mechanism 20 (cf. FIGS. 3 and 4), as long as no opposing force exceeding the pretensioning force exerted by the spring 31 is exerted on pushbutton 26 of actuating element 21. In the gripping mechanism 20 used in the first exemplary embodiment of the device 1, the guide shaft 29 is namely connected to the claw 22 via the underside of pushbutton 26 such that force exerted on the pushbutton 26 via spring 31 is transmitted from the pushbutton 26 to the guide shaft 29, claw 22 respectively.

Selecting the appropriate spring constant or stiffness to spring 31 of the spring mechanism enables spring 31 to set the pretensioning exerted on pushbutton 26 of actuating element 21. To be factored in hereby is that the pretensioning is to be selected such that without impacting any compressive force exerted externally on the pushbutton 26; i.e. in the initial state of the gripping mechanism 20, the claw 22—with the exception of the fastening means 28.1, 28.2 provided at the first end section of gripper arms 27.1, 27.2, 27.3—is completely accommodated within guide sleeve 23. This should preferably also be the case when the claw 22 grasps a stent to be compressed via the fastening means 28.1, 28.2 of gripper arms 27.1, 27.2, 27.3.

As already indicated with reference to the FIG. 1 and FIG. 2 representation, the gripping mechanism 20 is at least partly accommodated within the compressing mechanism 10 so as to be displaceable in the longitudinal direction relative the compressing mechanism 10. In order to guide the relative motion of the gripping mechanism 20 accommodated in the compressing mechanism 10, and in particular to facilitate the receiving of the gripping mechanism 20 within the compressing mechanism 10, the guide sleeve 23 comprises guiding elements 24 which are configured as guide rails in the first exemplary embodiment depicted in FIGS. 1 to 10. These guiding elements 24 configured as guide rails extend in the longitudinal direction of the guide sleeve 23 and are configured complementary to the guiding elements 12 allocated to the compressing mechanism 10. The guiding elements 12 allocated to the compressing mechanism 10 can be noted from the FIG. 9b representation which shows a perspective view from below into the funnel-shaped area 13 of the compressing mechanism 10 shown in FIG. 6 without a stent.

Figure 9A:
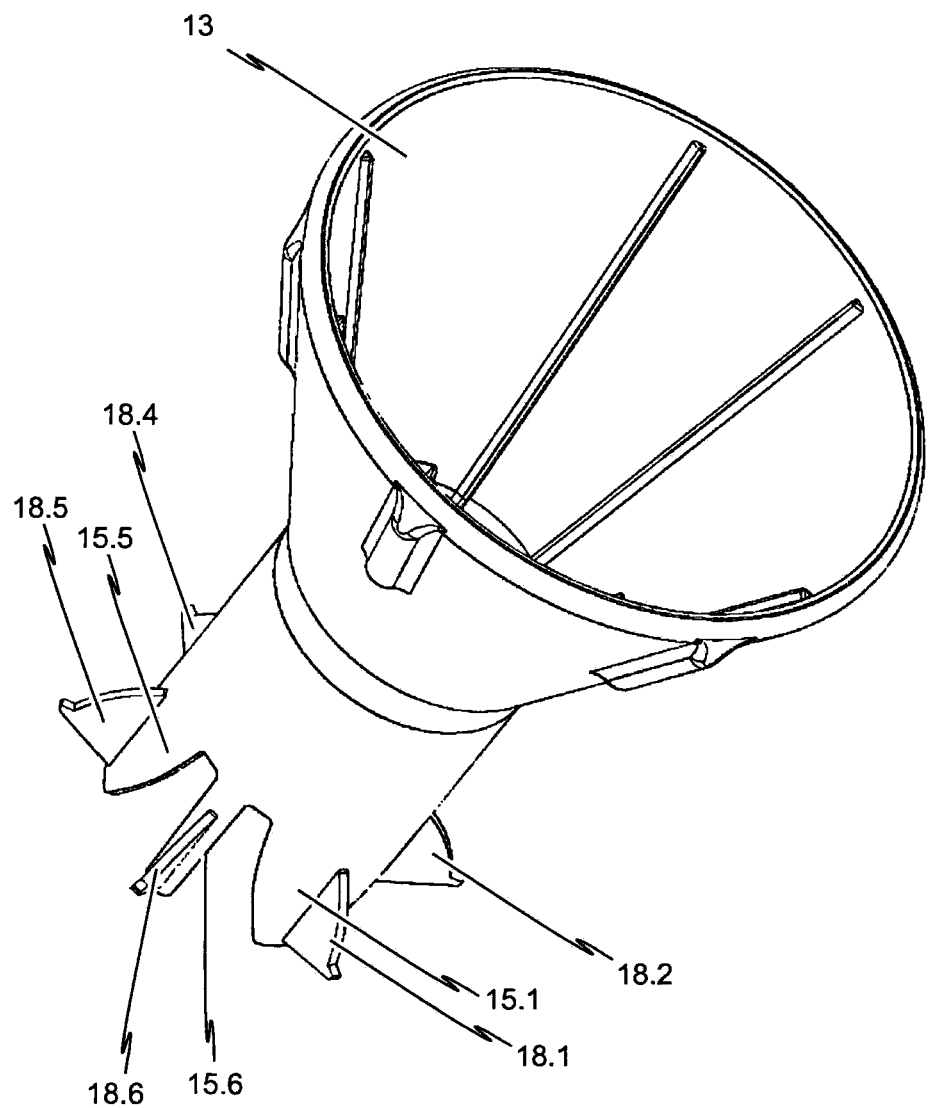
FIG. 9a a perspective view of the clamping mechanism used in the clamping area of the compressing mechanism of the first exemplary embodiment of the disclosed device for compressing a stent.
Figure 9B:
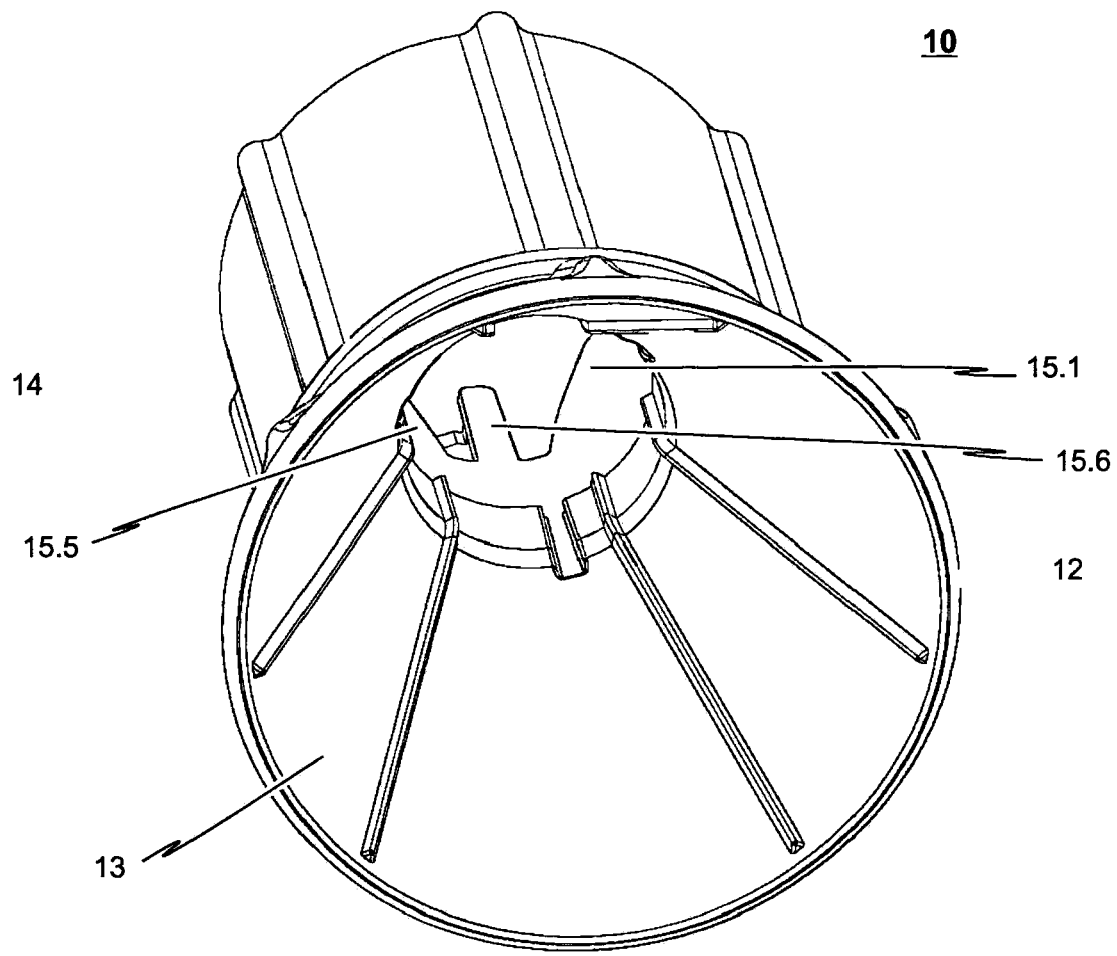
FIG. 9b a perspective view from below into the funnel-shaped area of the compressing mechanism shown in FIG. 6 without a stent.

As can be seen for example in the representation of FIG. 9b, the guiding elements 12 allocated to compressing mechanism 10 are configured as guiding grooves extending in the longitudinal direction of compressing mechanism 10.

It can in particular be noted from the FIG. 5 representation that the gripper arms 27.1, 27.2, 27.3, and preferably also the connecting area 33 between the end sections of the gripper arms 27.1, 27.2, 27.3 and the first end section 29a of guide shaft 29, are configured to be elastically deformable such that upon a displacement of the guide shaft 29 relative the guide sleeve 23, the gripper arms 27.1, 27.2, 27.3 connected to the guide shaft 29 can be at least partly accommodated in the guide sleeve 23 under simultaneous radial elastic deformation.

Figure 6:
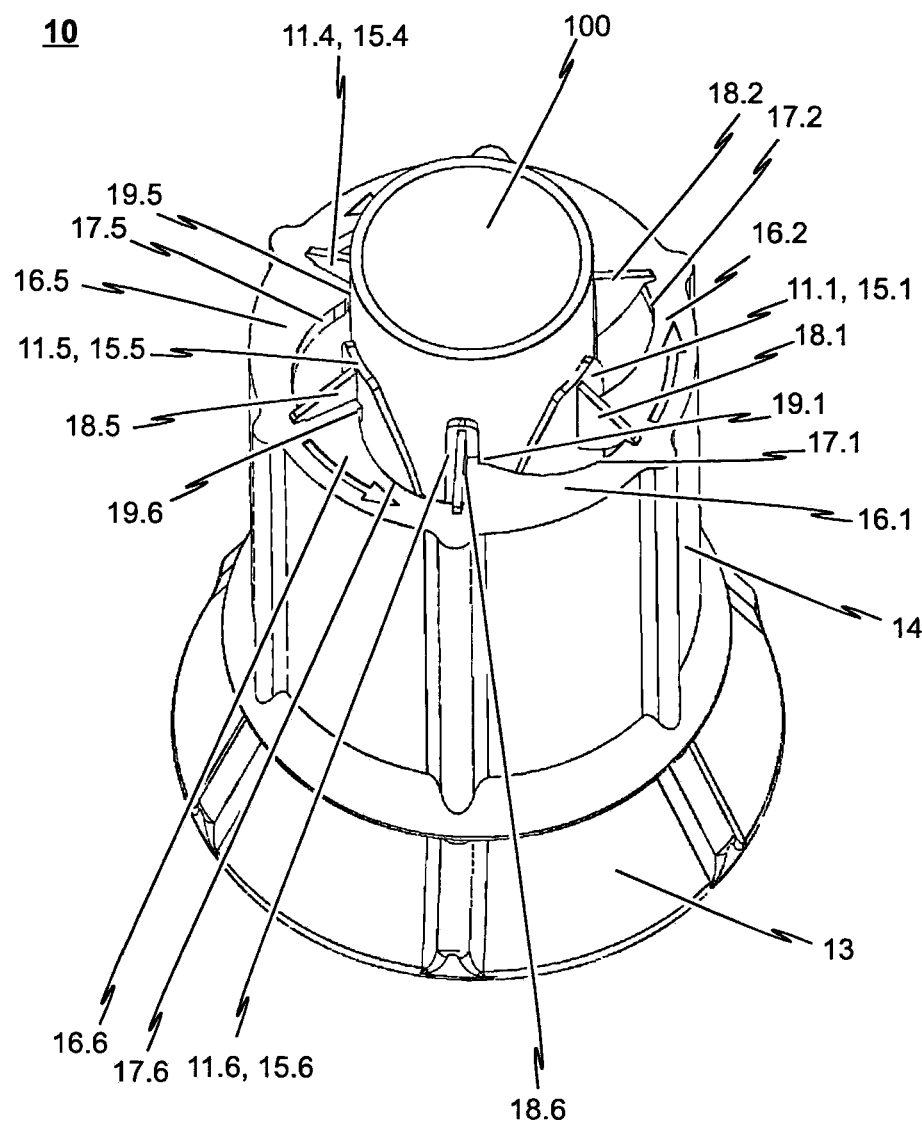
FIG. 6 a perspective view of the compressing mechanism used in the first exemplary embodiment of the disclosed device with a stent at least partly accommodated therein prior to the actual compressing of the stent in the compressing mechanism.

The compressing mechanism 10 used in the first exemplary embodiment of the device 1 will be described in the following making reference to the FIG. 6 to FIG. 9b representations. Specifically, FIG. 6 shows a perspective view of the compressing mechanism 10 used in the first exemplary embodiment of the device 1, within which a stent 100 is at least partly accommodated prior to its actual compressing.

It is hereby noted that only for the sake of clarity in the drawings, the stent 100 is depicted schematically as a cylindrical body without any further rendering of the stent's structural details. The device 1 is suited for cylindrical stents with which the gripping mechanism 20 can create a releasable connection in order to introduce the stent 100 into the compressing mechanism 10. In particular, the device is suited to compress a stent 100 which comprises retaining elements on its upper end section 101 with which the gripping mechanism 20 can form a releasable connection.

The device 1 is suited to compress an expandable, and in particular self-expandable stent 100. The stent 100 assumes—while it is accommodated in the catheter tip of the medical delivery system—a first shape. However, outside of the catheter tip, in the implanted state respectively, the stent 100 is in a second shape. The first shape of the stent 100 thereby corresponds to the folded state while, in the expanded state, the stent 100 is in its second shape.

For example, the device 1 is suitable for compressing a stent 100 as described for example in European patent application No. 07 110 318 or European patent application No. 08 151 963. A preferred realization of device 1 accordingly designed to compress a stent 100 thus comprises the following:

a first retaining section, lower end section respectively, to which a prosthetic heart valve can be affixed;

an oppositely-arranged second retaining section, upper end section respectively, having at least one retaining element, for example in the form of a retaining grommet or in the form of a retaining head, whereby the at least one retaining element of the stent can be brought into releasable engagement with a stent holder of a delivery system's catheter tip;

at least one retaining holder to which a prosthetic heart valve can be affixed; and at least one and preferably three positioning holders which are designed to engage in the pockets of the native heart valve in the implanted state of the stent in order to thus enable the self-positioning of the stent in the aorta of the patient.

The use of device 1 is however in no way limited to this type of stent.

As can be seen from the FIG. 6 representation, the compressing mechanism 10 exhibits a funnel-shaped area 13 at one end. A clamping area 14, aligned coaxially and connected to the funnel-shaped area 13, adjoins said funnel-shaped area 13. The clamping area 14 of the compressing mechanism 10 serves in exerting a radially acting compressive force in defined manner on a stent 100 accommodated in the compressing mechanism 10 such that the cross-section of the stent 100 can be reduced to a predefinable value. To this end, the compressing mechanism 10 exhibits clamping jaws 11.1 to 11.6 individually accommodated in the clamping area 14. These clamping jaws 11.1 to 11.6 can be radially moved to adjust the internal cross-sectional diameter of the compressing mechanism 10 in clamping area 14.

As will be described in greater detail below referencing the FIG. 9a representation, a suitable clamping mechanism is used for this purpose which can be externally manipulated in order to move the clamping jaws 11.1 to 11.6 in the radial direction.

In detail, the first exemplary embodiment of the device 1 provides for the clamping area 14 to be rotatable about the longitudinal axis of the compressing mechanism 10 relative the funnel-shaped area 13. On the other hand, the clamping jaws 11.1 to 11.6 provided in clamping area 14 are connected to the funnel-shaped area 13, as can be seen in the FIG. 9a representation. Accordingly, the clamping area 14 is also configured to be rotatable relative the clamping jaws 11.1 to 11.6.

Figure 8:
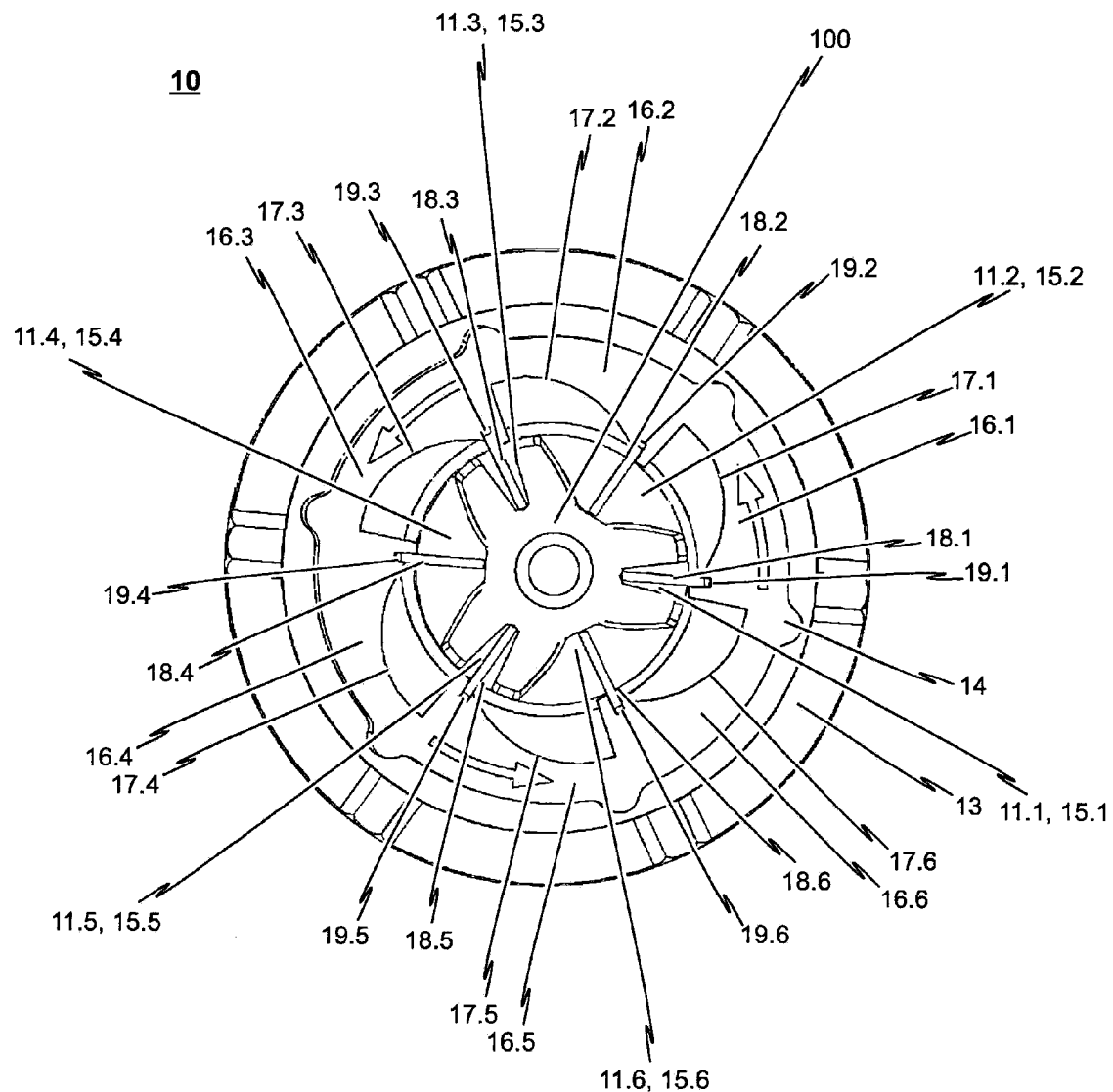
FIG. 8 a top plan view of the compressing mechanism shown in FIG. 7.

It can be noted from the top plan view of compressing mechanism 10 shown in FIG. 8 that the clamping area 14 is configured as a body similar to a hollow cylinder, whereby the wall thickness of the hollow cylinder-like body varies along its periphery at least in one area of the clamping area 14. The individual clamping jaws 11.1 to 11.6 are thereby positioned on the internal lateral surfaces of clamping area 14 such that by a rotating of clamping area 14 relative clamping jaws 11.1 to 11.6, the respective clamping jaws 11.1 to 11.6 will be moved—in dependence on the wall thickness of the hollow cylinder-like body in the respective contact areas with clamping jaws 11.1 to 11.6—in the radial direction.

The functioning of the compressing mechanism 10 used in the first exemplary embodiment of device 1 will be described in greater detail in the following referencing the representations provided in FIGS. 6 and 7. Specifically, FIG. 6 shows the compressing mechanism 10 in a perspective view, whereby the (only schematically-depicted) stent 100 is at least partly accommodated in the clamping area 14 of compressing mechanism 10. FIG. 6 shows the stent 100 in a state in which no compression has yet been effected by the clamping area 14 of the compressing mechanism 10.

In detail, it can be noted from the FIG. 6 representation that the respective clamping jaws 11.1 to 11.6 are only provided at the upper area of clamping area 14; i.e. in the area of clamping area 14 situated opposite the funnel-shaped area 13 of compressing mechanism 10. By providing the clamping jaws 11.1 to 11.6 at the upper area of clamping area 14, the entire stent 100 as a whole is not compressed, but instead only the end section of the stent 100 positioned at the height of the clamping jaws 11.1 to 11.6 in the accommodated state as shown in FIG. 6.

The individual clamping jaws 11.1 to 11.6 are preferably configured such that they exhibit a relative large contact surface 15 over which the radial compressive force from clamping jaws 11.1 to 11.6 is exerted on the outer surface of the stent 100 in the compressing of stent 100.

If the clamping area 14—starting from the state as shown in FIG. 6—is now rotated relative the funnel-shaped area 13 and thus relative the clamping jaws 11.1 to 11.6 in the direction of the arrow, the individual clamping jaws 11.1 to 11.6 will be radially pressed in the direction of the longitudinal axis of the compressing mechanism 10. This is to be attributed to the clamping jaws 11.1 to 11.6 being guided along the inner lateral surfaces of clamping area 14 by the rotating of clamping area 14 relative clamping jaws 11.1 to 11.6.

In detail, the compressing mechanism 100 employed in the first exemplary embodiment of the device 1 provides a respective grooved guide 16.1-16.6 for each clamping jaw 11.1 to 11.6, whereby the respective transfer functions of grooved guides 16.1-16.6 are determined by the course taken by the respective guiding surfaces 17.1-17.6 provided for clamping jaws 11.1 to 11.6. The respective clamping jaws 11.1 to 11.6 are forcibly driven along guiding surfaces 17.1-17.6 of the respective grooved guides 16.1-16.6 upon clamping area 14 being rotated relative to the clamping jaws 11.1 to 11.6.

The respective grooved guides 16.1-16.6 are thereby selected such that a transfer function is realized upon clamping area 14 being rotated relative the clamping jaws 11.1 to 11.6 which effects a movement of clamping jaws 11.1 to 11.6 in the radial direction.

Figure 7:
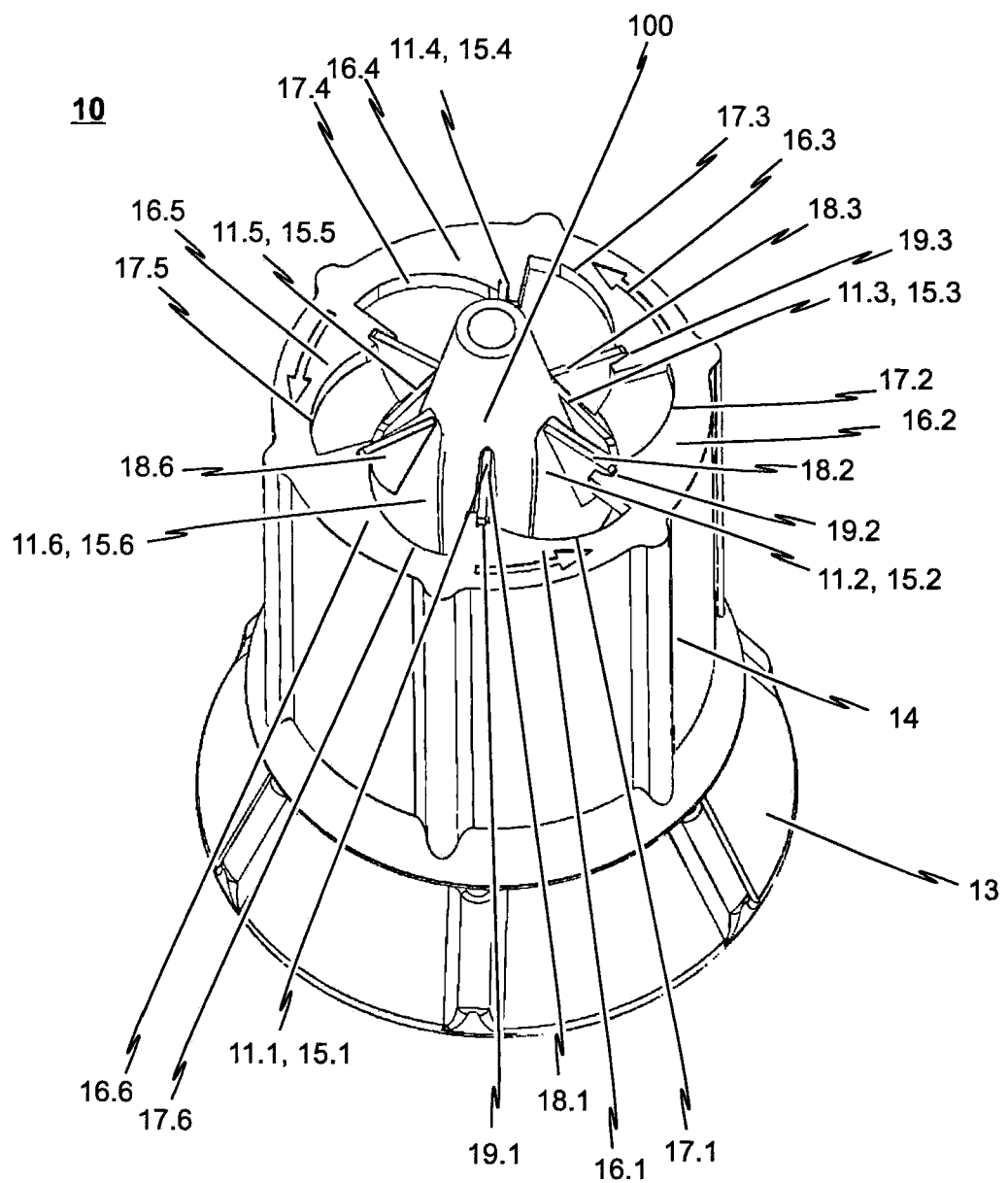
FIG. 7 a perspective view of the compressing mechanism used in the first exemplary embodiment of the disclosed device for compressing a stent with a stent at least partly accommodated therein after the compressing of the stent in the compressing mechanism.

FIG. 7 shows the compressing mechanism 10 depicted in FIG. 6 in a state in which the respective clamping jaws 11.1 to 11.6 are positioned in the area of the corresponding grooved guides 16.1-16.6 in which the clamping jaws 11.1 to 11.6 are moved in the radial direction on the longitudinal axis of compressing mechanism 100 by the rotating of clamping area 14 relative the clamping jaws 11.1 to 11.6. As can be noted in particular from FIG. 6, the guide webs 18.1-18.6 of the respective clamping jaws 11.1 to 11.6, guided along the guiding surfaces 17.1-17.6 upon the rotating of clamping area 14 relative clamping jaws 11.1 to 11.6, engage in the corresponding stops 19.1-19.6. The engaging of guide webs 18.1-18.6 in the respective stops 19.1-19.6 completes the radial movement of clamping jaws 11.1 to 11.6 in the direction of the longitudinal axis of compressing mechanism 10.

The compressing mechanism 10 depicted in the drawings makes use of a total of six clamping jaws 11.1 to 11.6 to transfer the compressive force acting radially on the lateral surface of stent 100 as evenly as possible during the compressing of stent 100.

The contact surfaces 15.1-15.6 of clamping jaws 11.1 to 11.6 are moreover designed to encompass large areas so as to avoid stress peaks during the transfer of the radially acting compressive force so that unnecessary stressing and possibly damaging of the stent 100 can be prevented during its compression.

The present disclosure is not limited to the clamping mechanism as described above with reference to the representations of FIGS. 6 to 9a/9b. It is also conceivable, for example, to use a clamping chuck-like mechanism in which a tensioning screw is provided in the clamping area 14 which is rotatable or movable about the longitudinal axis of the compressing mechanism 10 relative the clamping jaws 11.1 to 11.6 and which interacts with the clamping jaws 11.1 to 11.6 such that upon the tensioning screw being rotated or moved, the clamping jaws 11.1 to 11.6 are displaced in the longitudinal direction of the compressing mechanism 10 relative a clamping cone accommodated in clamping area 14. By the clamping jaws 11.1 to 11.6 moving into the clamping cone, the clamping jaws 11.1 to 11.6 are thereby moved in the radial direction.

A preferred use of the above described first exemplary embodiment of device 1 will be described in the following referencing the representations shown in FIGS. 10a to 10f. It will specifically be described how the device 1 provides a reliable way for a stent 100 to be transformed from its expanded state into a compressed state.

Figure 10A:
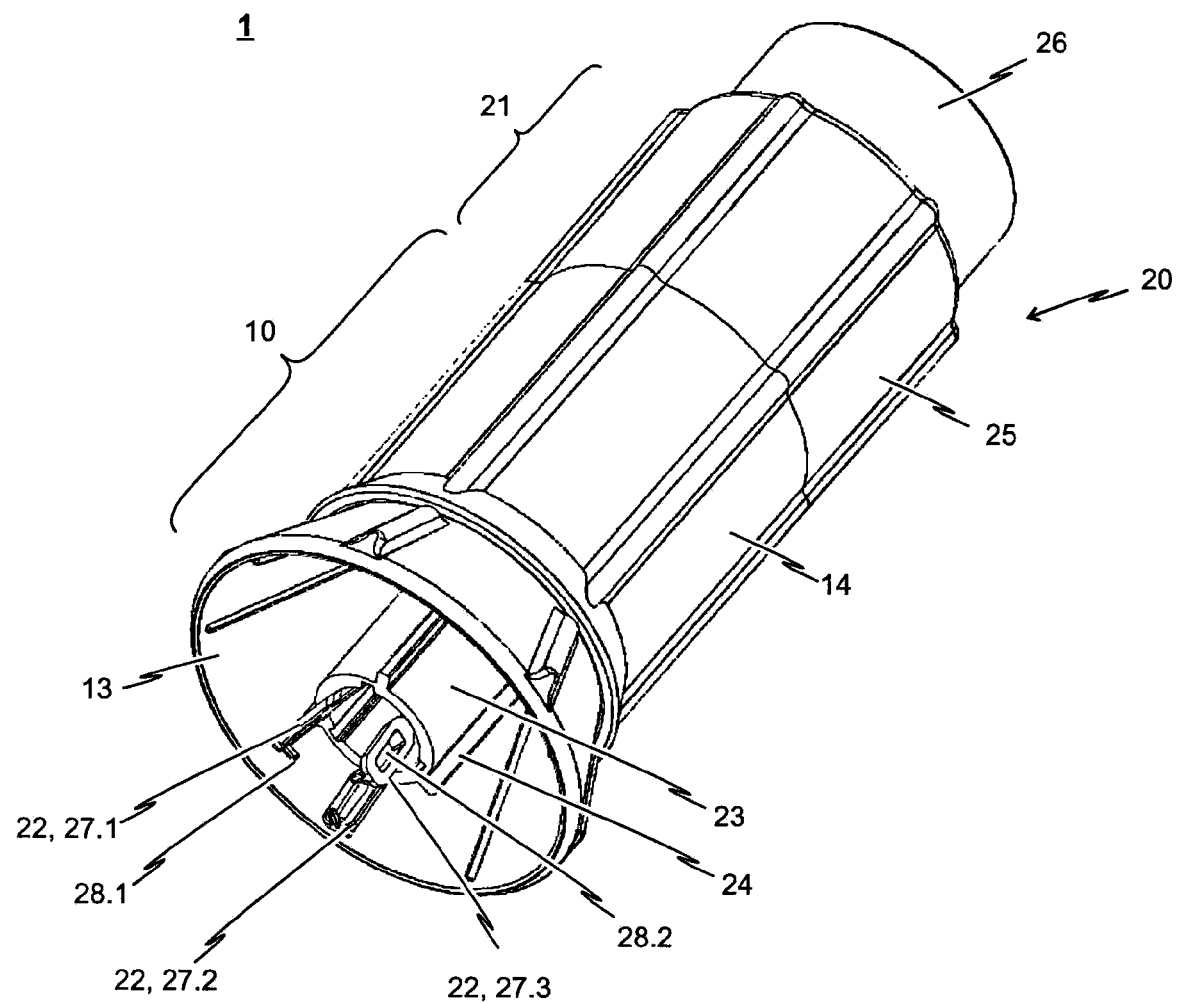
FIG. 10a-f perspective views of the first exemplary embodiment of the disclosed device illustrating the functioning during the compression of a stent.

FIG. 10a depicts the device 1 in its initial state as described above referencing the representations shown in FIG. 1 to FIG. 9b. In order to be able to compress the stent from its given expanded state with the device 1 shown in FIG. 10a in a defined manner pursuant a predefinable sequence of events, the actuating element 21 of gripping mechanism 20 is first actuated by pressing pushbutton 26. As already described especially in conjunction with FIGS. 3 to 5, the claw 22 of gripping mechanism 20 is at least partly driven out of the guide sleeve 23 upon the actuating of actuating element 21 so that the gripper arms 27.1, 27.2, 27.3 span outward like an umbrella (cf. FIG. 10b). Upon the actuating of actuating element 21, the gripping area of claw 22 amounts to e.g. 30 mm so as to accommodate stents up to an external diameter of 30 mm.

Figure 10B:
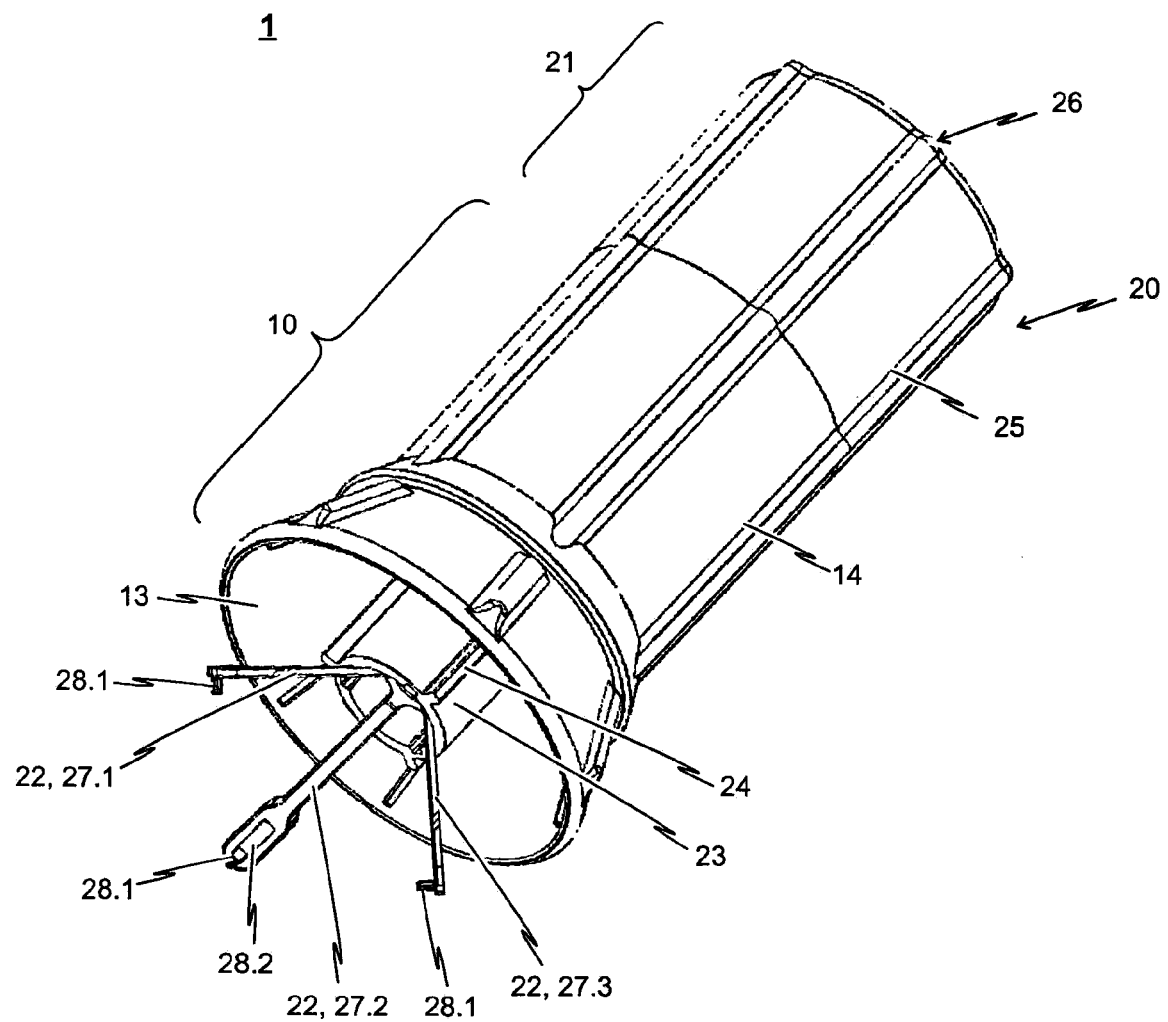
Figure 10C:
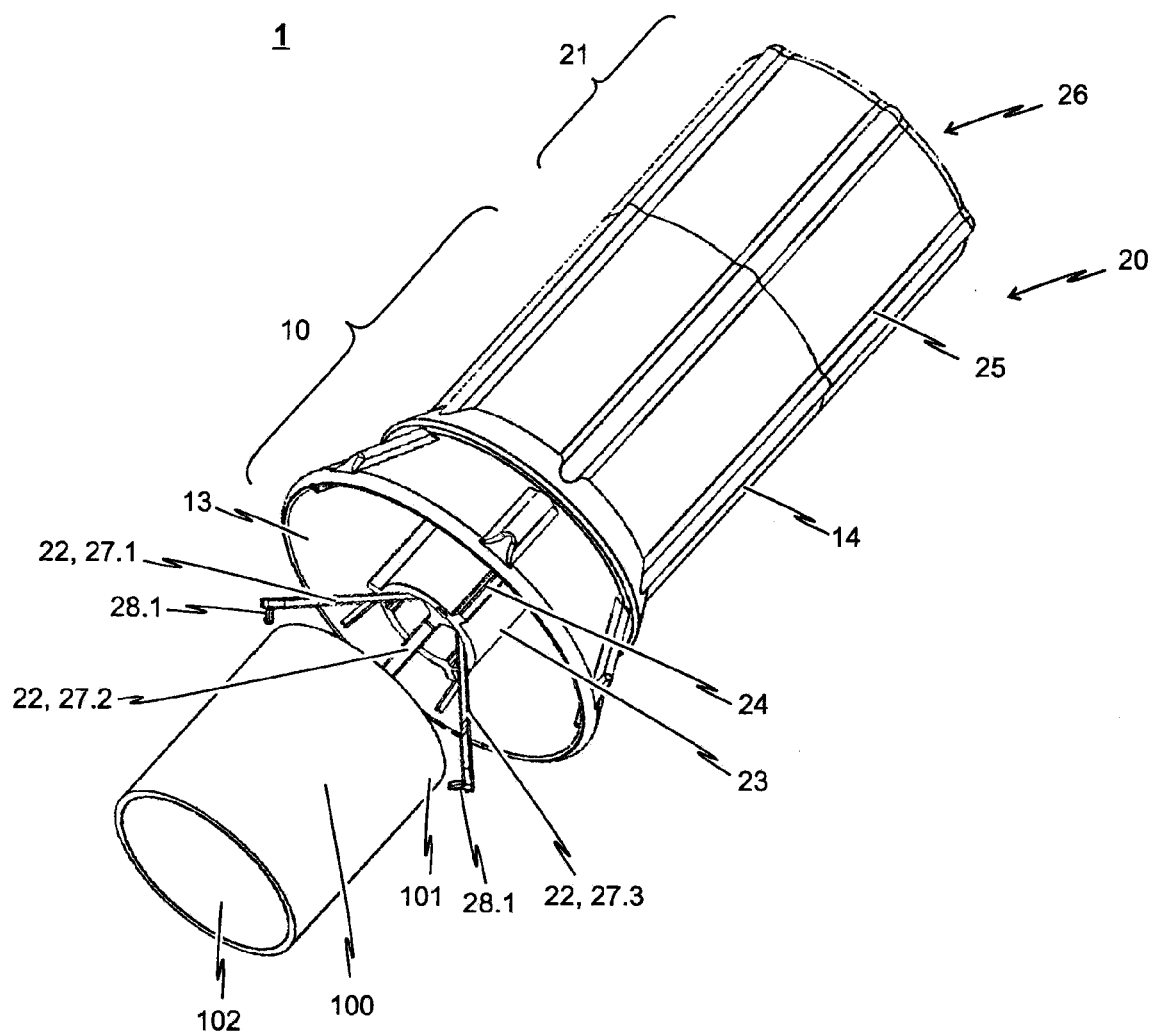

FIG. 10c shows how a stent 100 to be compressed can be grasped by the claw 22 extending partly from the guide sleeve 23. It is hereby to be assumed that the fastening means 28.1, 28.2 provided at the end section of gripper arms 27.1, 27.2, 27.3 are releasably connected to a retaining section provided at the upper end section 101 of the stent 100 to be compressed. It is hereby conceivable, for example, for the fastening means 28.1, 28.2 of gripper arms 27.1, 27.2, 27.3 to form a releasable engagement with corresponding retaining elements of the stent 100 to be compressed.

Figure 10D:
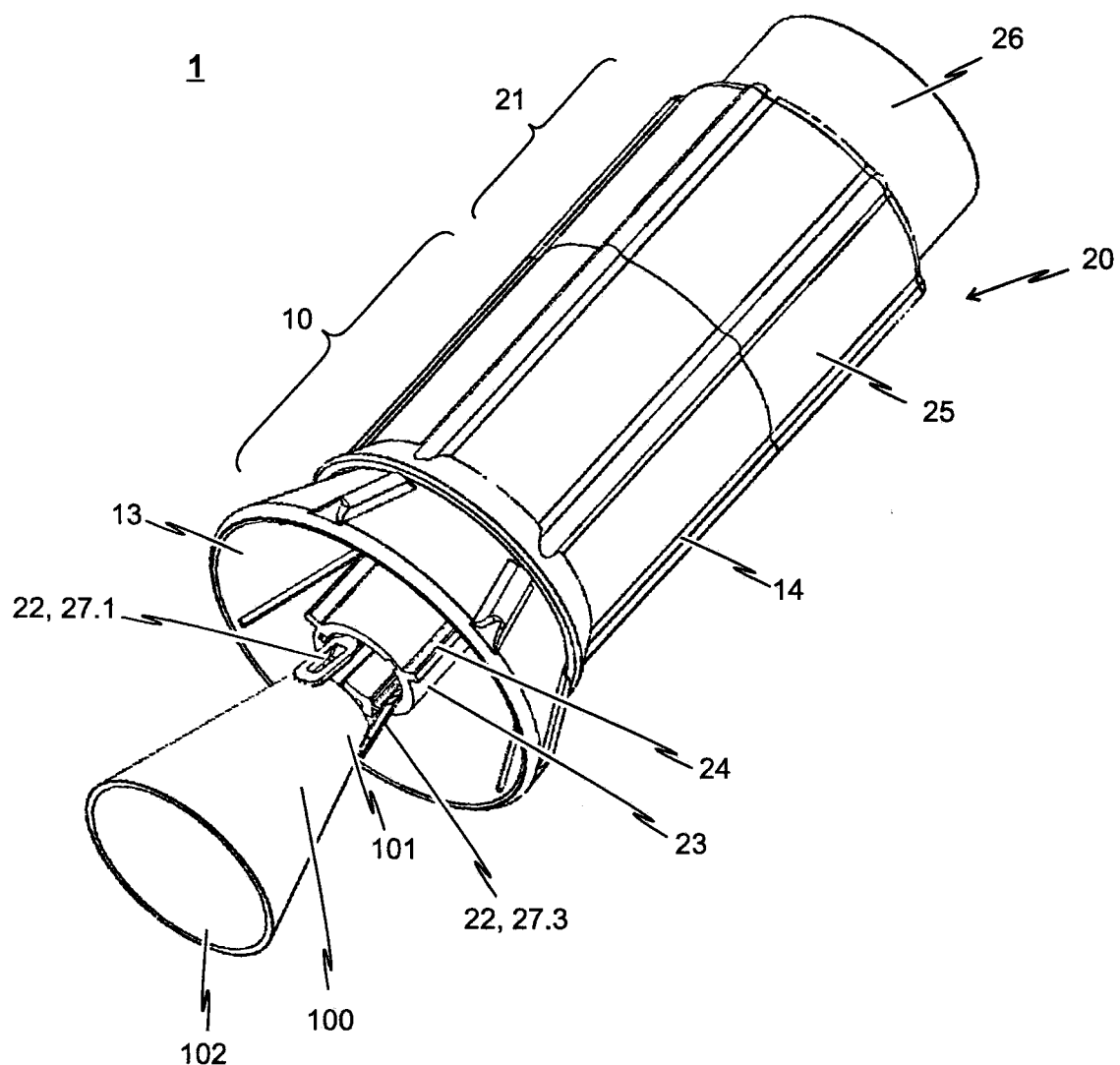

After the claw 22 is connected to the upper end section 101 of stent 100 via the fastening means 28.1, 28.2 of gripper arms 27.1, 27.2, 27.3, the pushbutton 26 of actuating element 21 is released—as shown in FIG. 10d—so that external compressive force is no longer exerted on pushbutton 26. Due to the pretensioning exerted on pushbutton 26 by the spring 31 of the spring mechanism, the claw 22 together with the stent 100 affixed to the claw 22, to the respective gripper arms 27.1, 27.2, 27.3 respectively, is pulled toward the funnel-shaped area 13 of the compressing mechanism 10 when pushbutton 26 is released. Since the gripper arms 27.1, 27.2, 27.3 are radially pulled in together with this movement, a precompressing of at least the upper end section 101 of stent 10 already occurs in the state as depicted in FIG. 10d.

Figure 10E:
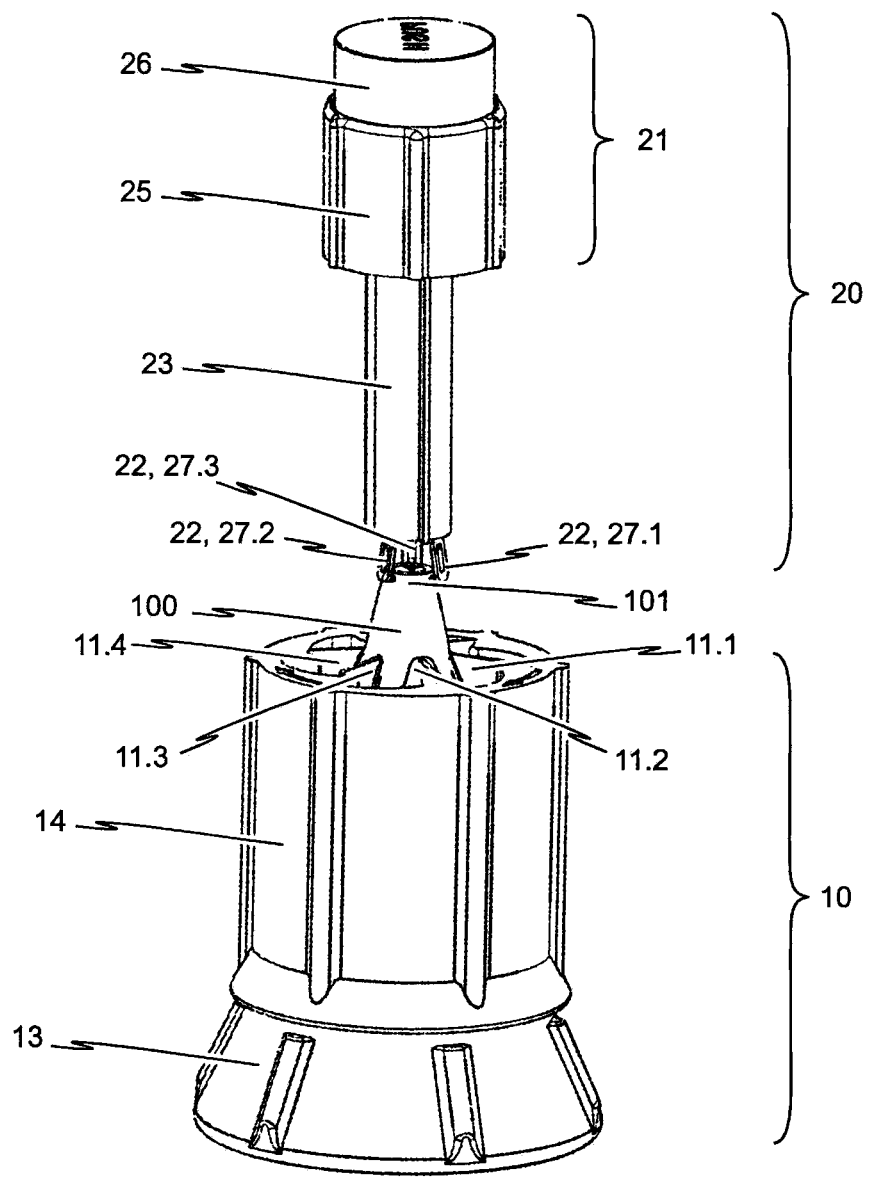

Subsequently, as shown in FIG. 10e, the gripping mechanism 20 together with the stent 100 connected to said gripping mechanism 20 is moved relative the compressing mechanism 10 such that the stent 100 is at least partly accommodated inside the compressing mechanism 10. Specifically, the upper end section 101 of the stent 100 may in an exemplary arrangement protrude from the upper opening of the compressing mechanism 10 by about 10.0 mm.

Figure 10F:
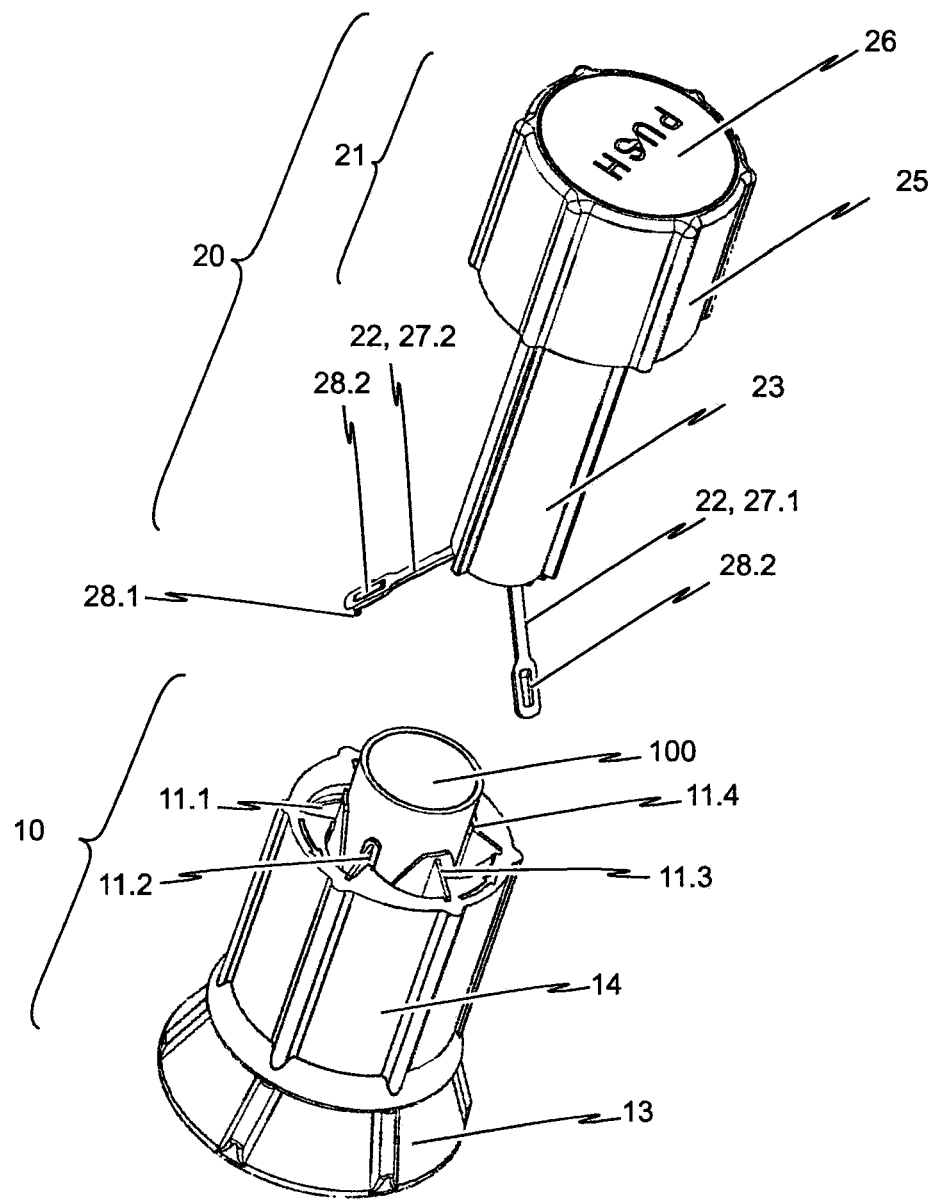

After the stent 100 is received in the compressing mechanism 10, the connection between the claw 22 of gripping mechanism 20 and the upper end section 101 of the stent 100 is again disengaged—as can be seen in the representation according to FIG. 10f. To this end, the pushbutton 26 of the actuating element 21 is pressed so that the claw 22 with the gripper arms 27.1, 27.2, 27.3 is driven at least partly out of the guide sleeve 23 and the gripper arms 27.1, 27.2, 27.3 spread out radially, in consequence of which the connection to the upper end section 101 of the stent 100 is disengaged.

The stent 100 thus inserted into the compressing mechanism 10 can now be compressed to the desired diameter, and in fact done so by the clamping area 14 being rotated relative to the funnel-shaped area 13 such that the clamping jaws 11.1 to 11.6 exert a radial compressive force on at least one area of the lateral surface of the stent 100 accommodated in the compressing mechanism 10. How the stent 100 can specifically be compressed within compressing mechanism 10 has already described with reference to FIGS. 6 to 9*a*.

Reference will be made in the following to the drawings depicted in FIGS. 12 to 18 in describing a second exemplary embodiment of a device 1*a* for compressing a stent 100 according to the present invention.

Elements in FIGS. 12 to 18 that are generally similar to previously described elements have the same reference numbers compared with the reference numbers in FIGS. 1 to 10 previously used for the similar elements.

The second exemplary embodiment of the inventive device 1a for compressing a stent 100 is characterized in that, during compression of the stent 100 accommodated within a compressing mechanism 10*a* of the device 1*a*, only a slight movement of the inner surface of the clamping means relative to the surface of the stent 100 in circumferential direction occurs thereby reducing any friction between the compressing mechanism 10*a* on the one hand and the stent 100 on the other hand.

Figure 12:
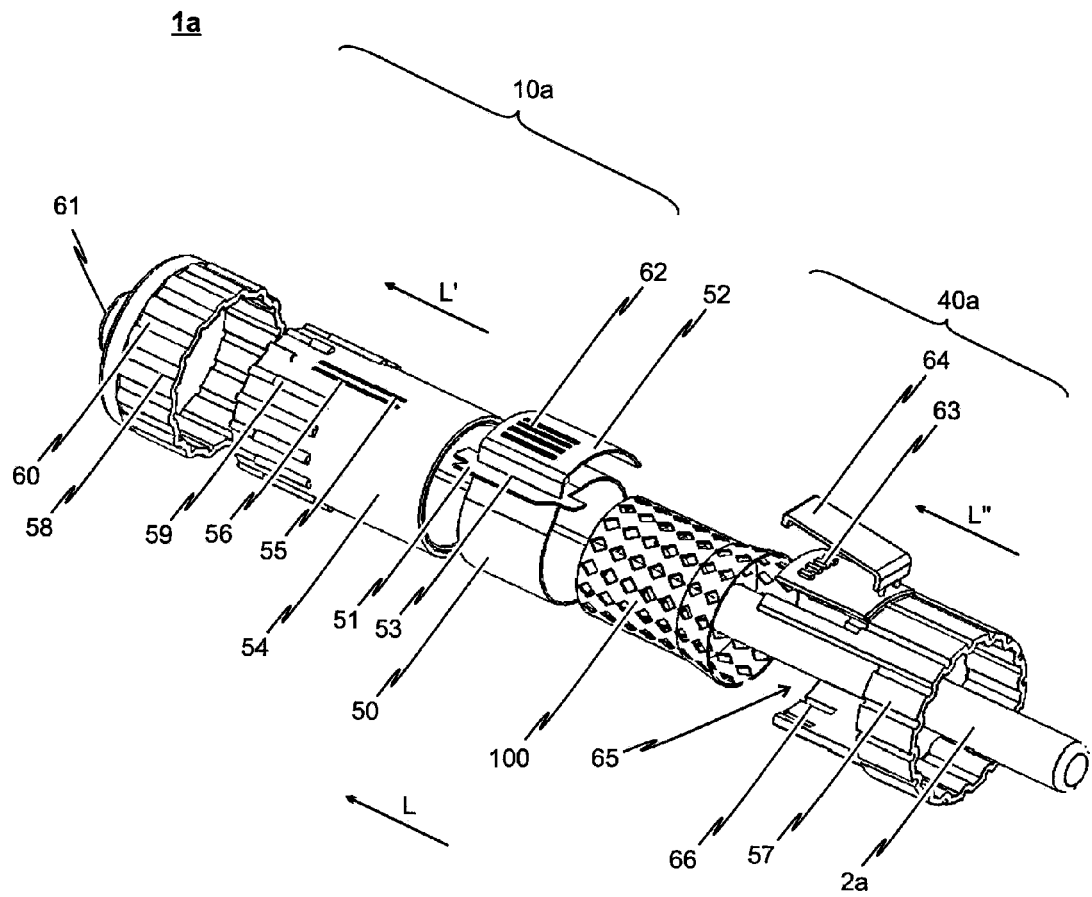
FIG. 12 a perspective view of a second exemplary embodiment of the disclosed device for compressing a stent, wherein the device is shown in an exploded state.
Figure 13:
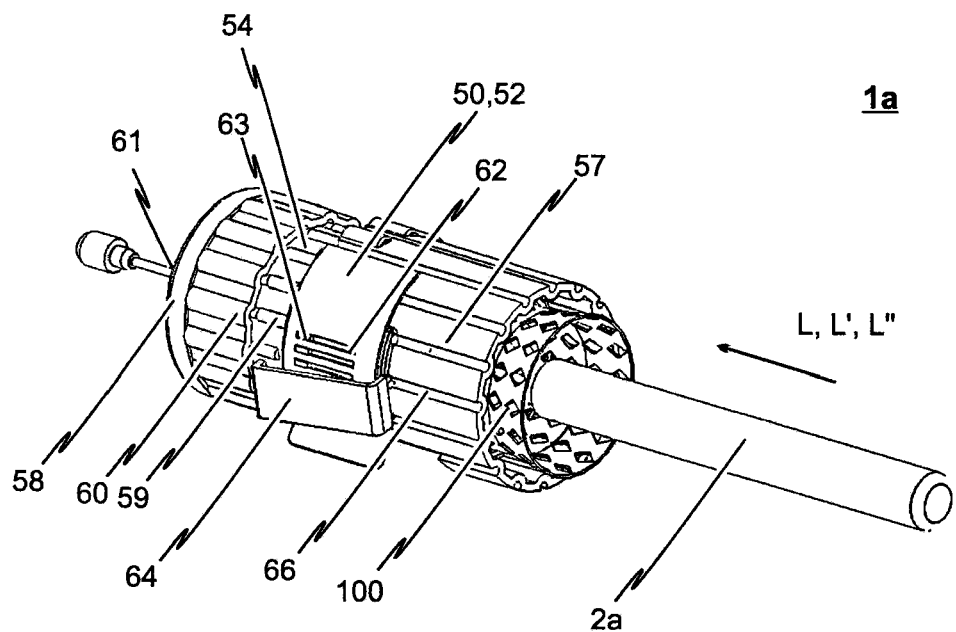
FIG. 13 a perspective view of the second exemplary embodiment of the device for compressing a stent, wherein the device is shown in its assembled condition with a stent at least partly accommodated in the compressing mechanism of the device prior to compressing the stent.

In particular, FIG. 12 shows a perspective view of the second exemplary embodiment of the disclosed device 1*a* for compressing a stent 100, wherein the device 1*a* is shown in an exploded state. FIG. 13 shows a perspective view of the second exemplary embodiment of the device 1*a*, wherein the device 1*a* is shown in its assembled condition with a stent 100 at least partly accommodated in the compressing mechanism 10*a* of the device 100 prior to compressing the stent 100.

Figure 14:
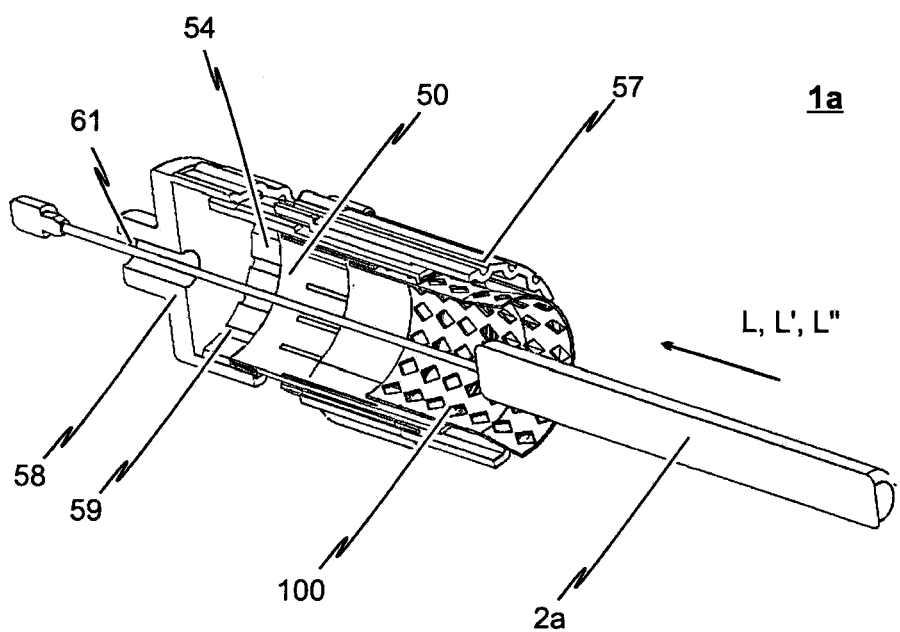
FIG. 14 a sectional view of the device depicted in FIG. 13 with a stent partly accommodated in the compressing mechanism of the device according to the second exemplary embodiment.

FIG. 14 shows a sectional view of the device 1*a* depicted in FIG. 13 with a stent 100 partly accommodated in the compressing mechanism 10*a* of the device 1*a*.

As shown, the second exemplary embodiment of the disclosed device 1*a* comprises a compressing mechanism 10*a*, within which a stent 100 to be compressed can be at least partly accommodated. The compressing mechanism 10*a* utilized in the second exemplary embodiment of the device 1*a* comprises an externally manipulatable clamping means 50 and is designed so as to exert a compressive force in radial direction on at least parts of a stent 100 which is accommodated within the compressing mechanism 10*a* such that the cross-section of the stent 100 is reduced to a predefinable value at least at certain areas.

The second exemplary embodiment of the disclosed device 1*a* further comprises a manipulating mechanism 40*a* for manipulating the clamping means 50. As described hereinafter in detail, the manipulating mechanism 40*a* is movable relative to the compressing mechanism 10*a* in order to move the clamping means 50 in the radial direction to adjust the internal cross-sectional diameter of the compressing mechanism 10*a*.

Figure 18:
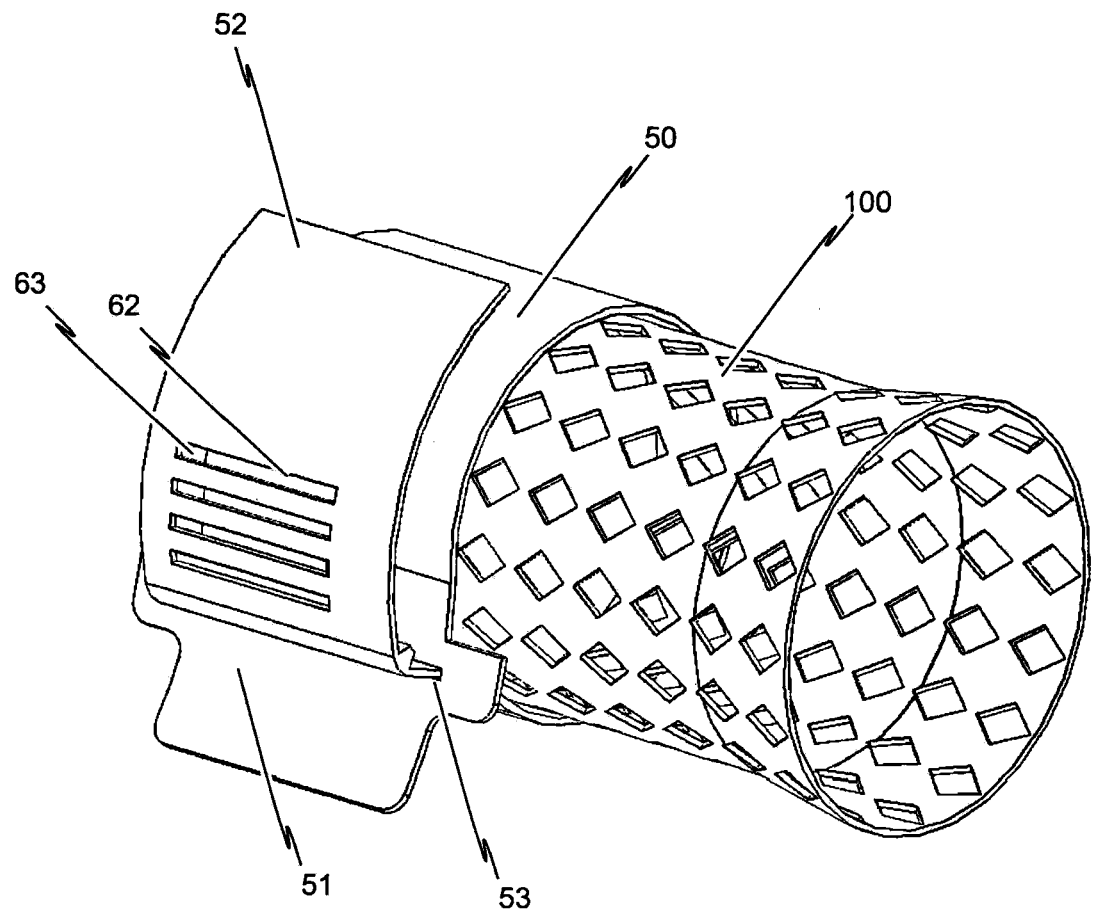
FIG. 18 a perspective view of a flat strip which serves as clamping means in the second exemplary embodiment of the device for compressing a stent, wherein a stent is partly accommodated in the compressing mechanism of the device.

According to the second exemplary embodiment of the disclosed device 1*a*, the clamping means 50 is realized in a strip-like configuration, and preferably as a flat strip. FIG. 18 is a perspective view of such a flat strip 50 which may serve as clamping means in the second exemplary embodiment of the device 1*a* for compressing a stent. As shown, the flat strip 50 has a looped configuration such as to form a clamping noose within which a stent 100 to be compressed can be accommodated. In the illustration according to FIG. 18, a stent 100 is partly accommodated in clamping noose formed by the looped strip 50.

The clamping noose formed by the looped strip 50 is accommodated in the compressing mechanism 10*a* of the device 1*a* according to the second exemplary embodiment.

The preferably flat strip 50 has a first end section 51 and an opposing second end section 52. To be seen in conjunction hereto from the representation provided in FIG. 12 is that the first end section 51 of the (preferably flat) strip 50 is looped such as to form a clamping noose, within which the stent 100 to be compressed can be at least partly accommodated. In this respect, reference is also made, for example, to FIG. 14 which shows a sectional view of the second exemplary embodiment of the device 1*a* with a stent 100 partly accommodated in the compressing mechanism 10*a* of the device 1*a*.

In detail and as shown, for example, in FIG. 12, according to the second exemplary embodiment of the disclosed device 1*a*, the first end section 51 of the preferably flat strip 50 comprises a slit 53 through which the second end section 52 of the preferably flat strip 50 is threaded in order to form the clamping noose, within which the stent 100 to be compressed can be at least partly accommodated.

Referring to FIG. 12 which shows the second exemplary embodiment of the disclosed device 1*a* in an exploded state, the compressing mechanism 10*a* of the device 1*a* according to the second exemplary embodiment may comprise an at least partly cylindrical housing part 54 within which the clamping noose formed by the preferably flat strip 50 is accommodated. This can also be recognized from the illustration depicted in FIG. 14 which is a sectional view of the device 1*a* according to the second exemplary embodiment.

As shown in FIG. 12, according to the second exemplary embodiment of the disclosed device 1*a*, the circumferential surface of the at least partly cylindrical housing part 54 is provided with a slit-like opening 55 through which at least the second end section 52 of the preferably flat strip 50 is threaded such that the clamping noose can be tightened when the second end section 52 of the preferably flat strip 50 is further pulled out from the slit-like opening 55.

In order to tighten the clamping noose when the second end section 52 of the strip 50 is further pulled out from the slit-like opening 55 provided in the circumferential surface of the at least partly cylindrical housing part 54, the first end section 51 of the flat strip 50 is fixed to the at least partially cylindrical housing part 54 of the compressing mechanism 10*a*. In this regard, it is preferred that the circumferential surface of the at least partly cylindrical housing part 54 is provided with an additional slit-like opening 56 through which the first end section 51 of the preferably flat strip 50 is threaded at least partly such as to clamp the first end section 51 of the preferably flat strip 50 and to fix the first end section 51 to the at least partly cylindrical housing part 54 of the compressing mechanism 10*a*.

Referring to FIG. 12, according to the second exemplary embodiment of the disclosed device 1*a* for compressing a stent 100, the manipulating mechanism 40*a* may comprise an at least partly hollow cylindrical body 57 having an inner diameter which is at least slightly larger than the outer diameter of the cylindrical housing part 54 of the compressing mechanism 10*a*. In this regard, the cylindrical housing part 54 of the compressing mechanism 10*a* is at least partly accommodatable within the at least partly hollow cylindrical body 57. In detail, the housing part 54 of the compressing mechanism 10*a* may comprise a first cylindrical end section adapted to engage with the at least partly hollow cylindrical body 57 of the manipulating mechanism 40*a*. In this respect, reference is also made to FIG. 17, which is a sectional view of the device 1*a* according to the second exemplary embodiment. In the illustration according to FIG. 17, a stent 100 is not accommodated in the compressing mechanism 10a of the device 1a. A perspective view of the device 1a depicted in a sectional view in FIG. 17 is shown in FIG. 15.

On the other hand, the housing part 54 of the compressing mechanism 50 may comprise an opposing second end section adapted to engage with a plain cover 58. As can be seen, for example, from FIG. 17, the plain cover 58 may have a cup-shaped configuration.

In addition, the second end section of the housing part 54 may comprise at least one engagement means 59, for example, in the form of dedicated grooves. In this regard, the plain cover 58 may be provided with at least one complementary engagement means 60 in order to block rotation of the plain cover 58 relative to the second section of the housing part 54 in an engaged state. In this regard, reference is made to FIG. 15 which is a perspective view of the second exemplary embodiment of the device 1a for compressing a stent 100 without a stent 100 accommodated in the compressing mechanism 10a of the device 1a.

Figure 15:
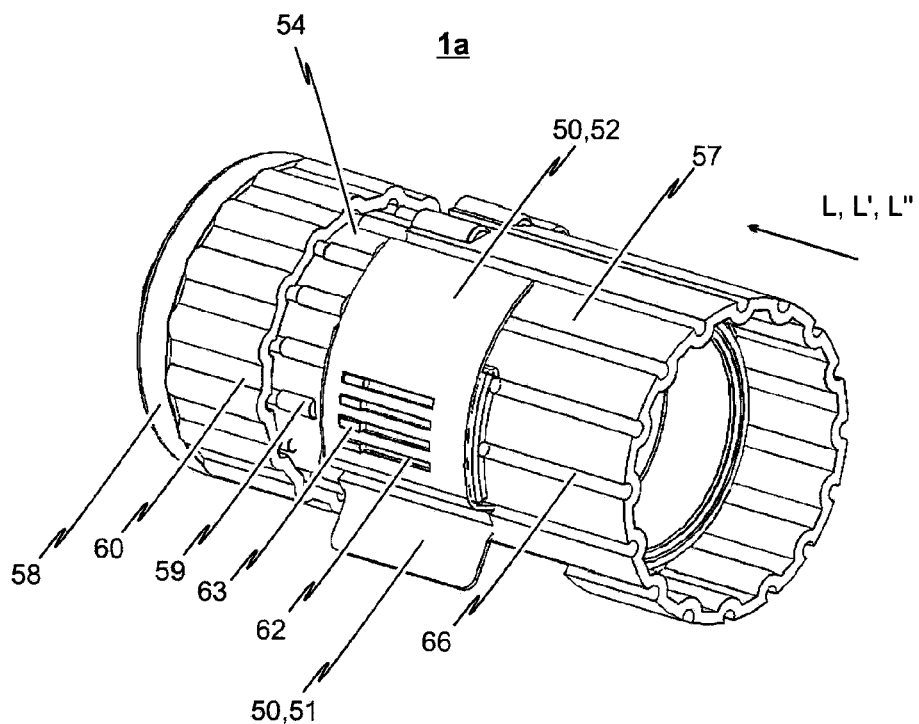
FIG. 15 a perspective view of the second exemplary embodiment of the device for compressing a stent without a stent accommodated in the compressing mechanism of the device and without any latching means affixed to the manipulating mechanism.
Figure 17:
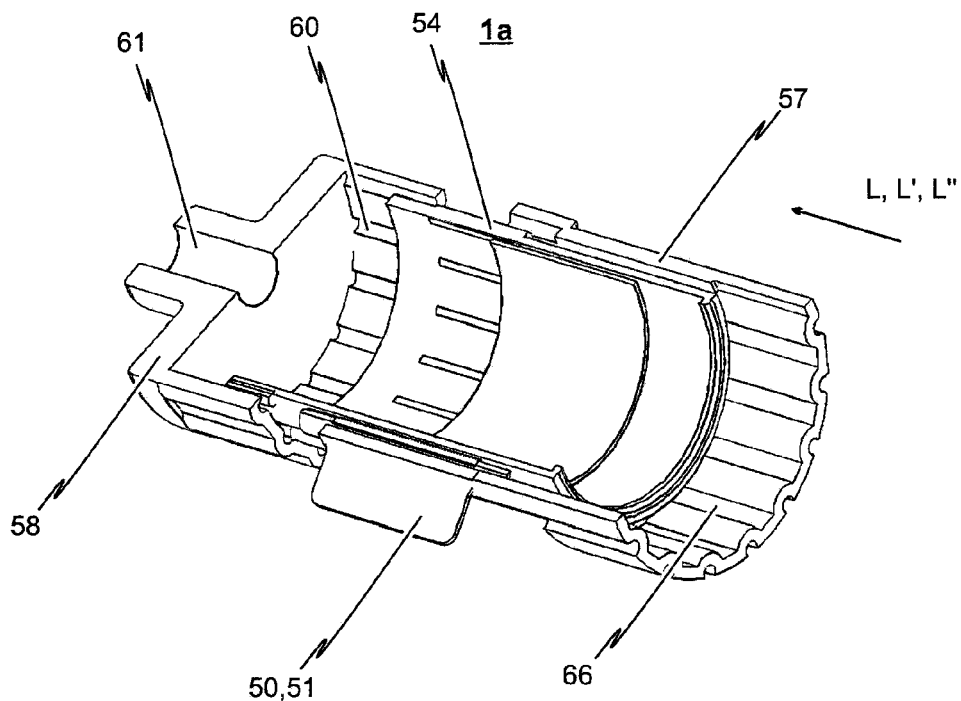
FIG. 17 a sectional view of the device depicted in FIG. 15.

Referring to FIG. 17, which is a sectional view of the second exemplary embodiment of the device 1a depicted in FIG. 15, the plain cover 58 may comprise a centered opening 61 aligned with the longitudinal axis L' of the housing part 54 of the compressing mechanism 10a. This centered opening 61 provided in the front face of the plain cover 58 may be used for removing a stent 100 from the compressing mechanism 10a after the stent 100 has been at least partly compressed in the compressing mechanism 10a.

Figure 34:
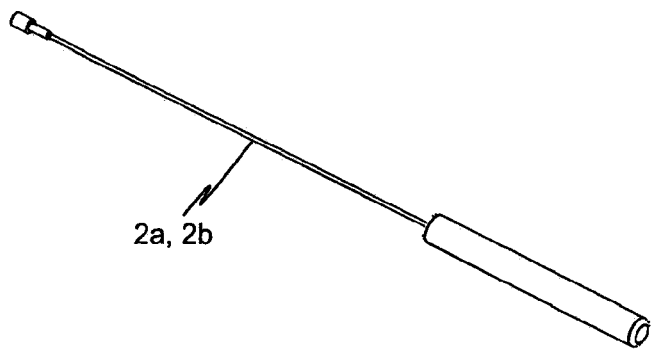
FIG. 34 a perspective view of a push rod which may be used, for example, for pushing an at least partly compressed stent from the second housing section to the third housing section of the housing part utilized in the compressing mechanism of the third exemplary embodiment of the disclosed device for compressing a stent.

For this purpose, a push rod 2a as depicted, for example, in FIG. 34 may be used for pushing the at least partly compressed stent 100 through the centered opening 61 provided in the face surface of the plain cover 58.

The device 1a according to the second exemplary embodiment comprises a manipulating mechanism 40a for manipulating the looped strip 50, wherein the manipulating mechanism 40a is movable relative to the compressing mechanism 10a in order to exert a compressive force acting in the radial direction on a stent accommodated in the compressing mechanism 10a so as to reduce the cross-section of the stent to a predefinable value. For this purpose, it is preferred that at least the second end section 52 of the preferably flat strip 50 is fasted to the manipulating mechanism 40a. According to the second exemplary embodiment of the device 1a, the second end section 52 of the preferably flat strip 50 may be provided with means for releasable fastening the second end section 52 of the strip 50 to the cylindrical body 57 of the manipulating mechanism 40a.

As can be seen from the illustration depicted, for example, in FIG. 15, the second end section 52 of the preferably flat strip 50 may be provided with at least one cutout 62 which is adapted to fit to a corresponding protruding segment 63 which is formed at the cylindrical body 57 of the manipulating mechanism 40a. In detail and as can be seen, for example, from FIG. 18, the at least one cutout 62 may extend essentially parallel to the longitudinal axis L' of the housing part 54 of the compressing mechanism 10a.

Figure 16:
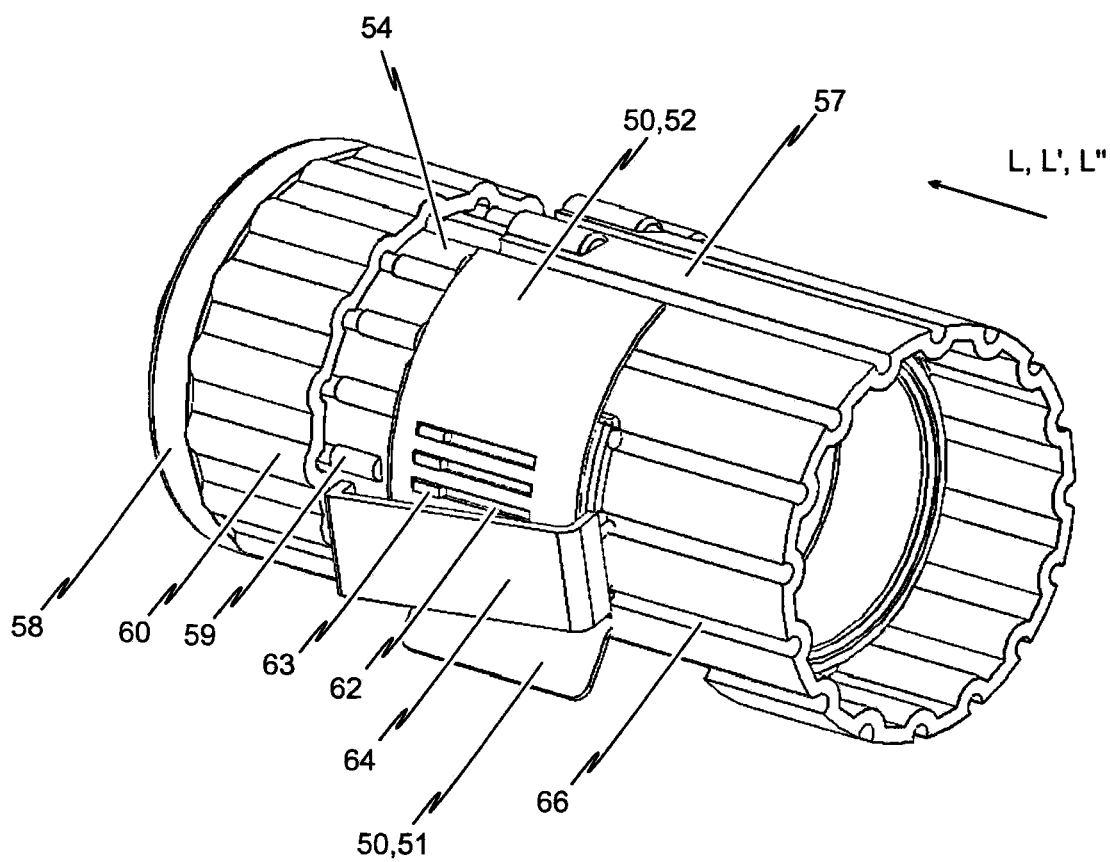
FIG. 16 a perspective view of the second exemplary embodiment of the device for compressing a stent without a stent accommodated in the compressing mechanism of the device, but with latching means affixed to the manipulating mechanism.

Reference is made to FIG. 16 which is a perspective view of the second exemplary embodiment of the device 1a for compressing a stent 100, wherein no stent 100 is accommodated in the compressing mechanism 10a of the device 1a. As shown, the second exemplary embodiment may comprise latching means 64 which are preferably releasable fixed to the cylindrical body 57 of the manipulating mechanism 40a in order to latch the second end section 52 of the preferably flat strip 50 onto the cylindrical body 57 of the manipulating mechanism 40a.

As can be seen from FIG. 12, according to the second exemplary embodiment of the disclosed device 1a, the manipulating mechanism 40a may have a cylindrical body 57, which may be provided with a window area 65. In the fully assembled state of the device 1a, within the window area 65 of the cylindrical body 57 the slit-like opening 55 of the housing part 54, through which at least the second end section 52 of the strip 50 is threaded, and the additional slit-like opening 56 of the housing part 54 are located.

Reference is made, for example, to FIG. 15, which shows a perspective view of the second exemplary embodiment of the device 1a for compressing a stent 100. Hence, the cylindrical body 57 of the manipulating mechanism 40a may be provided with at least one complimentary engagement means 66 in order to block rotation of the cylindrical body 57 of the manipulating mechanism 40a relative to the housing part 54 of the compressing mechanism 10a in an engaged state.

Briefly summarized, according to the second exemplary embodiment, the device 1a for compressing a stent 100 comprises housing part 54 which holds a preferably flat strip 50. The strip 50 is threaded through two slits 55, 56 provided in the housing part 54 and attached to a rotating cover, i.e. the partly hollow cylindrical body 57 of the manipulating mechanism 40a. The strip 50 may have at least one cutout 62 that allow it to fit to matching protruding segments 63 of the partly hollow cylindrical body 57 of the manipulating mechanism 40a, just like a regular closing belt.

The other side of the housing part 54 holds a non-rotating plain cover 58 for securing the stent 100 accommodated in the compressing mechanism 10a during the crimping process.

Finally, a push rod 2a may be used to advance the stent 100 in the final stage of its crimping. An exemplary embodiment of the push rod 2a is depicted in FIG. 34.

Operating of the device 1a according to the second exemplary embodiment is done as follows:

Firstly, the stent 100 to be compressed is loaded into the housing part 54 of the compressing mechanism 10a. Thereafter, the cylindrical body 57 of the manipulating mechanism 10a is aligned with respect to the housing part 54 and advanced while slightly rotating clockwise.

This rotation causes the preferably flat strip 50 accommodated in the housing part 54 of the compressing mechanism 10a to tighten, and thus to reduce the diameter of the clamping noose formed by the preferably flat strip 50 in its looped arrangement. The operator should then pullback the cylindrical body 57 of the manipulating mechanism 40a, rotate it again and push forward.

As already mentioned, the housing part 54 of the compressing mechanism 10a has protruding segments (engagement means 59) that can lock in place the cylindrical body 57 of the manipulating mechanism 40a.

Once the target diameter of the stent 100 accommodated in the compressing mechanism 10a of the device 1a was achieved, the operator can push the stent 100 using a push rod 2a and force it into the delivery catheter.

Reference will be made in the following to FIGS. 19 to 34 in describing a third exemplary embodiment of a device 1b for compressing a stent 100. Elements in FIGS. 19 to 34 that are generally similar to previously described elements have the same reference numbers compared with the reference numbers in FIGS. 1 to 10 and FIGS. 12 to 18 previously used for the similar elements.

Figure 19:
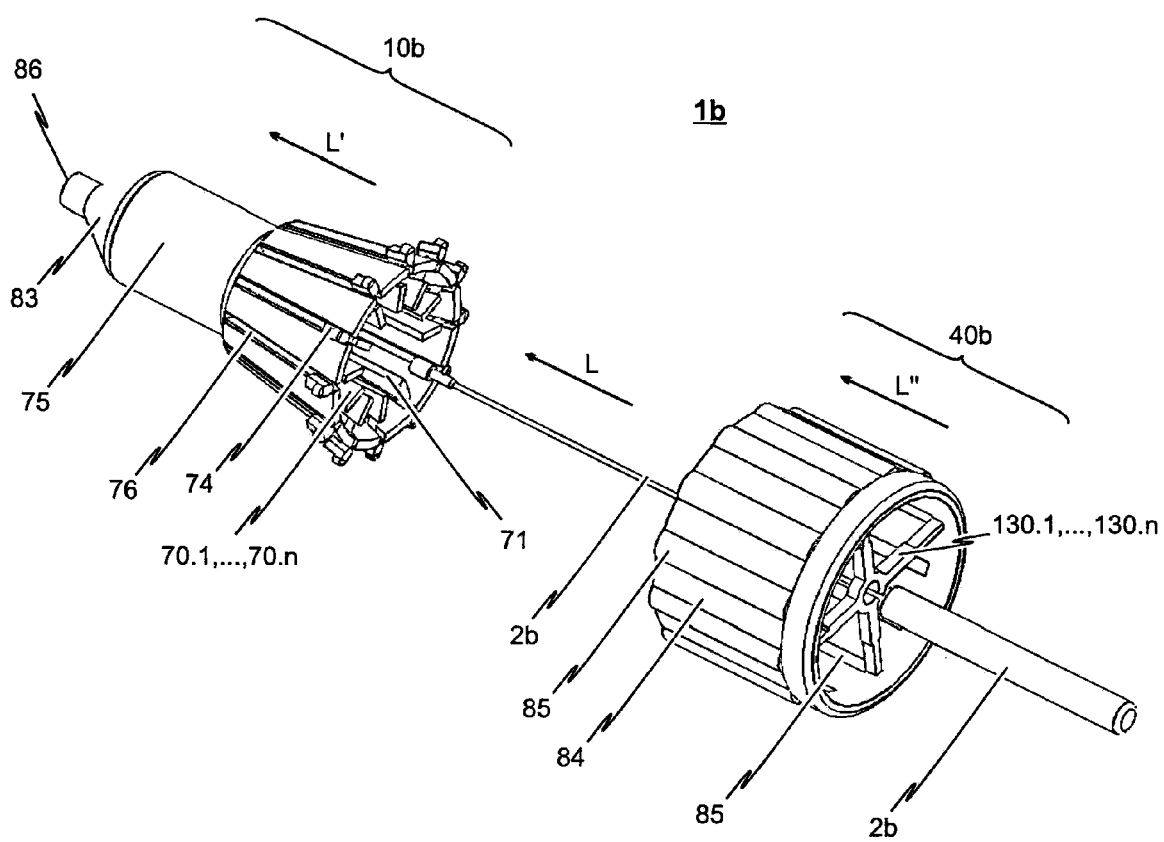
FIG. 19 a perspective view of a third exemplary embodiment of the disclosed device for compressing a stent, wherein the device is shown in an open state.
Figure 20:
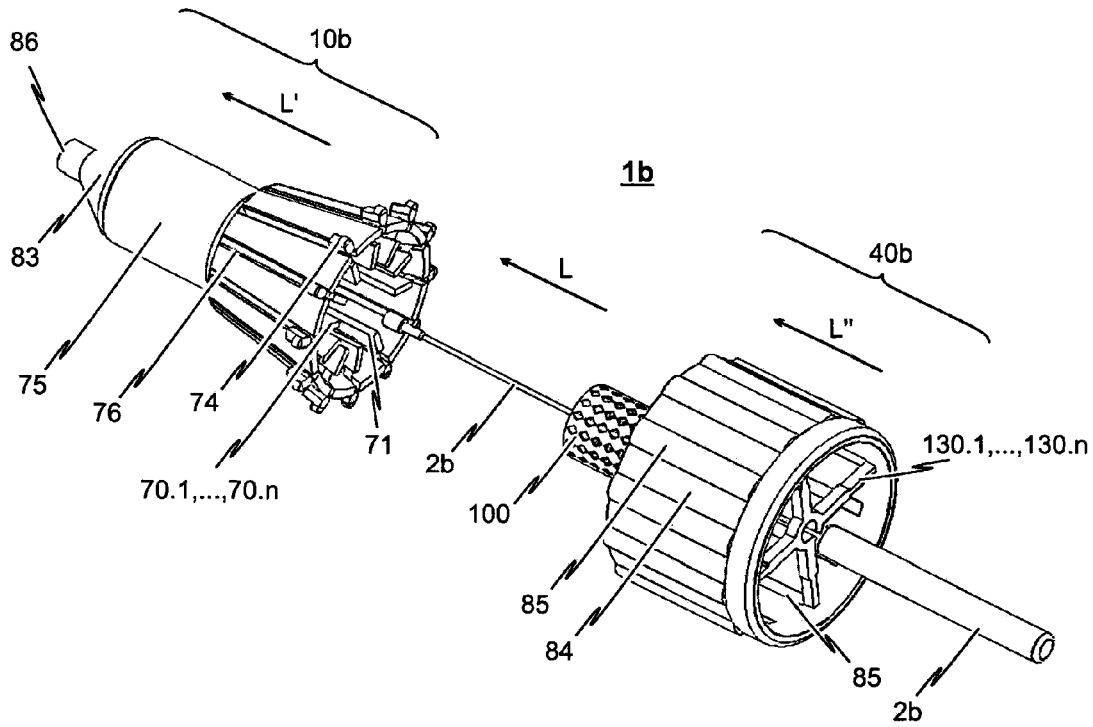
FIG. 20 a perspective view of the device depicted in FIG. 19 with a stent to be compressed.
Figure 21:
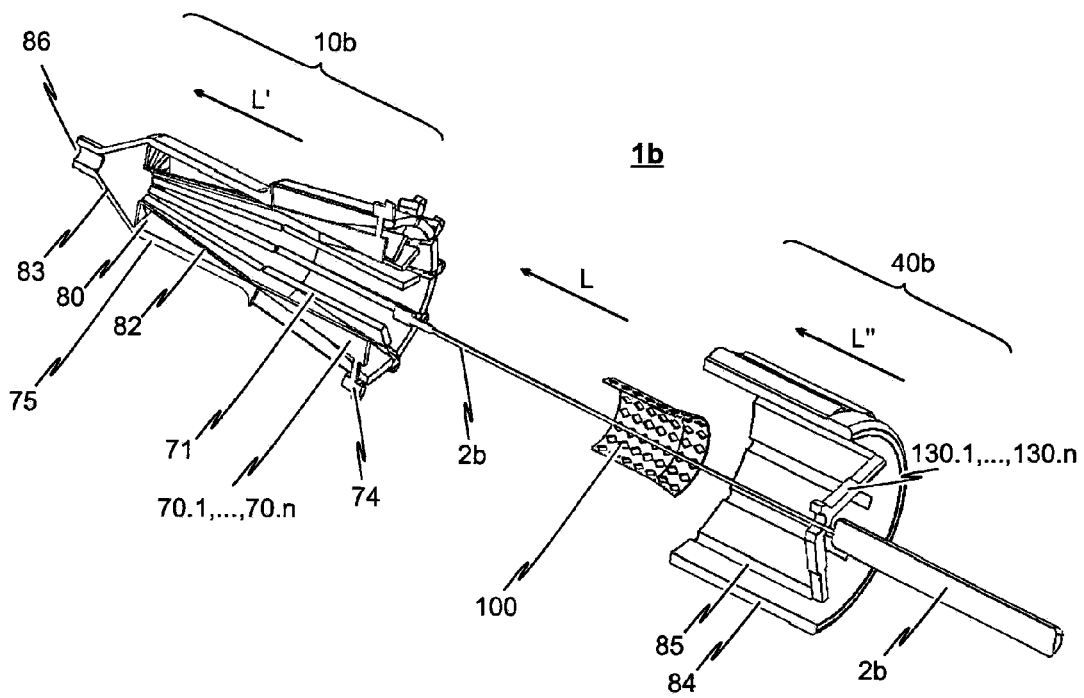
FIG. 21 a sectional view of the device depicted in FIG. 19 with a stent to be compressed.
Figure 22:
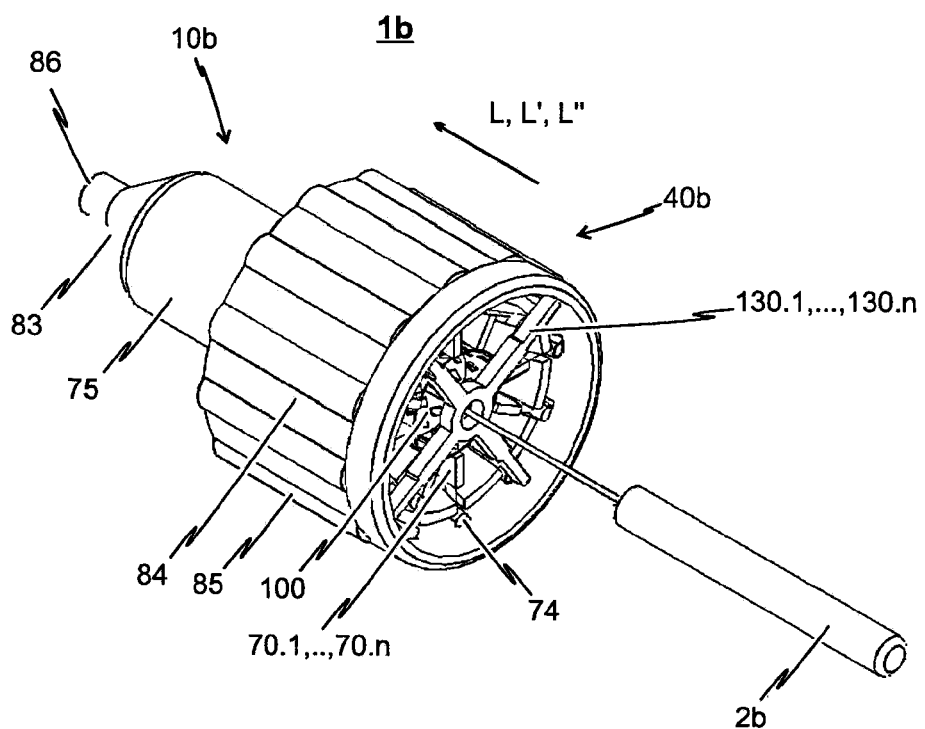
FIG. 22 a perspective view of the third exemplary embodiment of the disclosed device for compressing a stent with a stent to be compressed accommodated in the compressing mechanism of the device prior to compressing the stent, wherein the device of the third exemplary embodiment is shown in its closed state.
Figure 23:
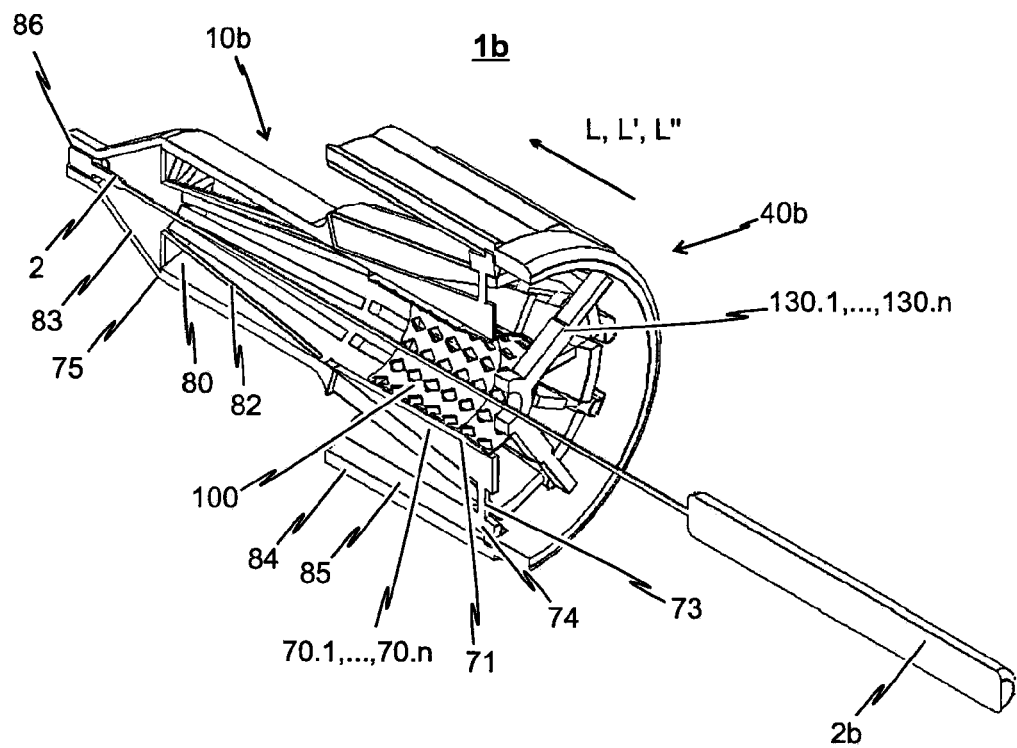
FIG. 23 a sectional view of the device depicted in FIG. 22 with a stent to be compressed accommodated in the compressing mechanism of the device prior to compressing the stent.

In detail, FIG. 19 shows a perspective view of the third exemplary embodiment of the disclosed device 1b for compressing a stent 100, wherein the device 1b is shown in an open state. FIG. 20 shows a perspective view of the device 1b depicted in FIG. 19 with a stent 100 to be compressed. A sectional view of the device 1b depicted in FIG. 19 with a stent 100 to be compressed is shown in FIG. 21. FIG. 22 shows a perspective view of the third exemplary embodiment of the device 1b with a stent 100 to be compressed accommodated in a compressing mechanism 10b of the device 1b prior to actual compressing the stent 100, wherein the device 1b is shown in its closed state. A sectional view of the device 1b depicted in FIG. 22 with a stent 100 to be compressed accommodated in the compressing mechanism 10b of the device 1b prior to actual compressing the stent 100 is shown in FIG. 23.

Figure 24:
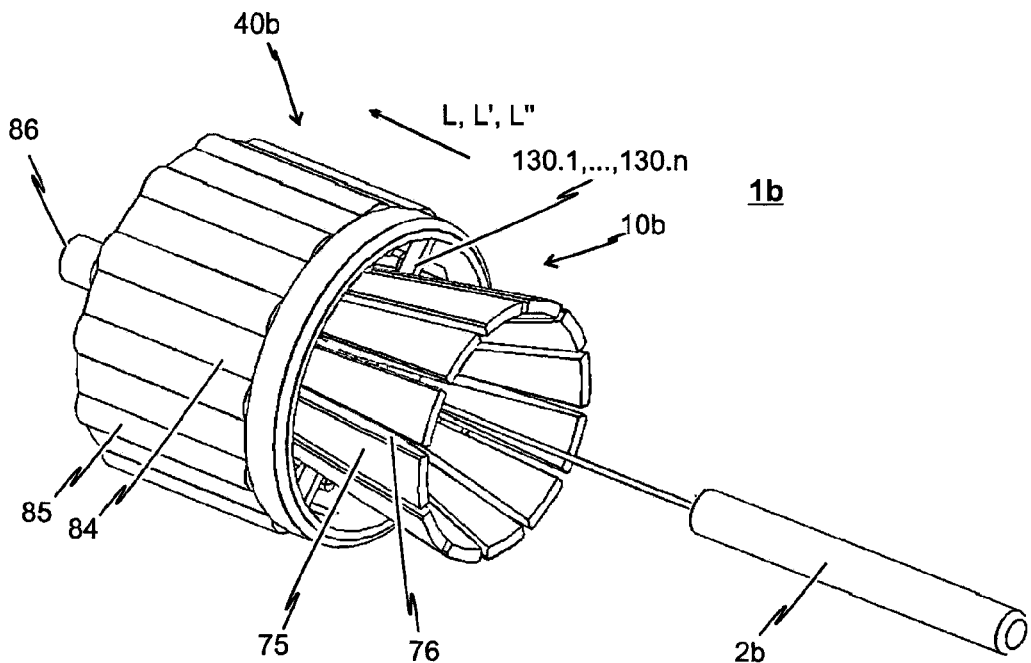
FIG. 24 a perspective view of the third exemplary embodiment of the disclosed device for compressing a stent with a stent accommodated in the compressing mechanism of the device after activation of the manipulating mechanism of the device.
Figure 25:
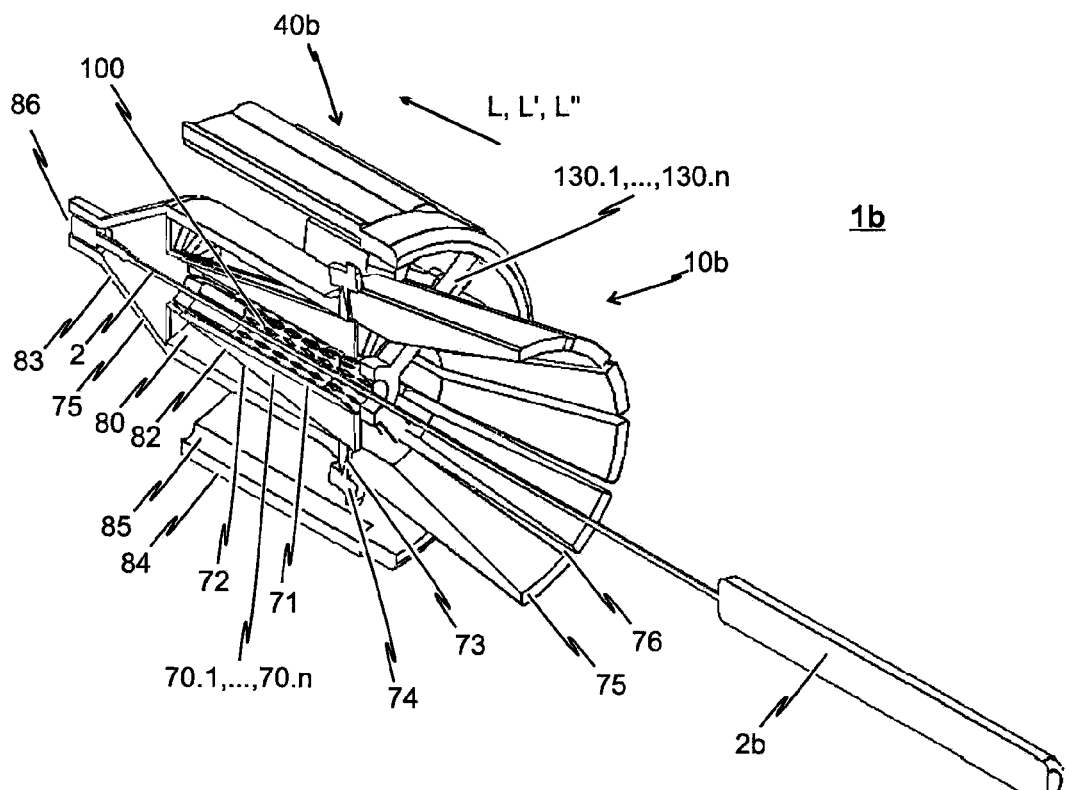
FIG. 25 a sectional view of the device depicted in FIG. 24 with an at least partly compressed stent accommodated in the compressing mechanism of the device after activation of the manipulating mechanism.

On the other hand, FIG. 24 shows a perspective view of the third exemplary embodiment of the disclosed device 1b for compressing a stent 100 with a stent 100 accommodated in the compressing mechanism 10b of the device 1b after activation of a manipulating mechanism 40b of the device 1b. A sectional view of the device 1b depicted in FIG. 24 with an at least partly compressed stent 100 accommodated in the compressing mechanism 10b of the device 1b after activation of the manipulating mechanism 40b of the device 1b is shown in FIG. 25.

Hence, the device 1b according to the third exemplary embodiment comprises a compressing mechanism 10b, within which a stent 100 to be compressed can be at least partly accommodated. The compressing mechanism 10b comprises externally manipulatable clamping means, which consist of a plurality of preferably wedge-shaped clamping jaws 70.1 to 70.n.

As will be described in the following, the compressing mechanism 10b of the device 1b according to the third exemplary embodiment is configured such as to exert a compressive force in radial direction on at least parts of a stent 100 accommodated within the compressing mechanism 10b such that the cross-section of the stent 100 can be reduced to a predefinable value at least at certain areas. For this purpose, the device 1b according to the third exemplary embodiment comprises a manipulating mechanism 40b for manipulating the clamping means, i.e. the plurality of preferably wedge-shaped clamping jaws 70.1 to 70.n.

In particular, the manipulating mechanism 40b of the device 1b according to the third exemplary embodiment is movable relative to the compressing mechanism 10b in order to move the preferably wedge-shaped clamping jaws 70.1 to 70.n in radial direction thereby adjusting the internal cross-sectional diameter of the compressing mechanism 10b.

Figure 33:
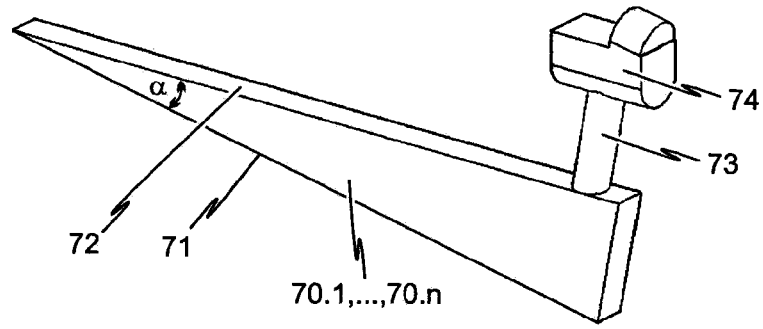
FIG. 33 a perspective view of a single wedge-shaped clamping jaw which serves as clamping means in the compressing mechanism utilized in the third exemplary embodiment of the disclosed device for compressing a stent.

Reference is made to FIG. 33 which is a perspective view of a single wedge-shaped clamping jaw. As already mentioned, a plurality of such wedge-shaped clamping jaws 70.1 to 70.n may serve as clamping means in the compressing mechanism 10b utilized in the third exemplary embodiment of the disclosed device 1b for compressing a stent 100.

Hence, each of the plurality of preferably wedge-shaped clamping jaws 70.1 to 70.n may have a wedge surface 71. In the fully assembled state of the compressing mechanism 10b of the device 1b according to the third exemplary embodiment, the preferably wedge-shaped clamping jaws 70.1 to 70.n are circumferentially arranged such that the respective wedge surfaces 71 encircle a cavity which serves as receptacle within which a stent 100 to be compressed can be at least partly accommodated. In this regard, reference is also made, for example, to FIG. 23 which is a sectional view of the third exemplary embodiment of the disclosed device 1b. In the illustration according to FIG. 23, a stent 100 to be compressed is at least partly accommodated in the compressing mechanism 10b of the device 1b prior to the actual compression of the stent 100.

Figure 28:
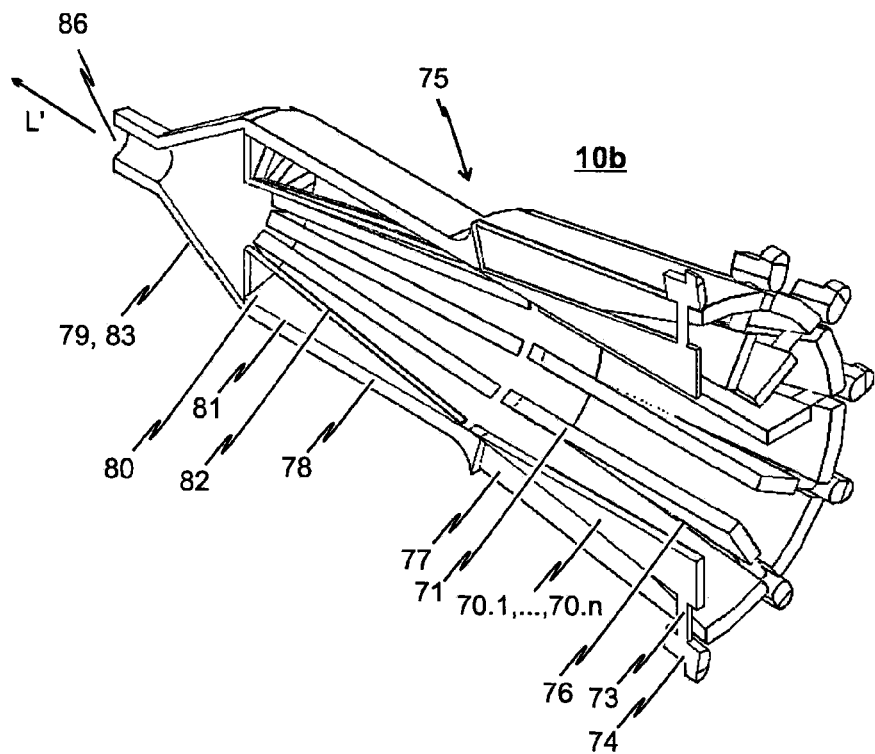
FIG. 28 a sectional view of the housing part of the compressing mechanism utilized in the third exemplary embodiment of the disclosed device for compressing a stent, wherein a plurality of preferably wedge-shaped clamping jaws is mounted in the housing part, said wedge-shaped clamping jaws being in their initial state, i.e. prior to activation of the manipulating mechanism of the device according to the third exemplary embodiment.

In detail and as can be seen, for example, from FIG. 28, the device 1b according to the third exemplary embodiment may comprise a compressing mechanism 10b having a housing part 75 in which the already mentioned wedge-shaped clamping jaws 70.1 to 70.n are mounted such as to be movable in the longitudinal direction L' of the compressing mechanism 10b relative to the housing part 75. In this respect, reference is also made to FIG. 30 which is a sectional view of the housing part 75 of the compressing mechanism 10b utilized in the third exemplary embodiment of the disclosed device 1b for compressing a stent 100. In the illustration according to FIG. 30, the plurality of preferably wedge-shaped clamping jaws 70.1 to 70.n is mounted in the housing part 75. In particular, the plurality of wedge shaped clamping jaws 70.1 to 70.n is in a state after activation of the manipulating mechanism 40b belonging to the device 1b of the third exemplary embodiment.

In contrast, FIG. 28 shows a sectional view of the housing part 75 of the compressing mechanism 10b utilized in the third exemplary embodiment of the disclosed device 1b for compressing a stent 100, wherein the preferably wedge-shaped clamping jaws 70.1 to 70.n mounted in the housing part 75 are in their initial state, i.e. prior to activation of the manipulating mechanism 40b.

Accordingly, the housing part 75 of the compressing mechanism 10b utilized in the third exemplary embodiment of the device 1b may be provided with a plurality of guiding slits 76 which extend in the longitudinal direction L' of the compressing mechanism 10b. As can be seen from the illustrations in FIG. 28 and FIG. 30, each of the plurality of guiding slits 76 interacts with one of the plurality of preferably wedge-shaped clamping jaws 70.1 to 70.n for guiding the wedge-shaped clamping jaw 70.1 to 70.n during its movement in the longitudinal direction L' of the compressing mechanism 10b relative to the housing part 75.

Referring to FIG. 33, which is a perspective view of a single wedge-shaped clamping jaw 70.1 to 70.n utilized in the third exemplary embodiment of the disclosed device 1b, each of the preferably wedge-shaped clamping jaws 70.1 to 70.n may have at least one protruding part 73 provided on the surface 72 of the clamping jaw 70.1 to 70.n which is opposite to the wedge surface 71. As can be seen from the illustrations in FIGS. 28 and 30, this protruding part 73 may be engaged with the guiding slit 76 allocated to the respective clamping jaw 70.1 to 70.n in the assembled state.

Figure 30:
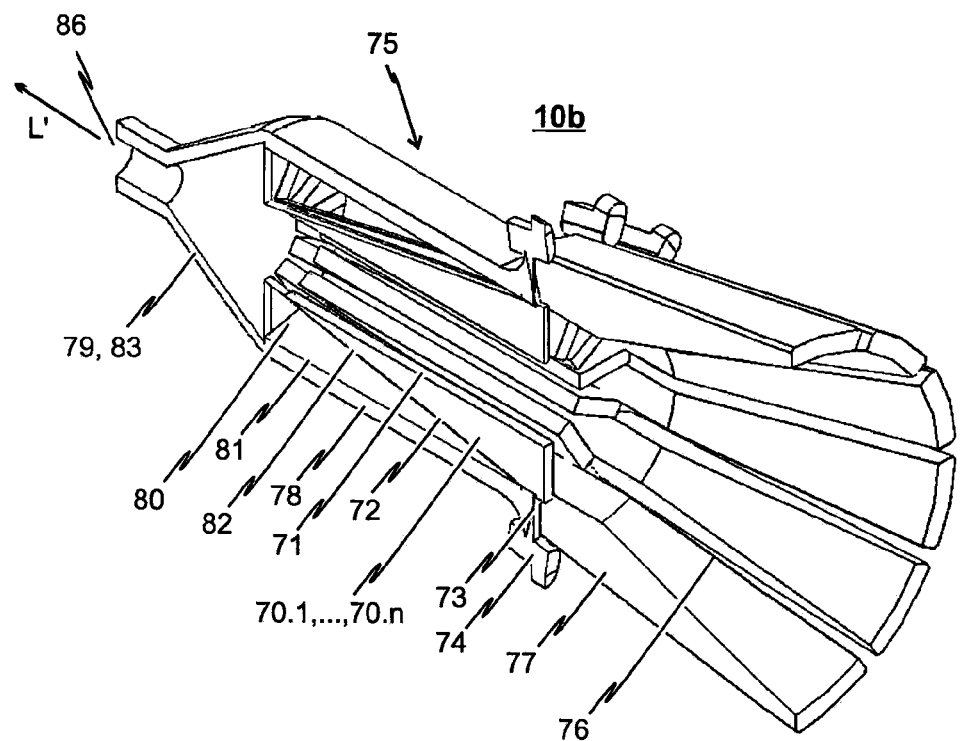
FIG. 30 a sectional view of the housing part of the compressing mechanism utilized in the third exemplary embodiment of the disclosed device for compressing a stent, wherein a plurality of preferably wedge-shaped clamping jaws is mounted in the housing part, said wedge-shaped clamping jaws being in a state after activation of the manipulation mechanism of the device according to the third exemplary embodiment.

As can be seen, in particular, from FIG. 28 or FIG. 30, the housing part 75 of the compressing mechanism 10b utilized in the third exemplary embodiment of the device 1b may be divided into a first housing section 77 and a second housing section 78. In this regard, the guiding slits 76 are only provided in the circumferential surface of the first housing section 77. On the other hand, the inner circumferential surface of the first housing section 77 is tapered towards the second housing section 78.

Preferably, the inclination angle of the inner circumferential surface of the first housing section 77 corresponds to the angle α between the wedge surface 71 of one of the plurality of preferably wedge-shaped clamping jaws 70.1 to 70.n and the surface 72 of the preferably wedge-shaped clamping jaws 70.1 to 70.n which is opposite to the wedge surface 71. In this regard, reference is also made to FIG. 33.

On the other hand, the inner circumferential surface of the second housing section 78 may be tapered towards the direction opposite to the first housing section 77, i.e. in the same direction as the inner circumferential surface of the first housing section 77.

Alternatively, the inner circumferential surface of the second housing section 78 may be at least essentially cylindrical, wherein, for each of the plurality of preferably wedge-shaped clamping jaws 70.1 to 70.n, a rail element 80 may be provided on the inner circumferential surface of the second housing section 78. As can be seen, for example, from the illustration in FIG. 28 or FIG. 30, each of the rail elements 80 may have a main surface 81 connected to the inner circumferential surface of the second housing section 78. Furthermore, each of the rail elements 80 may have a guiding surface 82 opposite to the main surface 81 for guiding the corresponding wedge-shaped clamping jaw during its movement in the longitudinal direction L' of the compressing mechanism 10b relative to the housing part 75.

Preferably, the main surface 81 of the rail element 80 and the guiding surface 82 of the rail element 80 are angled with respect to each other, wherein the angle between the main surface 81 and the guiding surface 82 of the rail element 80 may correspond to the angle $\alpha$ between the wedge surface 71 of one of the plurality of preferably wedge-shaped clamping jaws 70.1 to 70.n and the surface 72 of the wedge-shaped clamping jaw which is opposite to the wedge surface 71 (see FIG. 33).

Figure 26:
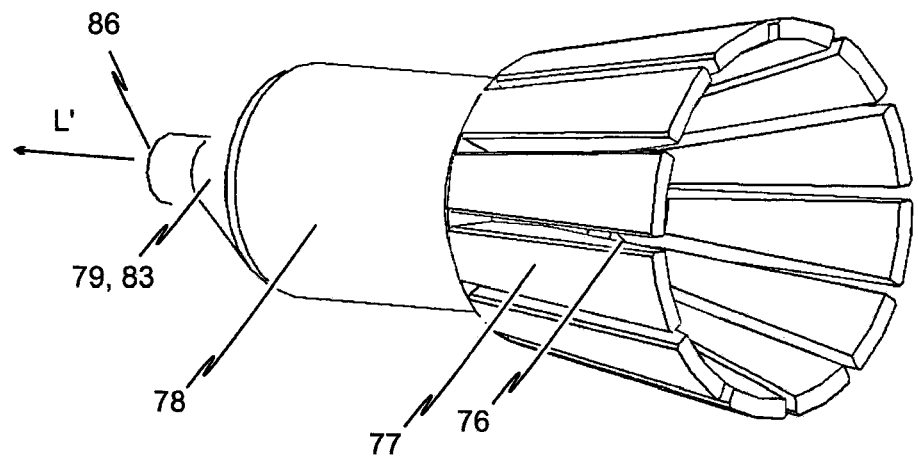
FIG. 26 a perspective view of the housing part of the compressing mechanism utilized in the third exemplary embodiment of the disclosed device for compressing a stent.
Figure 27:
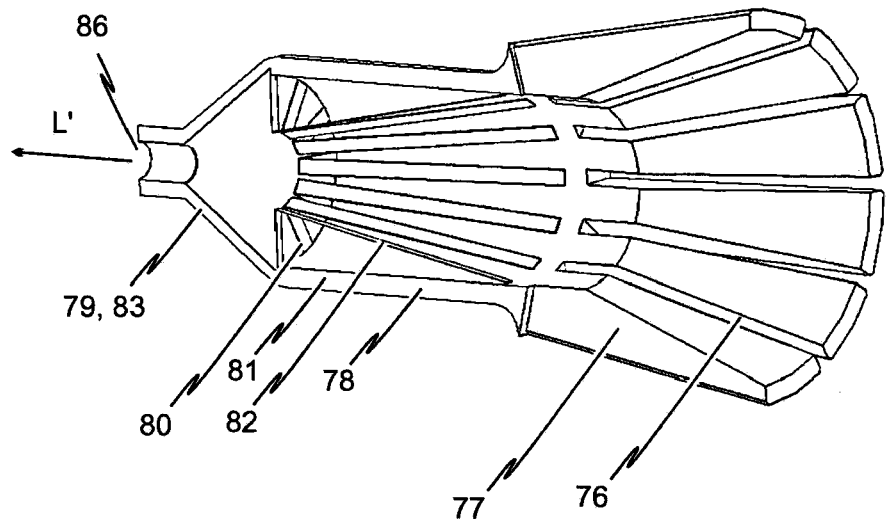
FIG. 27 a sectional view of the housing part depicted in FIG. 26.

Reference is made in the following in particular to FIG. 27, which is a sectional view of the housing part 75 depicted in FIG. 26. FIG. 26 is a perspective view of a housing part 75 of the compressing mechanism 10b which may be utilized in the third exemplary embodiment of the disclosed device 1b for compressing a stent 100.

Figure 29:
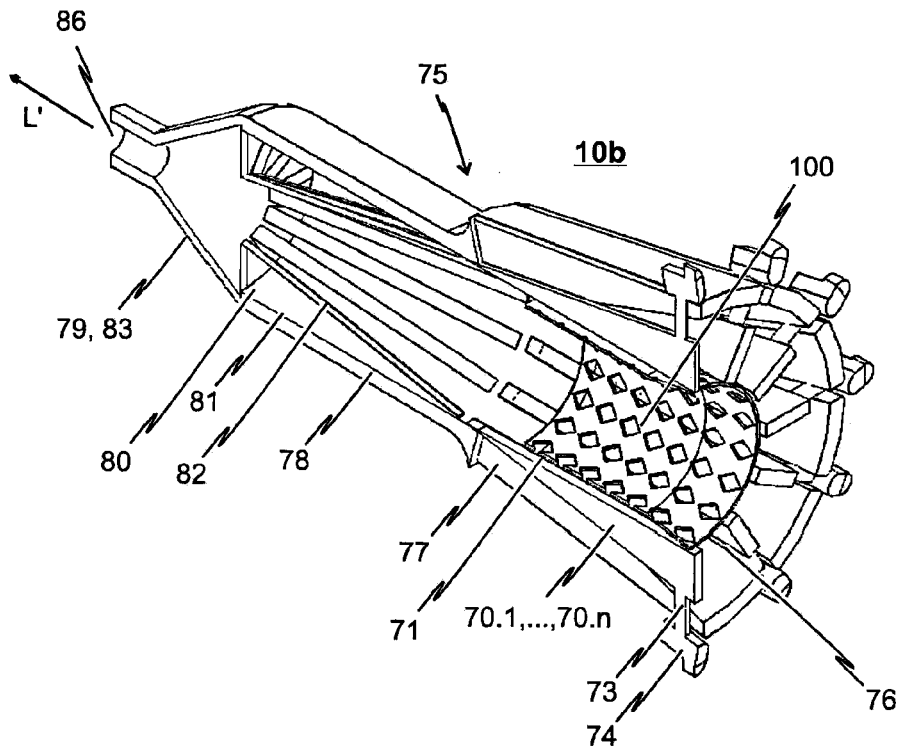
FIG. 29 a sectional view of the housing part depicted in FIG. 28 with a stent accommodated in a first housing section of the housing part, wherein a plurality of preferably wedge-shaped clamping jaws is mounted in the housing part, said wedge-shaped clamping jaws being in their initial state.
Figure 31:
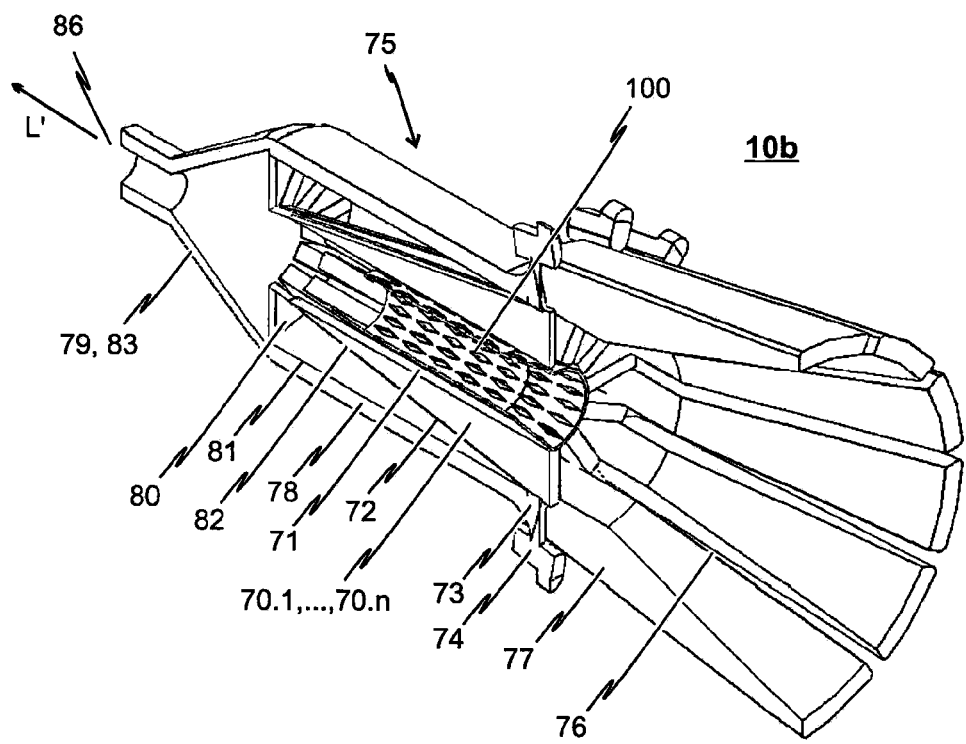
FIG. 31 a sectional view of the housing part depicted in FIG. 30 with a stent accommodated in a second housing section of the housing part, wherein a plurality of preferably wedge-shaped clamping jaws is mounted in the housing part, said wedge-shaped clamping jaws being in a state after activation of the manipulating mechanism of the device according to the third exemplary embodiment.

In addition, reference is also made to FIG. 29, which is a sectional view of the housing part 75 depicted in FIG. 28 with a stent 100 accommodated in the first housing section 77 of the housing part 75. In the illustration of FIG. 29, the preferably wedge-shaped clamping jaws 70.1 to 70.n mounted in the housing part 75 are respectively in their initial state, i.e. prior to activation of a manipulating mechanism 40b belonging to the device 1b according to the third exemplary embodiment. On the other hand, FIG. 31 shows a sectional view of the housing part 75 depicted in FIG. 30 with a stent 100 accommodated in the second housing section 78 of the housing part 75, wherein the preferably wedge-shaped clamping jaws 70.1 to 70.n mounted in the housing part 75 are in a state after activation of the manipulating mechanism 40b.

Accordingly, the housing part 75 utilized in the third exemplary embodiment of the device 1b may have a second housing section 78 which is followed by a third housing section 79, said third housing section 79 being axially aligned with the second housing section 78. In detail and as depicted in one of FIGS. 26 to 31, the third housing section 79 may incorporate a cone 83 that allows a final diameter reduction of a stent 100 compressed by the plurality of preferably wedge-shaped clamping jaws 70.1 to 70.n after their movement in the radial direction effected by the manipulating mechanism 40b.

Figure 32:
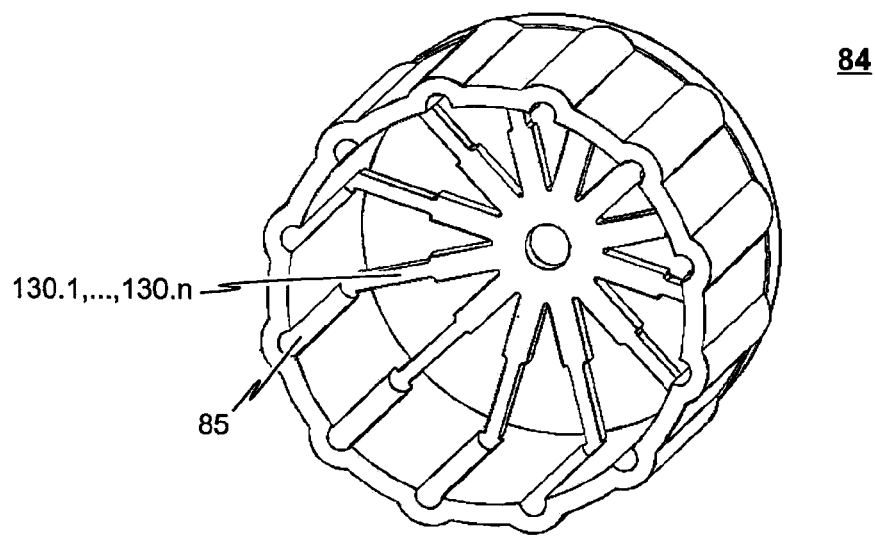
FIG. 32 a perspective view of the manipulating part of the manipulating mechanism utilized in the third exemplary embodiment of the disclosed device for compressing a stent.

Reference is made in the following in particular to FIG. 32 for describing the manipulating mechanism 40b which may be utilized in the third exemplary embodiment of the device 1b. In detail, according to the third exemplary embodiment of the device 1b, the manipulating mechanism 40b may comprise a manipulating part 84. A perspective view of the manipulating part 84 of the manipulating mechanism 40b utilized in the third exemplary embodiment of the disclosed device 1b for compressing a stent 100 is shown in FIG. 32.

Hence, the manipulating part 84 of the manipulating mechanism 40b may have an essentially cup-shaped configuration which is adapted to receive the housing part 75 of the compressing mechanism 10b in a releasable manner by attaching the manipulating part 84 to the housing part 75. In this regard, reference is also made to illustration of, for example, FIG. 22 or FIG. 23. FIG. 22 shows a perspective view of the third exemplary embodiment of the disclosed device 1b for compressing a stent 100 with a stent 100 accommodated in the compressing mechanism 10b of the device 1b prior to the actual compressing of the stent 100, wherein FIG. 23 is a sectional view of the device depicted in FIG. 22.

A comparison of FIG. 23 on the one hand and FIG. 25 on the other hand shows that, according to the third exemplary embodiment of the device 1b, the manipulating part 84 of the manipulating mechanism 40b is moveable relative to the housing part 75 of the compressing mechanism 10b, wherein the manipulating part 84 interacts with the plurality of preferably wedge-shaped clamping jaws 70.1 to 70.n mounted in the housing part 75 of the compressing mechanism 10b such that, by moving the manipulating part 84 relative to the housing part 75 in the longitudinal direction L' of the compressing mechanism 10b, the plurality of preferably wedge-shaped clamping jaws 70.1 to 70.n is moved in the longitudinal direction L' of the compressing mechanism 10b relative to the housing part 75 of the compressing mechanism 10b.

For this purpose, each of the plurality of preferably wedge-shaped clamping jaws 70.1 to 70.n may have—as depicted in particular in FIG. 33—a head portion 74 provided on the surface 72 of the clamping jaw 70.1 to 70.n which is opposite to the respective wedge surface 71. The respective head portions 74 of the plurality of preferably wedge-shaped clamping jaws 70.1 to 70.n protrude from the outer circumferential surface of the housing part 75 of the compressing mechanism 10 when these clamping jaws 70.1 to 70.n are mounted in the housing part 75.

As can be seen, in particular, from the illustration of FIG. 32, the manipulating part 84 of the manipulating mechanism 40b utilized in the third exemplary embodiment of the device 1b may be provided with a plurality of dedicated grooves 85, each of which extends in the longitudinal direction L" of the manipulating part 84. These dedicated grooves 85 are designed such as to fit the head portions 74 of the preferably wedge-shaped clamping jaws 70.1 to 70.n and to lock them in place.

According to FIG. 23, in the initial state of the device 1b, i.e. prior to activation of the manipulating mechanism 40b, the respective head portions 74 of the clamping jaws 70.1 to 70.n are received within the dedicated grooves 85 of the manipulating part 84 such that these head portions 74 are engaged with the cup-shaped manipulating part 84 of the manipulating mechanism 40b.

As can be seen from the illustration according to FIG. 32, the manipulating part 84 comprises a plurality of radial arms 130.1 to 130.n. In detail, for each of the plurality of dedicated grooves 85, one of the plurality of radial arms 130.1 to 130.n is allocated.

When the manipulating part 84 is attached to the housing part 75, each of the radial arms 130.1 to 130.n of the manipulating part 84 abuts on the corresponding clamping jaw 70.1 to 70.n whose head portion 74 is received within the dedicated groove 85 of the manipulating part 84. When moving the cup-shaped manipulating part 84 relative to the housing part 75 in the direction of the housing part 75, the manipulating part 84 pushes the clamping jaws 70.1 to 70.n in the longitudinal direction because, during the movement of the manipulating part 84, the radial arms 130.1 to 130.n of the manipulating part 84 remain in contact with the clamping jaws 70.1 to 70.n. Hence, when moving the cup-shaped manipulating part 84 in the longitudinal direction relative to the housing part 75, the clamping jaws 70.1 to 70.n are also moved in the longitudinal direction. At the same time, the clamping jaws

70.1 to 70.$n$ are moved radially inward due to the tapered outer surface of the housing 76.

After activation of the manipulating mechanism 40$b$, the respective head portions 74 of the clamping jaws 70.1 to 70.$n$ are disengaged from the dedicated grooves 85 of the cup-shaped manipulating part 84 because of their radial movement. In this respect, reference is also made to FIG. 25 which shows a sectional view of the device 1$b$ with an at least partly compressed stent 100 accommodated in the compressing mechanism 10$b$ of the device after activation of the manipulating mechanism 40$b$. However, although the head portions 74 of the clamping jaws 70.1 to 70.$n$ are disengaged from the dedicated grooves 85, the radial arms 130.1 to 130.$n$ of the manipulating part 84 remain in contact with the clamping jaws 70.1 to 70.$n$ so that the radial movement of the clamping jaws 70.1 to 70.$n$ does not affect the interaction between the manipulating part 84 on the one hand and the clamping jaws 70.1 to 70.$n$ on the other hand.

As can be seen from FIG. 23 and FIG. 25, the radial arms 130.1 to 130.$n$ of the manipulating part 84 may also abut on a stent 100 accommodated in the cavity encircled by the respective wedge surfaces 71 of the clamping jaws 70.1 to 70.$n$. Hence, when moving the cup-shaped manipulating part 84 relative to the housing part 115 in the direction of the housing part 75, the radial arms 130.1 to 130.$n$ of the manipulating part 84 push the clamping jaw 70.1 to 70.$n$ and the stent 100 accommodated in the housing part 75 in the longitudinal direction.

As can be seen from the illustration according to FIG. 32, the manipulating part 84 is provided with a plurality of radial arms 130.1 to 130.$n$. From the foregoing description it becomes clear that the number of the radial arms 130.1 to 130.$n$ shall be identical with the number of clamping jaws 70.1 to 70.$n$. This is due to the fact that one of the radial arms 130.1 to 130.$n$ is allocated to each of the clamping jaws 70.1 to 70.$n$ thereby assuring that each of the clamping jaws 70.1 to 70.$n$ can be moved in the longitudinal direction after activation of the manipulating mechanism 40$b$. Only for reasons of simplification and clarity, in the illustrations according to FIGS. 19 to 25, the manipulating part 84 is depicted with a reduced number of radial arms 130.1 to 130.$n$.

As can be seen, for example, from FIG. 22, the device 1$b$ according to the third exemplary embodiment may have a push rod leadthrough 86 for receiving a push rod 2$b$. An exemplary embodiment of a suitable push rod 2$b$ is depicted in FIG. 34. In detail, FIG. 34 is a perspective view of a push rod 2$b$ which may be used for pushing an at least partly compressed stent 100 from the second housing section 78 to the third housing section 79 of the housing part 75 utilized in the compressing mechanism 10$b$ of the third exemplary embodiment of the disclosed device 1$b$.

For this purpose, the push rod lead through 86 is preferably axially aligned with the device 1$b$ and passes through the entire device 1$b$. Moreover, it is preferred that the push rod lead through 86 has a diameter which essentially corresponds to the final diameter of the stent after being reduced in the compressing mechanism 10$b$ of the device 1$b$.

Briefly summarized, the device 1$b$ according to the third exemplary embodiment may comprise a compressing mechanism 10$b$ having a housing part 75 and a plurality of preferably wedge-shaped clamping jaws 70.1 to 70.$n$. Furthermore, the third exemplary embodiment of the device 1$b$ may comprise a manipulating part 84 belonging to a manipulating mechanism 40$b$.

The device 1$b$ according to the third exemplary embodiment functions as follows:

First of all, the operator should load the stent 100 to be compressed into the housing part 75 of the compressing mechanism 10$b$. By using the cup-shaped manipulating part 84 of the manipulating mechanism 40$b$, the stent 100 may be locked in place. The cup-shaped manipulating part 84 has dedicated grooves 85 to secure the stent 100 accommodated in the housing part 54 and to allow only minimal stresses when advancing the manipulating mechanism 40$b$ of the device 1$b$, i.e. when moving/pushing the manipulating part 84 of the manipulating mechanism 40$b$ in the longitudinal direction L of the device 1$b$ relative to the compressing mechanism 10$b$ in order to move the preferably wedge-shaped clamping jaws 70.1 to 70.$n$ in the radial direction of the device 1$b$ thereby adjusting the internal cross-sectional diameter of the compressing mechanism 10$b$.

In particular, for manipulating the preferably wedge-shaped clamping jaws 70.1 to 70.$n$ of the compressing mechanism 10$b$, the preferably cup-shaped manipulating part 84 has dedicated grooves 85 to fit the head portions 74 of the preferably wedge-shaped clamping jaws 70.1 to 70.$n$ and to lock them in place. In addition, the manipulating part 84 is provided with radial arms 130.1 to 130.$n$ to abut on the clamping jaws 70.1 to 70.$n$.

In detail, for manipulating the preferably wedge-shaped clamping jaws 70.1 to 70.$n$ of the compressing mechanism 10$b$, the operator should push forward the cup-shaped manipulating part 84 relative to the housing part 75. This will cause the clamping jaws 70.1 to 70.$n$ to slide forward in the longitudinal direction L of the device 1$b$ relative to the housing part 75 of the compressing mechanism 10$b$ and along with the cup-shaped manipulating part 84 of the manipulating mechanism 40$b$.

As already discussed in connection with the illustrations of, for example, FIGS. 28 to 31, when activating the manipulating mechanism 40$b$, the clamping jaws 70.1 to 70.$n$ slide inside the housing part 75 of the compressing mechanism 10$b$ in dedicated angled rails 80. This design causes continues inner diameter reduction while the cup-shaped manipulating part 84 is pushed forward.

According to the third exemplary embodiment of the device 1$b$ for compressing a stent 100, the stent 100 accommodated in the compressing mechanism 10$b$ of the device 1$b$ will be crimped in a combined motion: diameter reduction while being advanced forward.

The housing part 75 of the compressing mechanism 10$b$ may further incorporate a cone 83 that allows a final diameter reduction to the desired delivery catheter. Final loading is then done using the push rod 2$b$ that advances the fully compressed stent 100 into, for example, a delivery catheter.

Reference will be made in the following to FIGS. 35 to 42 in describing an exemplary embodiment of a device 1$c$ for compressing stent 100 according to the fourth embodiment. Elements in FIGS. 35 to 42 that are generally similar to previously described elements have the same reference numbers compared with the reference numbers in FIGS. 1 to 10 and FIGS. 12 to 34 previously used for the similar elements.

Figure 35:
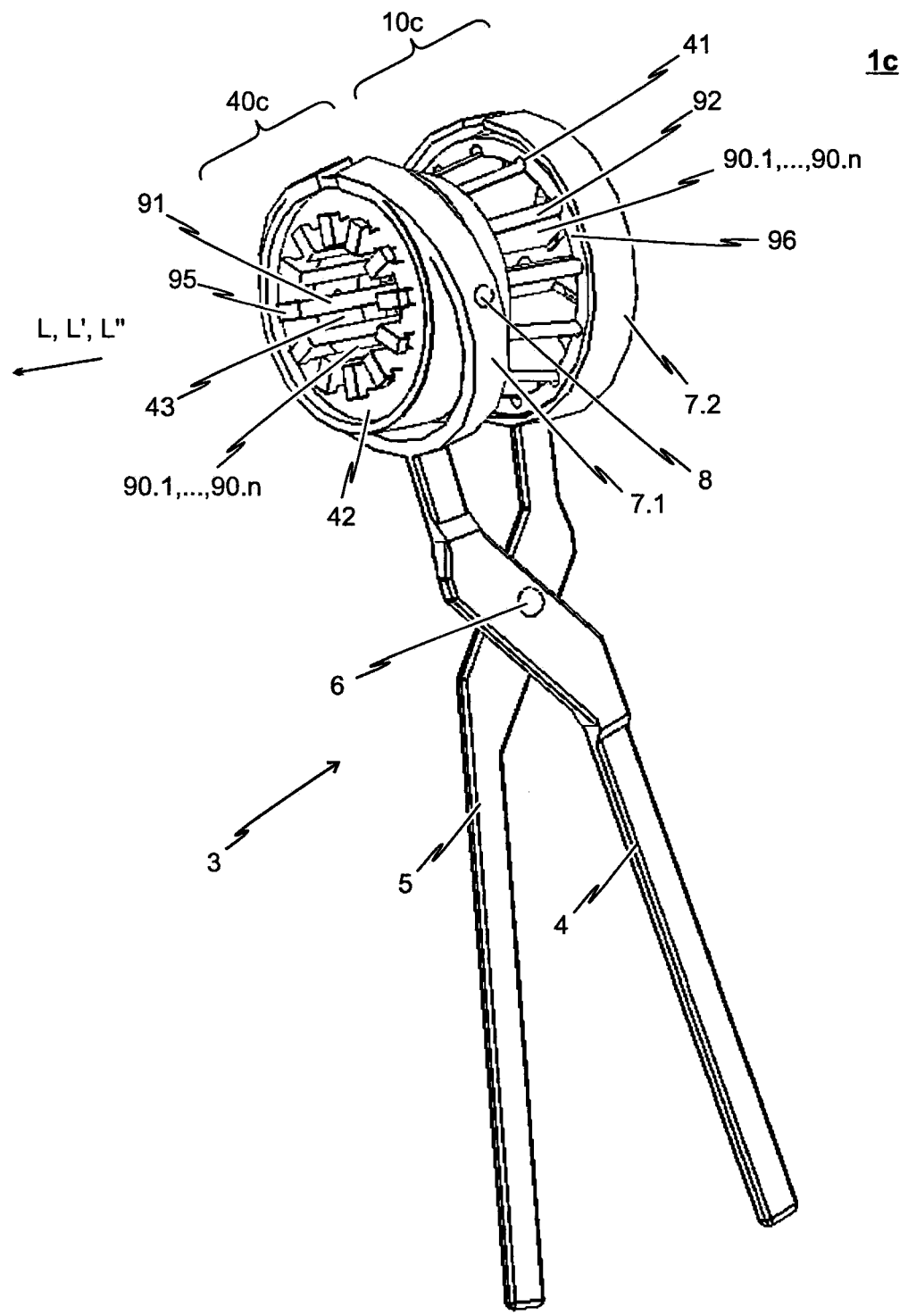
FIG. 35 a perspective view of a fourth exemplary embodiment of the disclosed device for compressing a stent, wherein the device is shown in its assembled condition ready for receiving a stent to be compressed.
Figure 36:
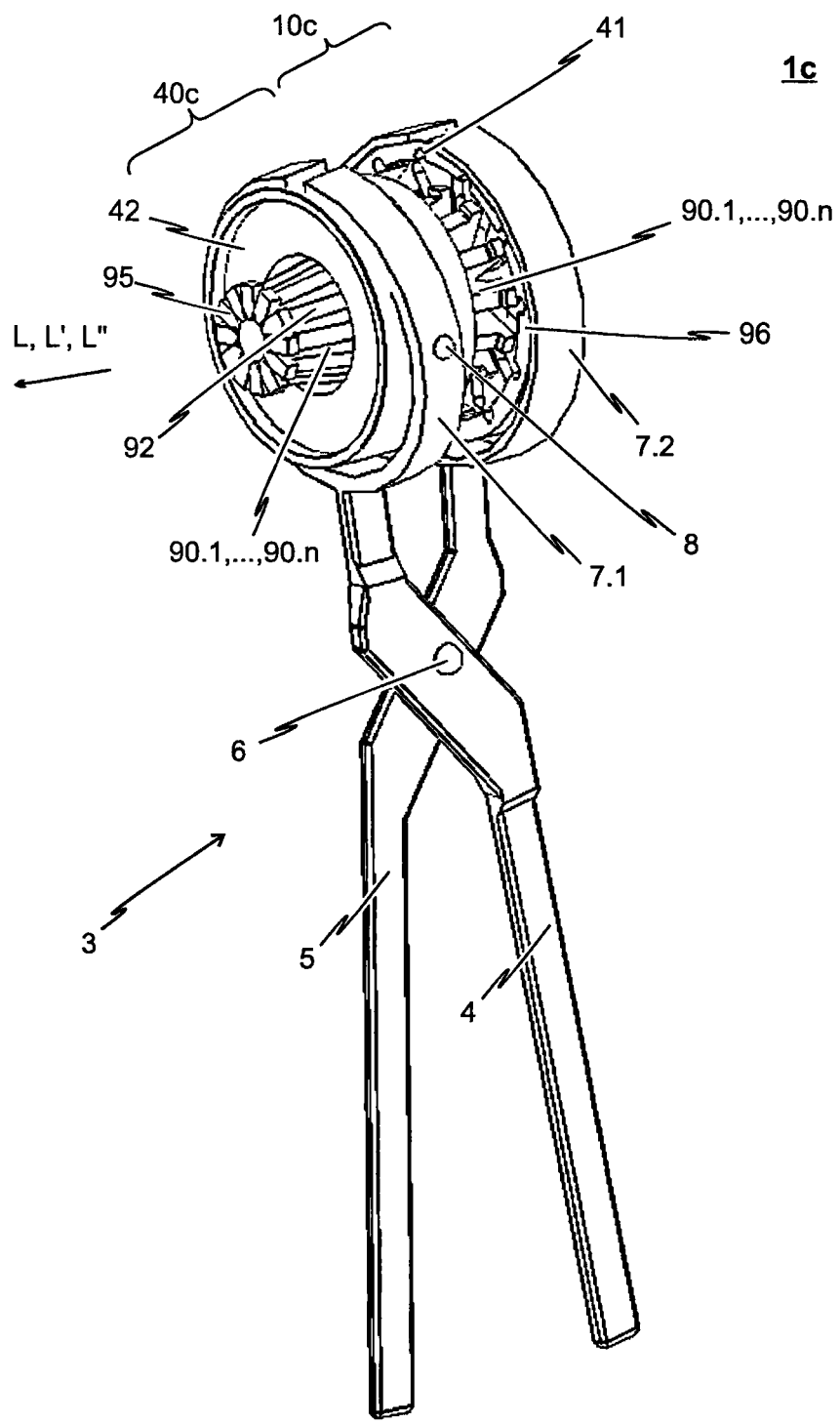
FIG. 36 a perspective view of the fourth exemplary embodiment of the disclosed device for compressing a stent, wherein the device is shown in its assembled condition after activation of the manipulating mechanism belonging to the device according to the fourth exemplary embodiment.

In detail, FIG. 35 is a perspective view of the fourth exemplary embodiment of the disclosed device 1$c$ for compressing a stent, wherein the device 1$c$ is shown in its assembled condition ready for receiving a stent to be compressed. FIG. 36 is a perspective view of the fourth exemplary embodiment of the device 1$c$, wherein the device 1$c$ is shown in its assembled condition after activation of a manipulating mechanism 40$c$ belonging to the device 1$c$.

In the fourth exemplary embodiment of the disclosed device 1$c$, a compressing mechanism 10$c$ is utilized, the structure thereof being similar to the compressing mechanism 10b of the third exemplary embodiment of the device 1b, which has already been discussed in conjunction with FIGS. 19 to 34.

Hence, the compressing mechanism 10c of the device 1c according to the fourth exemplary embodiment comprises externally manipulated clamping means and is designed so as to exert a compressive force in radial direction on at least parts of a stent to be compressed. For this purpose, the stent to be compressed can be at least partly accommodated within the compressing mechanism 10c of the device 1c such that the cross-section of the stent can be reduced to a predefinable value at least at certain areas by the externally manipulatable clamping means of the compressing mechanism 10c.

Figure 42:
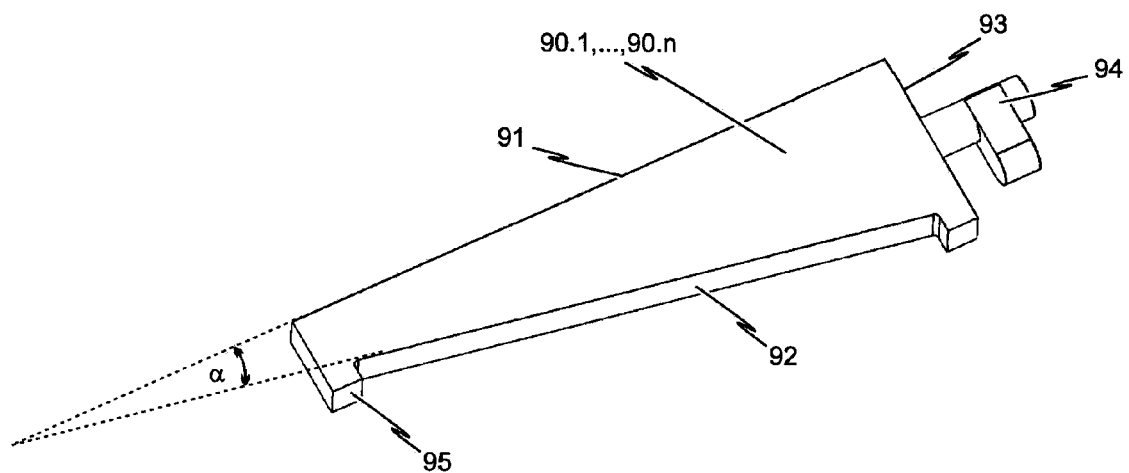
FIG. 42 a perspective view of a single wedge-shaped clamping jaw which serves as clamping means in the compressing mechanism utilized in the fourth exemplary embodiment of the disclosed device for compressing a stent.

In detail, the clamping means utilized in the fourth exemplary embodiment of the device 1c may comprise a plurality of preferably wedge-shaped clamping jaws 90.1 to 90.n. An exemplary embodiment of a single clamping jaw of the compressing mechanism 10c utilized in the fourth exemplary embodiment of the disclosed device 1c is shown in FIG. 42.

Hence, each of the preferably wedge-shaped clamping jaws 90.1 to 90.n, which may be used in the fourth exemplary embodiment of the disclosed device 1c, has a wedge surface 91. As can be seen from, for example, FIG. 35, in the assembled state of the device 1c according to the fourth exemplary embodiment, the preferably wedge-shaped clamping jaws 90.1 to 90.n are circumferentially arranged such that the respective wedge surfaces 91 of the preferably wedge-shaped clamping jaws 90.1 to 90.n encircle a cavity which serves as receptacle within which a stent to be compressed can be at least partly accommodated.

For compressing a stent, which is at least partly accommodated in the receptacle formed by the preferably wedge-shaped clamping jaws 90.1 to 90.n, the preferably wedge-shaped clamping jaws 90.1 to 90.n are moveable in the radial direction of the device 1c. This allows adjusting the internal cross-sectional diameter of the receptacle. In this respect, a compressive force in radial direction on at least parts of a stent accommodated within the receptacle can be exerted by the plurality of preferably wedge-shaped clamping jaws 90.1 to 90.n.

In the following, a compressing mechanism 10c which may be used in the device 1c according to the fourth exemplary embodiment will be described with reference to FIGS. 39 and 41. In detail, according to the fourth exemplary embodiment of the device 1c, the compressing mechanism 10c may comprise a housing part 96 for supporting the plurality of preferably wedge-shaped clamping jaws 90.1 to 90.n.

Figure 39A:
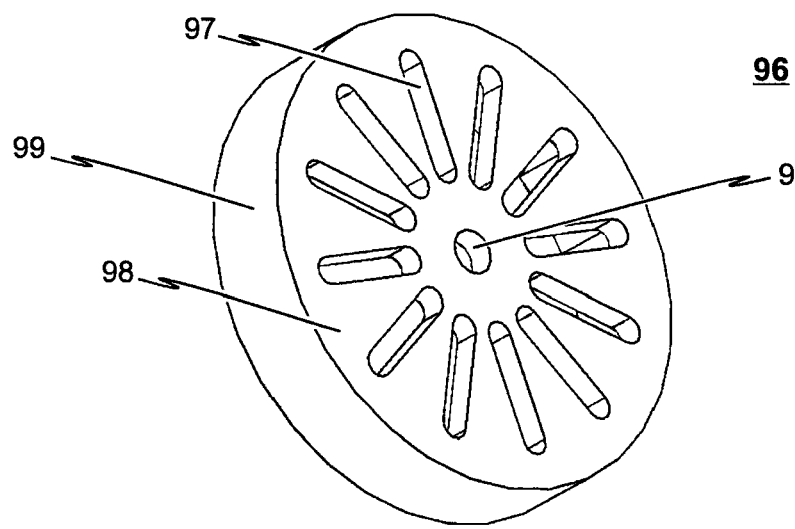
FIG. 39a a first perspective view of the housing part of the compressing mechanism utilized in the fourth exemplary embodiment of the disclosed device for compressing a stent.
Figure 39B:
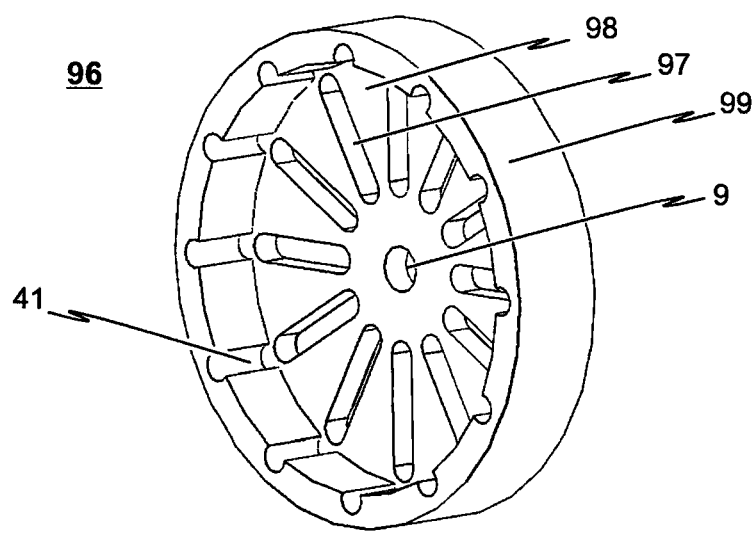
FIG. 39b a second perspective view of the housing part of the compressing mechanism utilized in the fourth exemplary embodiment of the disclosed device for compressing a stent.
Figure 41A:
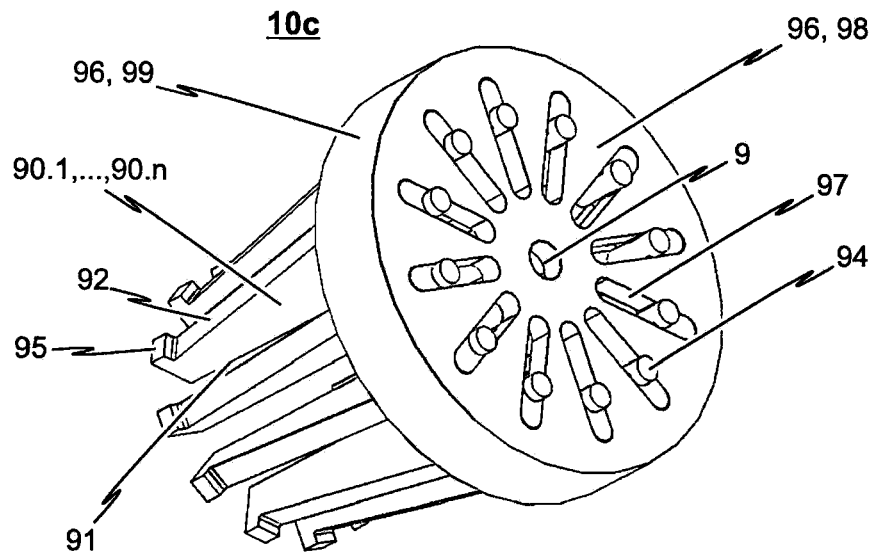
FIG. 41a a first perspective view of a housing part of the compressing mechanism utilized in the fourth exemplary embodiment of the disclosed device for compressing a stent, wherein a plurality of preferably wedge-shaped clamping jaws is mounted in the housing part, said wedge-shaped clamping jaws being in their initial state, i.e. prior to activation of the manipulating mechanism belonging to the device according to the fourth exemplary embodiment.

An exemplary embodiment of a housing part 96 which may be utilized in the fourth exemplary embodiment of the disclosed device 1c is shown in FIGS. 39a and 39b. FIG. 41a shows a first perspective view of the housing part 96 of the compressing mechanism 10c which may be utilized in the fourth exemplary embodiment of the disclosed device 1c, wherein the plurality of preferably wedge-shaped clamping jaws 90.1 to 90.n is mounted in the housing part 96.

Hence, the housing part 96 of the compressing mechanism 10c may be provided with a plurality of guiding slits 97 which extend in the radial direction of the compressing mechanism 10c. Each of the plurality of guiding slits 97 interacts with one of the plurality of preferably wedge-shaped clamping jaws 90.1 to 90.n for guiding the corresponding clamping jaw during its movement in the radial direction L' of the compressing mechanism 10c relative to the housing part 96. In this respect, the housing part 96 of the compressing mechanism 10c, which may be utilized in the fourth exemplary embodiment of the disclosed device 1c, supports the plurality of preferably wedge-shaped clamping jaws 90.1 to 90.n in such a way that the preferably wedge-shaped clamping jaws 90.1 to 90.n are moveable in the radial direction of the compressing mechanism 10c relative to the housing part 96.

Reference is made to FIG. 42, which is a perspective view of a single wedge-shaped clamping jaw, which may be used in the compressing mechanism 10c of the fourth exemplary embodiment of the disclosed device 1c for compressing a stent. As shown, the preferably wedge-shaped clamping jaw may have at least one protruding part 94 provided on a front surface 93 of the clamping jaw. In the mounted state, the at least one protruding part 94 of the clamping jaw is engaged with the corresponding guiding slit 97 allocated to the clamping jaw. In this respect, reference is also made to FIG. 41a, which is a first perspective view of the housing part 96 of the compressing mechanism 10c which may be utilized in the fourth exemplary embodiment of the disclosed device 1c.

As can be seen, in particular, from FIG. 39b, which is a perspective view of the housing part 96 of the compressing mechanism 10c, which may be utilized in the fourth exemplary embodiment of the disclosed device 1c, the housing part 96 may have a cup-shaped configuration with a disk-like part 98 and a ring-shaped part 99 provided at the circumference of the disk-like part 98, wherein the already mentioned guiding slits 97 are provided in the disk-like part 98.

In particular, the ring-shaped part 99 of the housing part 96 may be provided with a plurality of dedicated grooves 41, each of which extending in the longitudinal direction L" of the housing part 96. Each of the plurality of dedicated grooves 41 may be designed such as to fit a flange surface 92 of one of the plurality of preferably wedge-shaped clamping jaws 90.1 to 90.n. As can be seen from the illustration in FIG. 42, the flange surface 92 of the clamping jaw is opposite to the already mentioned wedge surface 91 of the clamping jaw.

Figure 41B:
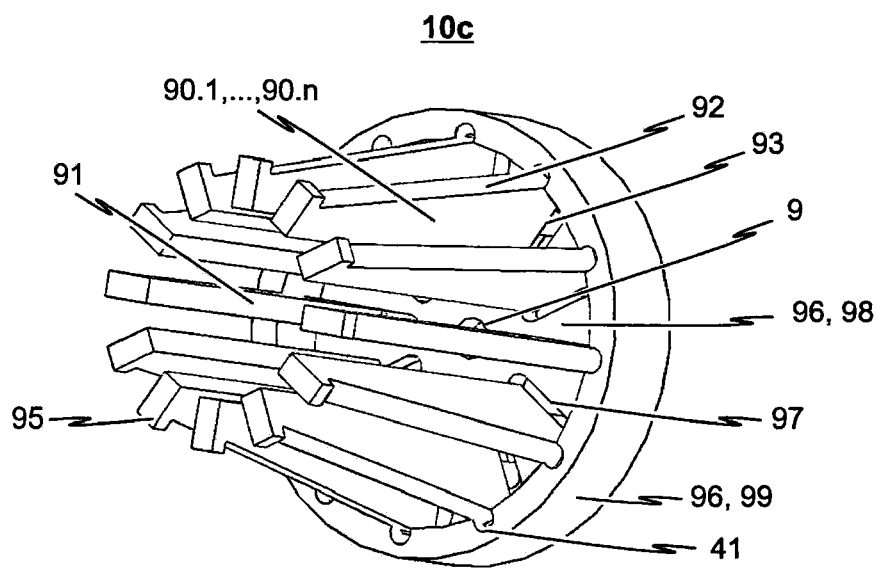
FIG. 41b a second perspective view of the housing part of the compressing mechanism utilized in the fourth exemplary embodiment of the disclosed device for compressing a stent, wherein a plurality of preferably wedge-shaped clamping jaws is mounted in the housing part, said wedge-shape clamping jaws being in their initial state, i.e. prior to activation of the manipulating mechanism belonging to the device according to the fourth exemplary embodiment.

The plurality of dedicated grooves 41 provided in the ring-shaped part 99 of the housing part 96 serves for locking the preferably wedge-shaped clamping jaws 90.1 to 90.n in place, as can be seen, for example, from FIG. 41b which is a perspective view of the housing part 96 of the compressing mechanism 10c utilized in the fourth exemplary embodiment of the disclosed device 1c. In the illustration of FIG. 41b, the preferably wedge-shaped clamping jaws 90.1 to 90.n mounted in the housing part 96 in their initial state, i.e. prior to activation of a manipulating mechanism 40c belonging to the device 1c according to the fourth exemplary embodiment.

In the illustration according to FIG. 35, the preferably wedge-shaped clamping jaws 90.1 to 90.n are also in their initial state, in which the respective wedge surfaces 91 of the preferably wedge-shaped clamping jaws 90.1 to 90.n encircle a cavity which serves as receptacle within which a stent to be compressed can be at least partly accommodated.

As already mentioned, in the fourth exemplary embodiment of the disclosed device 1c, each of the plurality of preferably wedge-shaped clamping jaws 90.1 to 90.n may have a wedge surface 91 and a flange surface 92 which is opposite to the wedge surface 91. In this regard, reference is also made to FIG. 42. In the assembled state of the device 1c (see FIG. 35 or FIG. 36), the wedge surface 91 of the plurality of preferably wedge-shaped clamping jaws 90.1 to 90.n encircle an at least essentially tubular cavity which serves as receptacle within which a stent 100 to be compressed can be at least partly accommodated.

In detail, the preferably wedge-shaped clamping jaws 90.1 to 90.n are designed and mounted in the housing part 96 such that the flange surfaces 92 of the plurality of preferably wedge-shaped clamping jaws 90.1 to 90.n describe a truncated cone which tapers on the direction opposite to the housing part 96. In this regard, reference is also made to FIGS. 41a and 41b which show perspective views of a housing part 96 of the compressing mechanism 10c utilized in the fourth exemplary embodiment of the disclosed device 1c, wherein the clamping jaws 90.1 to 90.n mounted in the housing part 96 are in their initial state, i.e. prior to activation of the manipulating mechanism 40c belonging to the device 1c.

The truncated cone described by the flange surfaces 92 of the plurality of preferably wedge-shaped clamping jaws 90.1 to 90.n allows for manipulating the preferably wedge-shaped clamping jaws 90.1 to 90.n such as to move the clamping jaws 90.1 to 90.n in the radial direction of the compressing mechanism 10c relative to the housing part 96.

Contrary to the third exemplary embodiment of the disclosed device 1b, however, in the fourth exemplary embodiment of the device 1c, the housing part 96 may be designed such as to accommodate only a part of each of the plurality of preferably wedge-shaped clamping jaws 90.1 to 90.n. In particular and as can be seen, for example, from the perspective views depicted in FIGS. 41a and FIG. 41b, the respective end sections of the clamping jaws 90.1 to 90.n, which are opposite to the respective front surfaces 93 of the clamping jaws 90.1 to 90.n, are not accommodated by the housing part 96.

As will be described in the following, these respective end sections of the clamping jaws 90.1 to 90.n serve for interacting with a manipulating mechanism 40c. In detail, the manipulating mechanism 40c is movable relative to the compressing mechanism 10c and, in particular, relative to the housing part 96 of the compressing mechanism 10c in order to push the clamping jaws 90.1 to 90.n mounted in the housing part 96 in the radial direction of the compressing mechanism 10c thereby adjusting the internal cross-sectional diameter of the compressing mechanism 10c.

A comparison of FIG. 35, which shows the device 1c of the fourth exemplary embodiment in its assembled condition and ready for receiving a stent to be compressed, with FIG. 36, which shows the device 1c after activation of the manipulating mechanism 40c, shows that, according to the fourth exemplary embodiment of the disclosed device 1c, the manipulating mechanism 40c may comprise a manipulating part 42 which is movable in the longitudinal direction L of the device 1c relative to the housing part 96 of the compressing mechanism 10c and the preferably wedge-shaped clamping jaws 90.1 to 90.n. In particular, the manipulating part 42 of the manipulating mechanism 40c is designed as to interact with the plurality of preferably wedge-shaped clamping jaws 90.1 to 90.n such that, by moving the manipulating part 42 in the longitudinal direction L' of the compressing mechanism 10c relative to the housing part 96, the preferably wedge-shaped clamping jaws 90.1 to 90.n supported by the housing part 96 are moved in the radial direction of the device 1c.

Figure 38A:
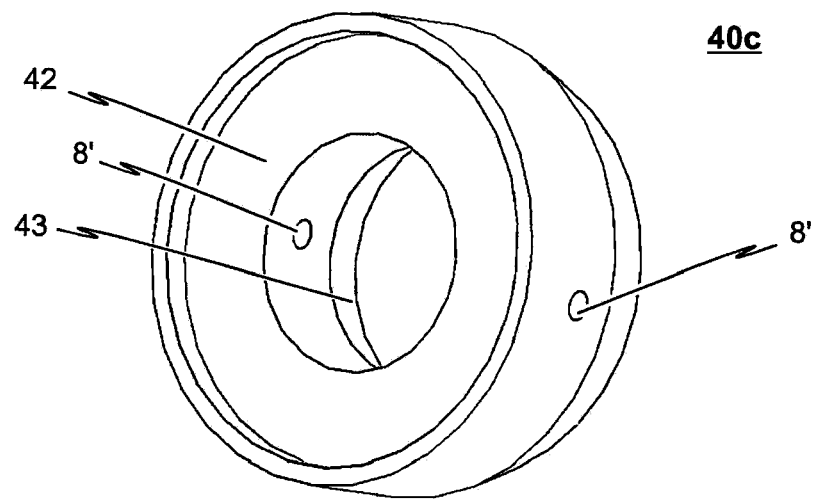
FIG. 38a a first perspective view of the manipulating part of the manipulating mechanism utilized in the fourth exemplary embodiment of the disclosed device for compressing a stent.
Figure 38B:
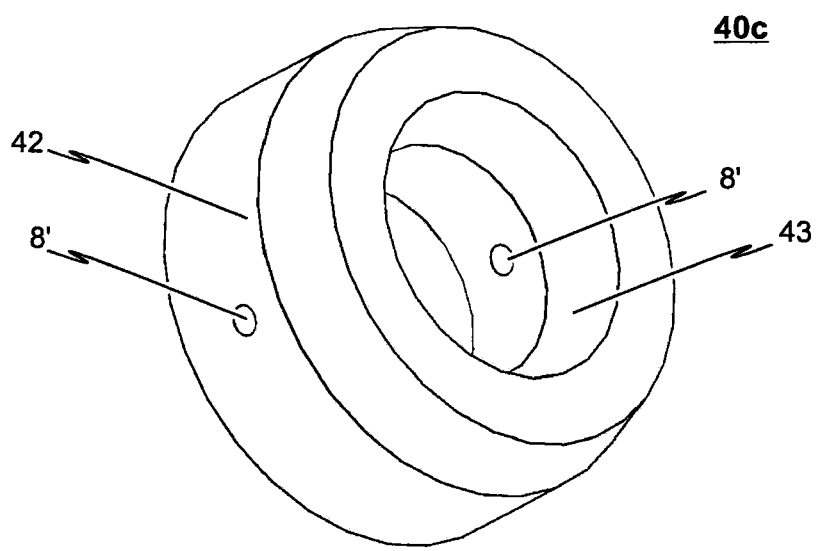
FIG. 38b a second perspective view of the manipulating part of the manipulating mechanism utilized in the fourth exemplary embodiment of the disclosed device for compressing a stent.

An exemplary embodiment of the manipulating part 42 of the manipulating mechanism 40c, which may be used in the fourth exemplary embodiment of the disclosed device 1c, is shown in perspective views in FIGS. 38a and 38b.

Hence, the manipulating part 42 of the manipulating mechanism 40c may have a ring-shaped configuration adapted to encircle the plurality of preferably wedge-shaped clamping jaws 90.1 to 90.n such that at least the respective end sections of the clamping jaws 90.1 to 90.n pass through the ring-shaped manipulating part 42. In this regard, reference is also made to the illustrations in FIGS. 35 and 36.

As shown in FIG. 38b, the manipulating part 42 may have a guiding surface 43. In the assembled state of the device 1c according to the fourth exemplary embodiment, a contact area of the respective flange surfaces 92 of the plurality of preferably wedge-shaped clamping jaws 90.1 to 90.n abuts on the guiding surface 43 of the manipulating part 42. The guiding surface 43 of the manipulating part 42 is sloped with respect to the direction of the longitudinal direction L" of the manipulating part 42. The angle of the slope essentially corresponds to the angle α drawn by the flange surface 92 and the wedge surface 91 of one of the plurality of clamping jaws 90.1 to 90.n. In this regard, reference is also made to FIG. 42.

In the exemplary embodiment of the clamping jaws 90.1 to 90.n, each of the preferably wedge-shaped clamping jaws 90.1 to 90.n may have a stop member 95 provided at the end section of the clamping jaw opposite to the front surface 93 of the clamping jaw, as can be seen, for example, from FIG. 42. In the fully assembled state of the device 1c (see FIGS. 35 and 36), the stop members 95 of the clamping jaws 90.1 to 90.n may serve for restricting a movement of the manipulating part 42 in the longitudinal direction L of the device 1c relative to the housing part 96 of the compressing mechanism 40c and the clamping jaws 90.1 to 90.n. The stop member 95 may be designed, for example, as a nose-like part protruding from the flange surface 92 of the wedge-shaped clamping jaw radially outwards, as depicted in FIG. 42.

Figure 37:
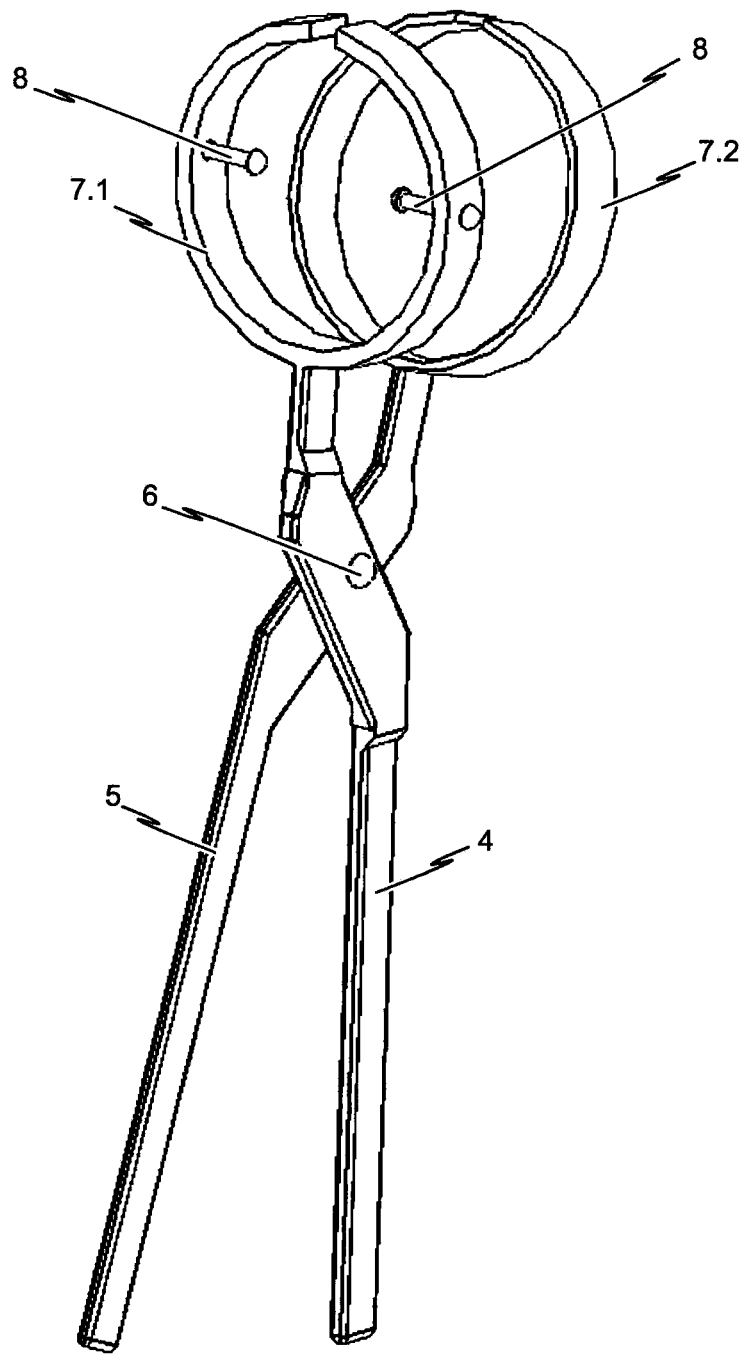
FIG. 37 a perspective view of the gripper-like mechanism utilized in the fourth exemplary embodiment of the disclosed device for compressing a stent.

As already mentioned, for manipulating the plurality of preferably wedge-shaped clamping jaws 90.1 to 90.n, the manipulating part 42 of the manipulating mechanism 40c is moved relative to the compressing mechanism 10c and, in particular, relative to the housing part 96 on the one hand and the plurality of preferably wedge-shaped clamping jaws 90.1 to 90.n on the other hand, thereby forcing the respective wedge-shaped clamping jaws 90.1 to 90.n to move in the radial direction of the compressing mechanism 10c relative to the housing part 96. For moving the manipulating part 42 relative to the housing part 96 and the preferably wedge-shaped clamping jaws 90.1 to 90.n, a gripper-like mechanism 3 may be used. An exemplary embodiment of such a gripper-like mechanism 3 is depicted in FIG. 37.

Hence, the gripper-like mechanism 3 may comprise a first gripper arm 4 and a second gripper arm 5 which are pivoted together by using a bolt 6. The end section of the first gripper arm 4 and/or the end section of the second gripper arm 5 may be provided with a mounting part 7.1, 7.2, respectively. The mounting part 7.1 of the first gripper arm 4 may be designed such as to receive the manipulating part 42 of the manipulating mechanism 40c. On the other hand, the mounting part 7.2 of the second gripper arm 5 may be designed such as to receive the housing part 96 of the compressing mechanism 10c. In this regard, reference is also made to FIG. 40 which is a perspective view of the gripper-like mechanism 3, which may be utilized in the fourth exemplary embodiment of the disclosed device 1c.

Figure 40:
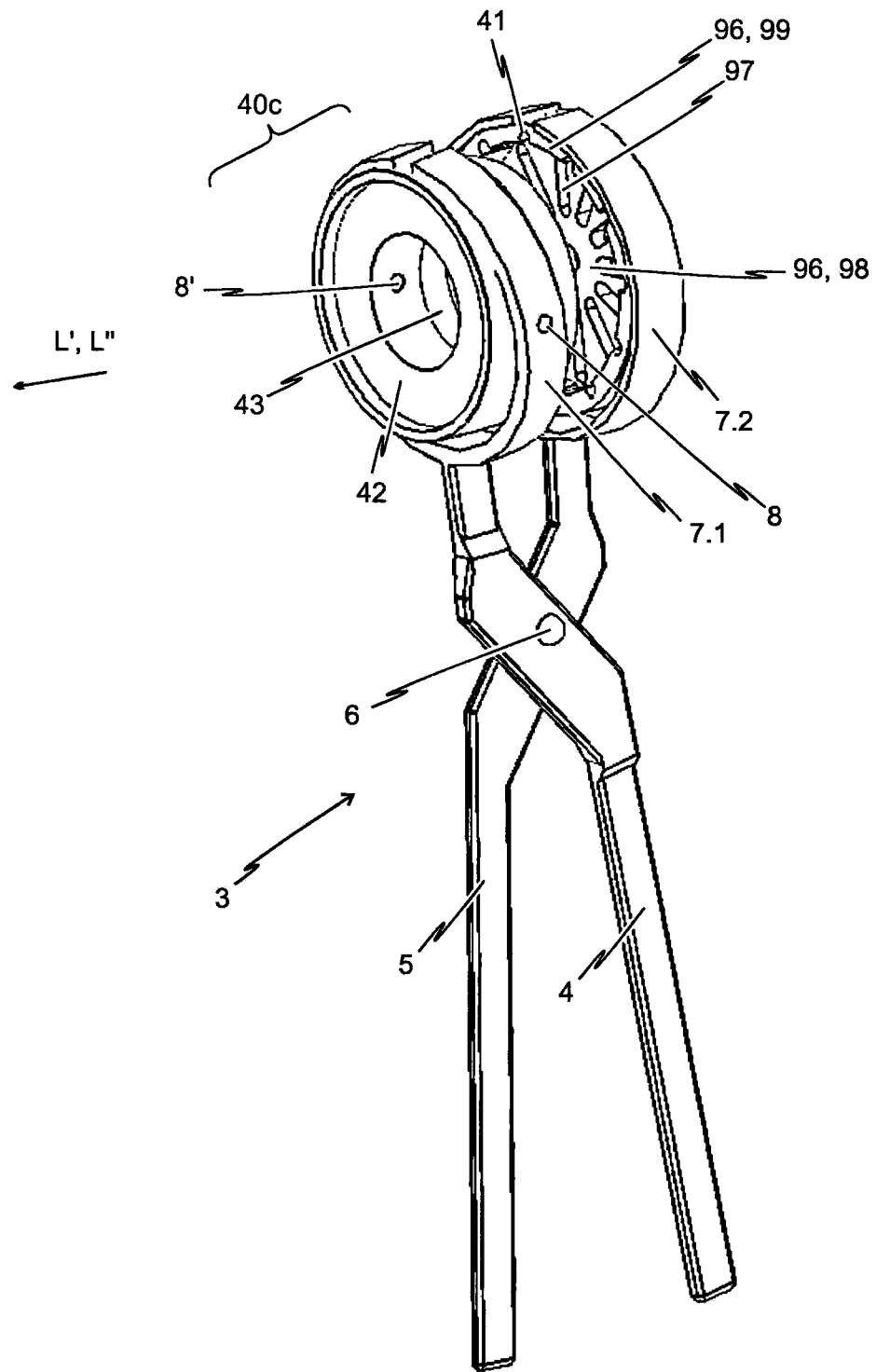
FIG. 40 a perspective view of the gripper-like mechanism utilized in the fourth exemplary embodiment of the disclosed device, wherein a housing part of the compressing mechanism is accommodated in a mounting part provided at an end section of the second gripper arm, and wherein a manipulating part of the manipulating mechanism is accommodated in a mounting part provided at an end section of the first gripper arm.

In detail, in the illustration according to FIG. 40, the housing part 96 of the compressing mechanism 10c is accommodated in the mounting part 7.2 provided at the end section of the second gripper arm 5. On the other hand, the manipulating part 42 of the manipulating mechanism 40c is accommodated in the mounting part 7.1 provided at the end section of the first gripper arm 4.

To axially align the manipulating part 42 and the housing part 96 always with respect to each other, even if the manipulating part 42 is moved in longitudinal direction L of the device 1c relative to the housing part 96, at least the manipulating part 42 or the housing part 96 shall be pivotally attached to the respective gripper arms 4, 5. As can be seen, for example, from FIG. 40, in the fourth exemplary embodiment of the device 1c, the manipulating part 42 is pivotally attached to the mounting part 7.1 provided at the end section of the first gripper arm 4. For this purpose, the mounting part 7.1 is provided with two axially aligned bolts 8 which are adapted to receive a corresponding socket 8' provided in the manipulating part 42 (see FIGS. 38*a*, 38*b* and 40, respectively).

The swivelling axis of the manipulating part 42 is parallel to the swivelling axis of the first and second gripper arms 4, 5 pivoted together by using the already mentioned bolt 6.

As can be seen from FIG. 40, the manipulating part 42 is releasable fixed to the mounting part 7.1 provided at the end section of the first gripper arm 4. Also, the housing part 96 may be releasable fixed to the mounting part 7.2 provided at the end section of the second gripper arm 5.

The device 1*c* according to the fourth exemplary embodiment functions as follows:

The starting point is the device 1*c* according to the fourth exemplary embodiment in its initial state as depicted, for example, in FIG. 35. The stent to be compressed is loaded in the receptacle formed and encircled by the respective wedge surfaces 91 of the preferably wedge-shaped clamping jaws 90.1 to 90.*n* of the compressing mechanism 10*c* such that the stent to be compressed is at least partly accommodated in said receptacle.

For compressing the stent, which is at least partly accommodated in the receptacle, the operator shall manipulate the gripper-like mechanism 3 by crimping the gripper arms 4, 5 of the gripper-like mechanism 3 in the same way as to operate a ordinary gripper. In this regard, the manipulating part 42 of the manipulating mechanism 40*c* is moved in the longitudinal direction L of the device 1*c* relative to the housing part 96 of the compressing mechanism 10*c* which holds the preferably wedge-shaped clamping jaws 90.1 to 90.*n*.

By moving the manipulating part 42 of the manipulating mechanism 40*c* relative to the compressing mechanism 10*c* and, in particular, relative to the preferably wedge-shaped clamping jaws 90.1 to 90.*n* of the compressing mechanism 10*c*, the guiding surface 43 of the manipulating part 42 slides over the respective flange surfaces 92 of the plurality of clamping jaws 90.1 to 90.*n*. During the movement of the manipulating part 42 in the direction of the housing part 96 relative to the housing part 96, the clamping jaws 90.1 to 90.*n* are pushed radially in the direction of the longitudinal axis L of the device 1*c*, since the flange surfaces 92 of the clamping jaws 90.1 to 90.*n* describe a truncated cone which tapers in the direction opposite to the housing part 96. In this respect, the internal cross-sectional diameter of the compressing mechanism 10*c* and, in particular, the internal cross-sectional diameter of the receptacle formed and encircled by the respective wedge surfaces 91 of the clamping jaws 90.1 to 90.*n* of the compressing mechanism 10*c*, is adjusted.

The movement of the manipulating part 42 in the direction of the housing part 96 relative to the housing part 96, and thus the reduction of the internal cross-sectional diameter of the compressing mechanism 10*c* is limited by the stop members 95 provided at the respective end sections of the clamping jaws 90.1 to 90.*n*. Finally, the device 41 is in a state as depicted in FIG. 36.

Thereafter, final loading is then done. For this purpose, a push rod may be used that advances the fully compressed stent into, for example, a delivery catheter. In detail, a the front section of a push rod, for example, a push rod as depicted in FIG. 34, may be inserted into the device 1*c* via the opening 9 provided in the disk-like part 98 of the housing part 96 (see FIG. 41*a*). This allows at least the front section of the push rod to pass through the entire device 1*c*, thereby pushing the stent compressed by the compressing mechanism 10*c* into, for example, a delivery catheter said push rod leadthrough 86 having a diameter which essentially corresponds to the final diameter of the stent 100 after being reduced in the compressing mechanism 10*c*.

According to the fourth exemplary embodiment of the device 1*c* for compressing a stent, the stent accommodated in the compressing mechanism 10*c* of the device 1*c* will be crimped in a single radial motion thereby achieving diameter reduction without having the need to advance the stent forward. This allows only minimal frictional stresses on the stent when adjusting the internal cross-sectional diameter of the compressing mechanism 10*c*.

Reference will be made in the following to FIGS. 43 to 53 in describing a fifth exemplary embodiment of a device 1*d* for compressing a stent 100. Elements in FIGS. 43 to 53 that are generally similar to previously described elements have the same reference numbers compared with the reference numbers in FIGS. 1 to 10 and FIGS. 12 to 42 previously used for the similar elements.

Figure 43:
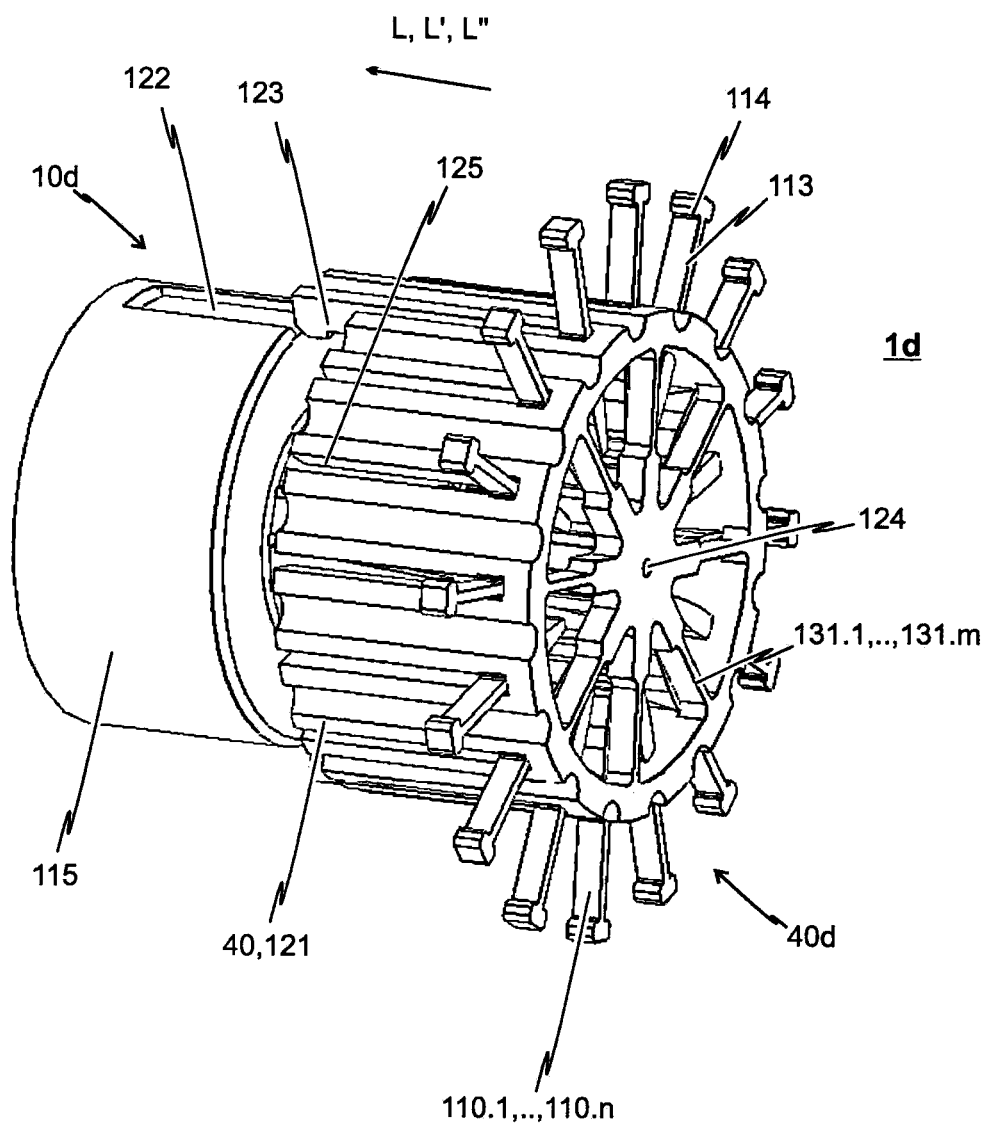
FIG. 43 a perspective view of a fifth exemplary embodiment of the disclosed device for compressing a stent, wherein the device of the fifth exemplary embodiment is shown in its initial state, i.e. prior to activation of the manipulating mechanism of the device according to the fifth exemplary embodiment.
Figure 44A:
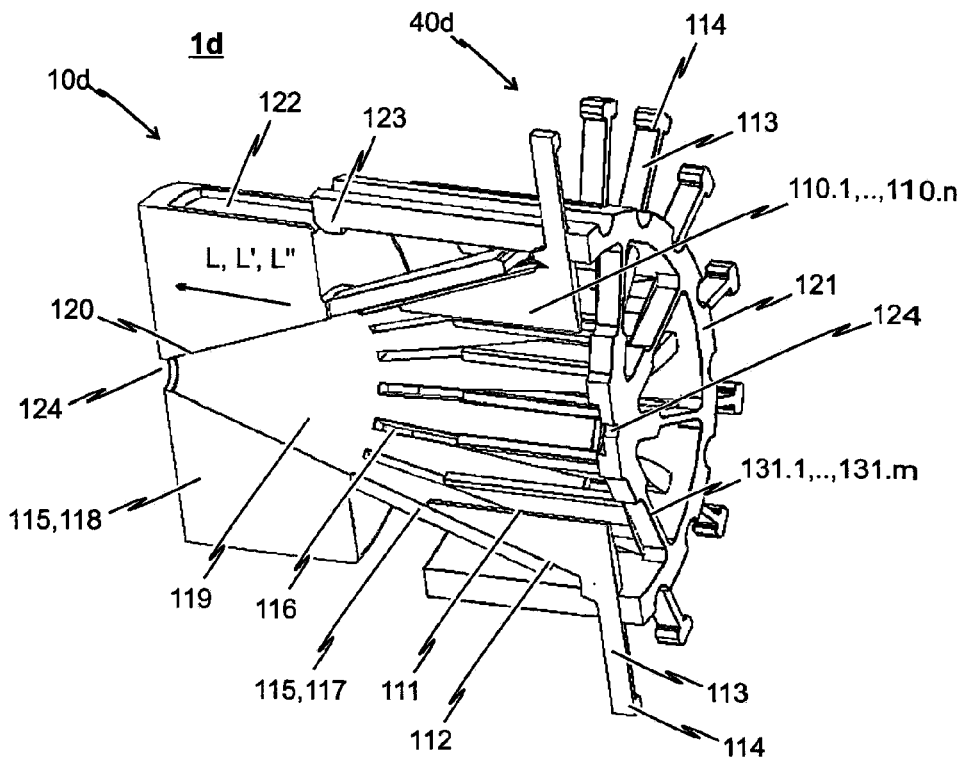
FIG. 44a a sectional view of the device depicted in FIG. 43 without a stent.
Figure 44B:
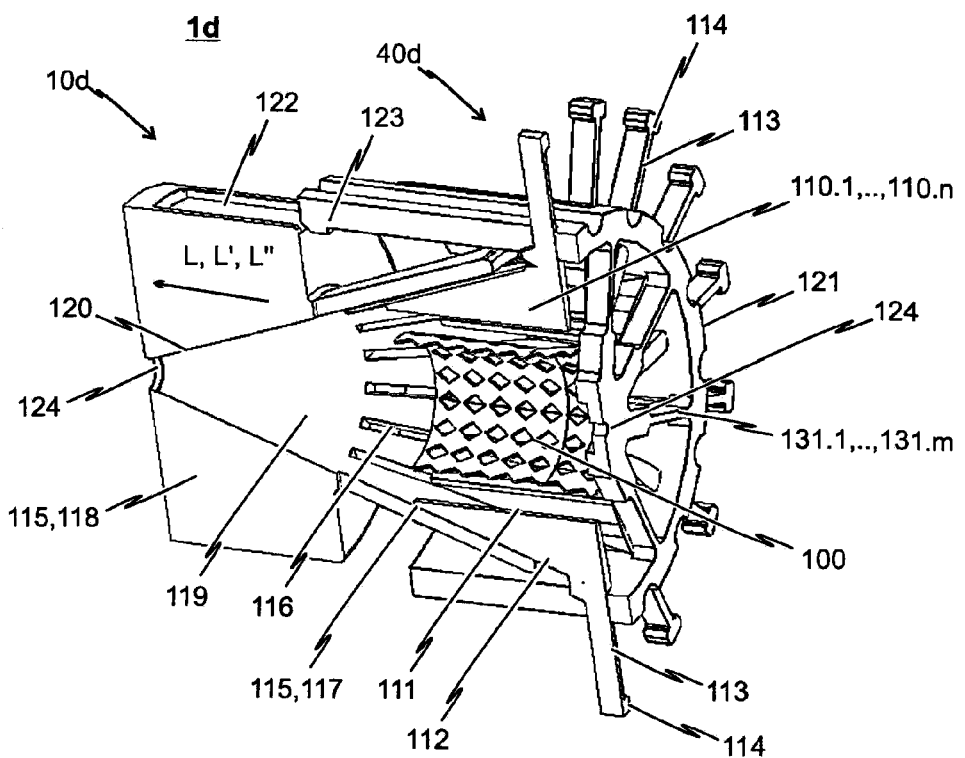
FIG. 44b a sectional view of the device depicted in FIG. 43 with a stent accommodated in the compressing mechanism of the device prior to compressing the stent, wherein the device of the fifth exemplary embodiment is shown in its initial state, i.e. prior to activation of the manipulating mechanism of the device according to the fifth exemplary embodiment.

In detail, FIG. 43 shows a perspective view of the fifth exemplary embodiment of the disclosed device 1*d* for compressing a stent 100, wherein the device 1*d* of the fifth exemplary embodiment is shown in its initial state, i.e. prior to activation of a manipulating mechanism 40*d* of the device 1*d* according to the fifth exemplary embodiment. FIG. 44*a* shows a sectional view of the device 1*d* depicted in FIG. 43 without a stent, whereas FIG. 44*b* shows a sectional view of the device 1*d* depicted in FIG. 43 with a stent 100 to be compressed accommodated in a compressing mechanism 10*d* of the device 1*d* prior to compressing the stent 100.

Figure 45:
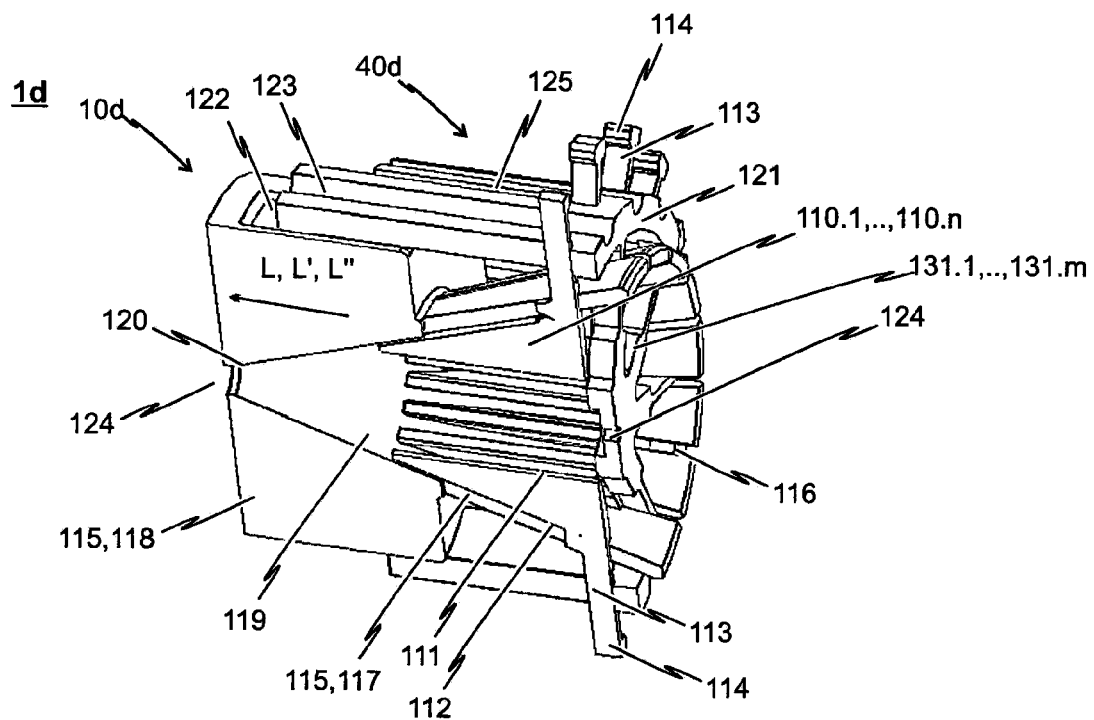
FIG. 45 a sectional view of the fifth exemplary embodiment of the disclosed device for compressing a stent without a stent accommodated in the compressing mechanism of the device immediately after activation of the manipulating mechanism of the device.
Figure 46:
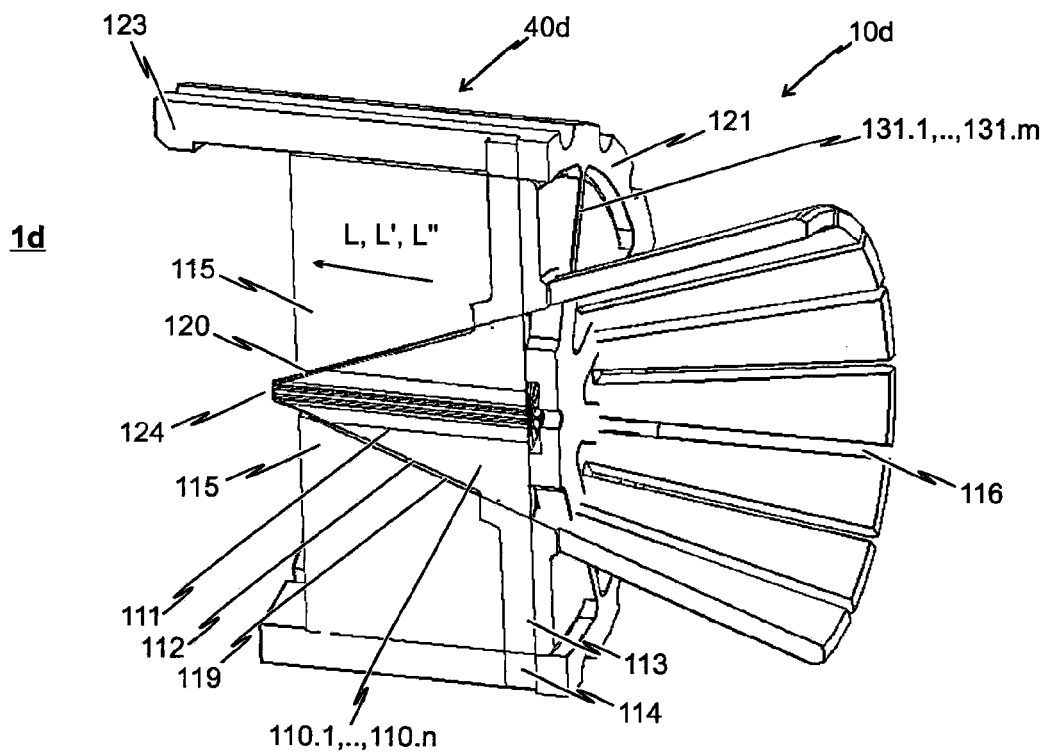
FIG. 46 a sectional view of the fifth exemplary embodiment of the disclosed device for compressing a stent without a stent accommodated in the compressing mechanism of the device after complete activation of the manipulating mechanism of the device.
Figure 47:
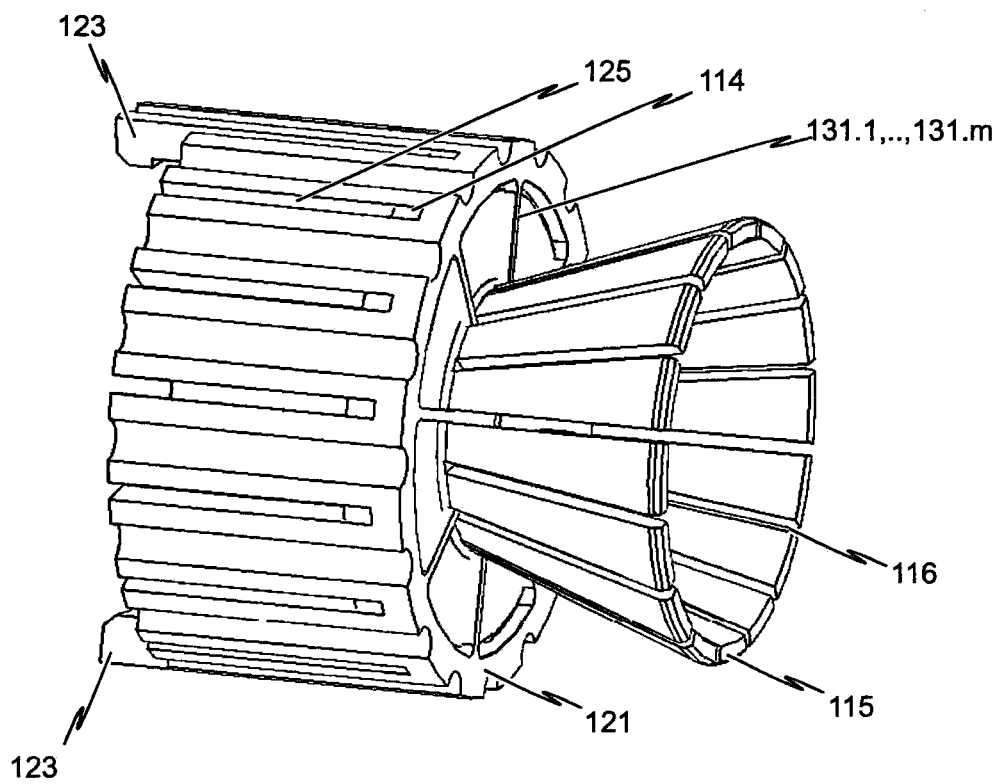
FIG. 47 a perspective view of the fifth exemplary embodiment of the disclosed device for compressing a stent after complete activation of the manipulating mechanism of the device.

On the other hand, FIG. 45 shows a sectional view of the fifth exemplary embodiment of the disclosed device 1*d* without a stent accommodated in the compressing mechanism 10*d* of the device 1*d* immediately after activation of the manipulating mechanism 40*d* of the device 1*d*, and FIG. 46 shows a sectional view of the fifth exemplary embodiment of the disclosed device 1*d* after complete activation of the manipulating mechanism 40*d* of the device 1*d*.

Hence, the device 1*d* according to the fifth exemplary embodiment comprises a compressing mechanism 10*d*, within which a stent 100 to be compressed can be at least partly accommodated. The compressing mechanism 10*d* comprises externally manipulatable clamping means, which consist of a plurality of preferably wedge-shaped clamping jaws 110.1 to 110.*n*.

As will be described in the following, the compressing mechanism 10*d* of the device 1*d* according to the fifth exemplary embodiment is configured such as to exert a compressive force in radial direction on at least parts of a stent 100 accommodated within the compressing mechanism 10*d* such that the cross-section of the stent 100 can be reduced to a predefinable value at least at certain areas. For this purpose, the device 1*d* according to the fifth exemplary embodiment comprises a manipulating mechanism 40*d* for manipulating the clamping means, i.e. the plurality of preferably wedge-shaped clamping jaws 110.1 to 110.*n*.

As shown in FIGS. 45 and 46, the manipulating mechanism 40*d* of the device 1*d* according to the fifth exemplary embodiment is movable relative to the compressing mechanism 10*d* in order to move the preferably wedge-shaped clamping jaws 110.1 to 110.*n* in radial direction thereby adjusting the internal cross-sectional diameter of the compressing mechanism 10*d*.

Figure 51:
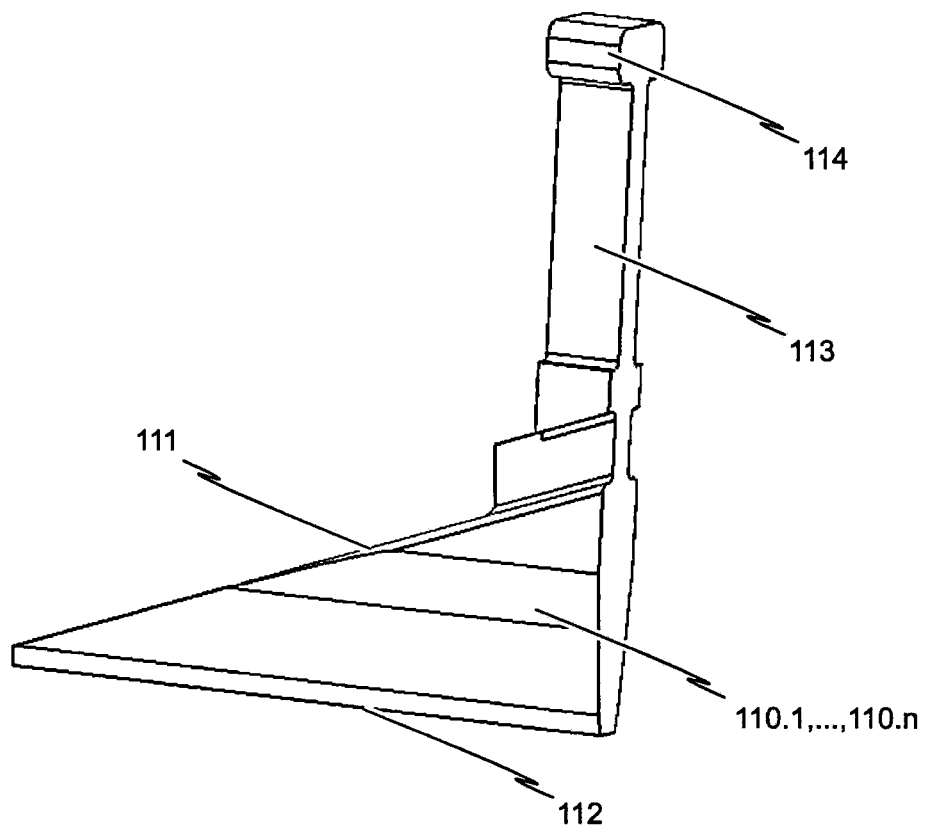
FIG. 51 a perspective view of a single wedge-shaped clamping jaw which serves as clamping means in the compressing mechanism utilized in the fifth exemplary embodiment of the disclosed device for compressing a stent.
Figure 52:
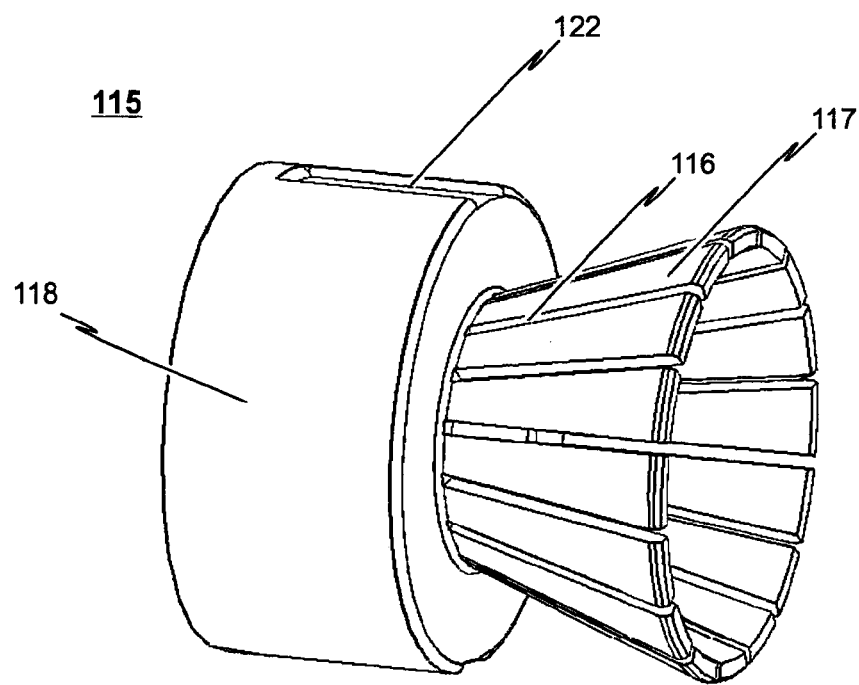
FIG. 52 a perspective view of the housing part of the compressing mechanism utilized in the fifth exemplary embodiment of the disclosed device for compressing a stent without clamping jaws mounted in the housing part.

Reference is made to FIG. 51 which is a perspective view of a single wedge-shaped clamping jaw. As already mentioned, a plurality of such wedge-shaped clamping jaws 110.1 to 110.*n* may serve as clamping means in the compressing mechanism 10*d* utilized in the fifth exemplary embodiment of the disclosed device 1*d* for compressing a stent 100.

Hence, each of the plurality of preferably wedge-shaped clamping jaws 110.1 to 110.*n* may have a wedge surface 111.

As can be seen from FIG. 44a, in the fully assembled state of the compressing mechanism 10d of the device 1d according to the fifth exemplary embodiment, the preferably wedge-shaped clamping jaws 110.1 to 110.n are circumferentially arranged such that the respective wedge surfaces 111 encircle a cavity which serves as receptacle within which a stent 100 to be compressed can be at least partly accommodated. In this regard, reference is also made, for example, to FIG. 44b which is a sectional view of the fifth exemplary embodiment of the disclosed device 1d. In the illustration according to FIG. 44b, a stent 100 to be compressed is accommodated in the compressing mechanism 10d of the device 1d prior to the actual compression of the stent 100.

Figure 53:
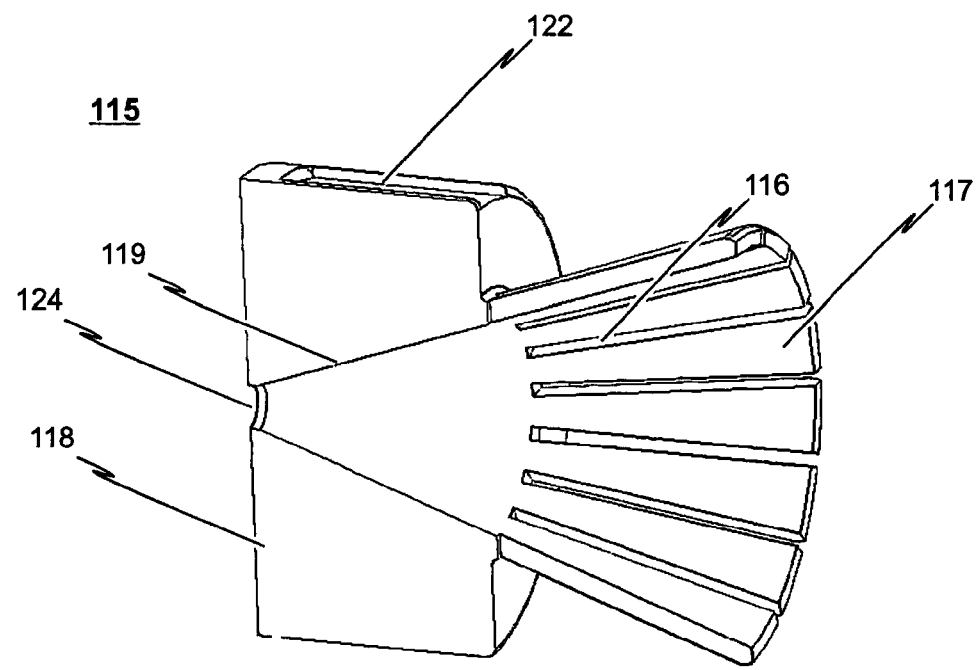
FIG. 53 a sectional view of the housing part depicted in FIG. 52 without a stent accommodated in the housing part.

The device 1d according to the fifth exemplary embodiment may comprise a compressing mechanism 10d having a housing part 115 in which the already mentioned wedge-shaped clamping jaws 110.1 to 110.n are mounted such as to be movable in the longitudinal direction L' of the compressing mechanism 10d relative to the housing part 115. In this respect, reference is made to FIG. 52 which is a perspective view of the housing part 115 of the compressing mechanism 10d utilized in the fifth exemplary embodiment of the disclosed device 1d, however, without clamping jaws 110.1 to 110.n mounted in the housing part 115. On the other hand, FIG. 53 is a sectional view of the housing part 115 depicted in FIG. 52.

Referring to FIGS. 45 and 46, the plurality of preferably wedge-shaped clamping jaws 110.1 to 110.n is mounted in the housing part 115 such as to be movable in the longitudinal direction L' of the compressing mechanism 10d relative to the housing part 115. In particular, according to the illustrations depicted in FIGS. 45 and 46, the plurality of wedge shaped clamping jaws 110.1 to 110.n is in a state after activation of the manipulating mechanism 40d belonging to the device 1d of the fifth exemplary embodiment.

In contrast, FIG. 44a shows a sectional view of the housing part 115 of the compressing mechanism 10d utilized in the fifth exemplary embodiment of the disclosed device 1d, wherein the preferably wedge-shaped clamping jaws 110.1 to 110.n mounted in the housing part 115 are in their initial state, i.e. prior to activation of the manipulating mechanism 40d.

Accordingly, the housing part 115 of the compressing mechanism 10d utilized in the fifth exemplary embodiment of the device 1d may be provided with a plurality of guiding slits 116 which extend in the longitudinal direction L' of the compressing mechanism 10d. As can be seen from the illustrations in FIGS. 44a, 45 and 46, each of the plurality of guiding slits 116 interacts with one of the plurality of preferably wedge-shaped clamping jaws 110.1 to 110.n for guiding the wedge-shaped clamping jaw 110.1 to 110.n during its movement in the longitudinal direction L' of the compressing mechanism 10d relative to the housing part 115.

Again, reference is made to FIG. 51, which is a perspective view of a single wedge-shaped clamping jaw utilized in the fifth exemplary embodiment of the disclosed device 1d. Hence, each of the preferably wedge-shaped clamping jaws 110.1 to 110.n may have at least one protruding part 113 provided on the clamping jaw's surface 112 which is opposite to the wedge surface 111. As can be seen from the illustrations in FIGS. 44a, 45 and 46, this protruding part 113 may be engaged with the guiding slit 116 allocated to the respective clamping jaw 110.1 to 110.n in the assembled state.

As can be seen, in particular, from FIG. 53, the housing part 115 of the compressing mechanism 10d utilized in the fifth exemplary embodiment of the device 1d may be divided into a first housing section 117 and a second housing section 118. The guiding slits 116 are only provided in the circumferential surface of the first housing section 117. On the other hand, the inner circumferential surface of the first housing section 117 is tapered towards the second housing section 118.

Preferably, the inclination angle of the inner circumferential surface of the first housing section 117 corresponds to the angle α between the wedge surface 111 of one of the plurality of preferably wedge-shaped clamping jaws 110.1 to 110.n and the surface 112 of the preferably wedge-shaped clamping jaws 110.1 to 110.n which is opposite to the wedge surface 111. In this regard, reference is also made to FIG. 51.

On the other hand, the inner circumferential surface of the second housing section 118 is also tapered in the same direction as the inner circumferential surface of the first housing section 117 and terminates at a cone 120.

Alternatively, the inner circumferential surface of the second housing section 118 may be at least essentially cylindrical, wherein, for each of the plurality of preferably wedge-shaped clamping jaws 110.1 to 110.n, a rail element (not shown) may be provided on the inner circumferential surface of the second housing section 118.

As can be seen, for example, from the illustrations in FIGS. 44a, 45 and 46, the inner circumferential surface of the second housing section 118 serves as guiding surface 119 for guiding the clamping jaws 110.1 to 110.n during their movement in the longitudinal direction L' of the compressing mechanism 10d relative to the housing part 115.

Preferably, the intersection between the first and second housing sections 117 and 118 is without any steps. Hence, the inclination angle of the inner circumferential surface of the first and second housing sections 117 and 118 shall be identical. As already mentioned, this inclination angle preferably corresponds to the angle α between the wedge surface 111 of one of the plurality of preferably wedge-shaped clamping jaws 110.1 to 110.n and the surface 112 of the preferably wedge-shaped clamping jaws 110.1 to 110.n which is opposite to the wedge surface 111 (see FIG. 51).

Reference is made in the following in particular to FIGS. 44a, 45 and 46 for describing the manipulating mechanism 40d which may be utilized in the fifth exemplary embodiment of the device 1d. In the illustrations of FIGS. 44a and 44b, the preferably wedge-shaped clamping jaws 110.1 to 110.n mounted in the housing part 115 are respectively in their initial state, i.e. prior to activation of the manipulating mechanism 40d belonging to the device 1d according to the fifth exemplary embodiment. On the other hand, FIGS. 45 and 46 respectively show a sectional view of the device 1d depicted in FIG. 44a, wherein the clamping jaws 110.1 to 110.n mounted in the housing part 115 are in a state after activation of the manipulating mechanism 40d.

In detail, according to the fifth exemplary embodiment of the device 1d, the manipulating mechanism 40d may comprise a manipulating part 121. The manipulating part 121 may have an essentially cup-shaped configuration which is adapted to receive the housing part 115 of the compressing mechanism 10d in a releasable manner by attaching the manipulating part 121 axially aligned.

A comparison of FIG. 44a on the one hand and FIGS. 45 and 46 on the other hand shows that, according to the fifth exemplary embodiment of the device 1d, the manipulating part 121 of the manipulating mechanism 40d is moveable relative to the housing part 115 of the compressing mechanism 10d, wherein the manipulating part 121 interacts with the plurality of preferably wedge-shaped clamping jaws 110.1 to 110.n mounted in the housing part 115 of the compressing mechanism 10d such that, by moving the manipulating part 121 relative to the housing part 115 in the longitudinal direction L' of the compressing mechanism 10d, the plurality of preferably wedge-shaped clamping jaws 110.1 to 110.*n* is moved in the longitudinal direction L' of the compressing mechanism 10*d* relative to the housing part 115 of the compressing mechanism 10*d*.

For this purpose, each of the plurality of preferably wedge-shaped clamping jaws 110.1 to 110.*n* may have—as depicted in particular in FIG. 51—a head portion 114 provided on the surface 112 of the clamping jaw 110.1 to 110.*n* which is opposite to the respective wedge surface 111. The respective head portions 114 of the plurality of preferably wedge-shaped clamping jaws 110.1 to 110.*n* protrude from the outer circumferential surface of the housing part 115 of the compressing mechanism 10*d* when these clamping jaws 110.1 to 110.*n* are mounted in the housing part 115.

As can be seen, in particular, from the illustration of FIG. 43, the manipulating part 121 of the manipulating mechanism 40*d* utilized in the fifth exemplary embodiment of the device 1*d* may be provided with a plurality of dedicated slits 125, each of which extends in the longitudinal direction L" of the manipulating part 121. These dedicated slits 125 are designed such as to fit the head portions 114 of the preferably wedge-shaped clamping jaws 110.1 to 110.*n* and to lock them in place. In this regard, reference is also made to FIG. 47 which is a perspective view of the fifth exemplary embodiment of the disclosed device 1*d* after complete activation of the manipulating mechanism 40*d*.

The manipulating part 121 of the manipulating mechanism 40*d* utilized in the fifth exemplary embodiment of the device 1*d* may also be provided with a plurality of radial arms 131.1 to 131.*m*. For each of the plurality of dedicated slits 125 one of the plurality of radial arms 131.1 to 131.*m* may be allocated. However, in the embodiment depicted in FIGS. 43 to 50, only for every other of the dedicated slits 125 one radial arm 131.1 to 131.*m* is provided.

When the manipulating part 121 is attached to the housing part 115, the radial arms 130.1 to 130.*n* do not abut on the clamping jaws 110.1 to 110.*n* whose protruding parts 113 with the head portions 114 pass through the dedicated slits 125. Rather, the radial arms 131.1 to 131.*m* of the manipulating part 121 may abut on the stent 100 accommodated in the cavity encircled by the respective wedge surfaces 111 of the clamping jaws 110.1 to 110.*n*. In this respect, reference is made to FIG. 44*b*.

Hence, when moving the cup-shaped manipulating part 121 relative to the housing part 115 in the direction of the housing part 115, the manipulating part 115 pushes the clamping jaws 110.1 to 110.*n* in the longitudinal direction because, during the movement of the manipulating part 121, the protruding parts 113 of the clamping jaws 110.1 to 110.*n* remain engaged with the dedicated slits 125 provided in the manipulating part 121. At the same time, the radial arms 131.1 to 131.*m* of the manipulating part 121 push the stent 100 accommodated within the housing part 115 in the longitudinal direction.

Figure 48:
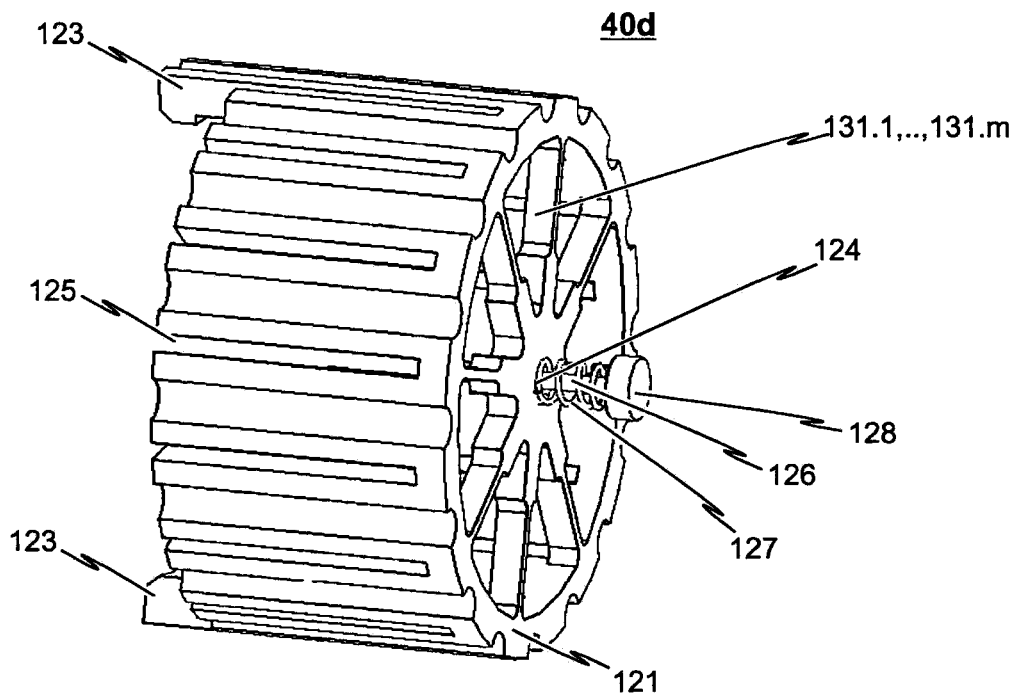
FIG. 48 a perspective view of a manipulating part of the manipulating mechanism which may be utilized in the fifth exemplary embodiment of the disclosed device for compressing a stent.
Figure 49:
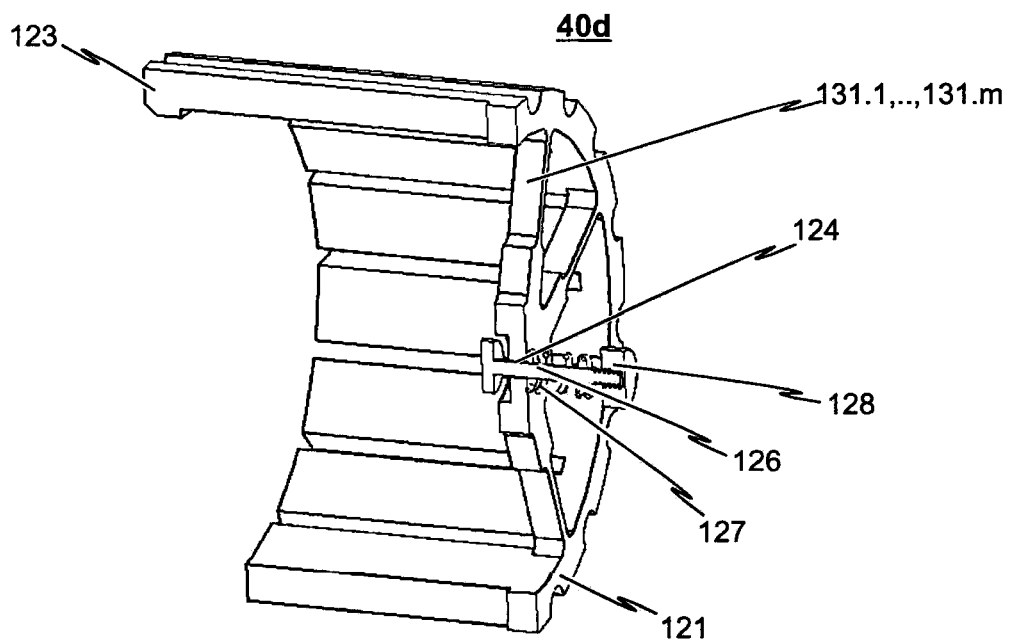
FIG. 49 a sectional view of the manipulating part depicted in FIG. 48.

Reference is made in the following to FIGS. 48 and 49 for describing a specific embodiment of a manipulating part 121 which may be utilized in the fifth exemplary embodiment of the disclosed device 1*d*. In detail, FIG. 48 shows a perspective view of the specific embodiment of the manipulating part 121, whereas FIG. 49 shows a sectional view of the manipulating part 121 depicted in FIG. 48.

Figure 50:
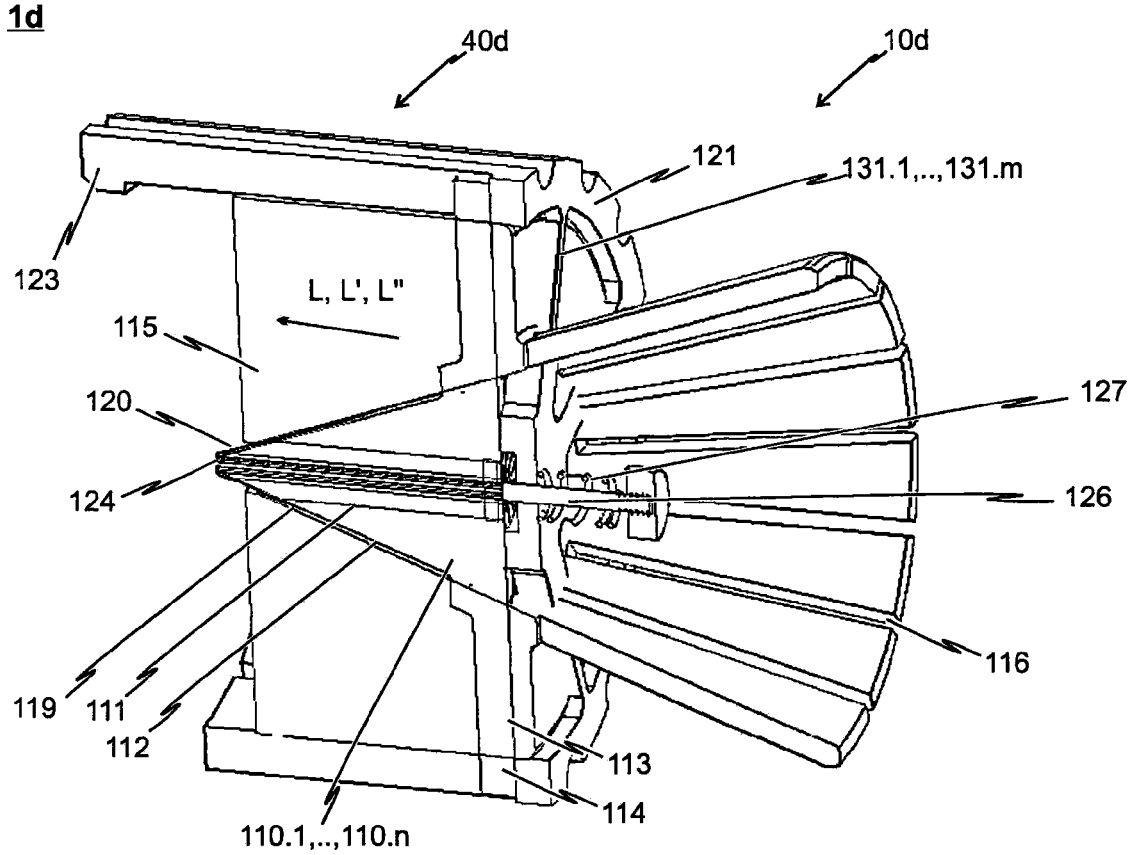
FIG. 50 a sectional view of the fifth exemplary embodiment of the disclosed device for compressing a stent without a stent accommodated in the compressing mechanism of the device after complete activation of the manipulating mechanism of the device, wherein the manipulating mechanism comprises a manipulating part as depicted in FIGS. 48 and 49.

As depicted in FIG. 50, the housing part 115 of the compressing mechanism 10*d* may further incorporate a cone 120 that allows a final diameter reduction to the desired delivery catheter. Final loading is then done using the plunger mechanism by means of which a stent 100 compressed by the compressing mechanism 10*d* can be removed from the device 1*d* and loaded, for example, in a catheter tip 105.1 or 105.2 of a catheter delivery system (see FIGS. 54 and 55).

As can be seen, for example, from FIGS. 48 and 49, the manipulating part 121 according to this exemplary embodiment may have a plunger mechanism comprising a bolt like part 126, a spring 127 and a locking disk 128. The bolt like part 126 is received in an axial lead through 124 provided in the front face of the cup-shaped manipulating part 121.

The plunger mechanism may be used for pushing the stent 100 through the cone 120 which is provided at the end of the second housing section 118 opposite to the first housing section 117 of the housing part 115 (see FIG. 53).

Preferably, the plunger mechanism is designed such that the bolt like part 126 has enough travel to push a stent 100 compressed by the compressing mechanism 10*d* only partly through the cone 120. Pushing the stent 100 only partly through the cone 120 allows that the stent 100 is locally crimped at its distal end section pointing toward the catheter tip 105.1, 105.2 of the delivery system. In this respect, fastening means of the stent 100 provided at the distal end section of the stent 100, for example, retaining elements in the form of eyelets, can be easily connected with complementary fastening means of the catheter tip 105.1, 105.2, for example, retaining elements 151 of a stent holder 150 (see FIG. 54).

After releasably connecting the distal end section of the stent 100 with the stent holder 150 of the catheter tip 105.1, 105.2, the operator of the device 1*d* is able to pull the stent 100 into the proximal body and of the catheter tip 105.1, 105.2 which has a sleeve-like member to encapsulate the compressed stent 100 accommodated in the catheter tip 105.1, 105.2.

As depicted, for example, in FIGS. 48 and 49, the cup-shaped manipulating part 121 of the manipulating mechanism 40*d*, which may be utilized in the device 1*d* according to the fifth embodiment, may comprise at least one securing member 123 for locking the manipulating part 121 in place relative to the housing part 115 after the internal cross-sectional diameter of the compressing mechanism 10*d* has been reduced to a predefinable intermediate diameter, i.e. a diameter less than the diameter of the compressing mechanism 10*d* in its initial state (prior to activation of the manipulating mechanism 40) and greater than the minimal diameter of the compressing mechanism 10 (after complete activation of the manipulating mechanism 40). The manipulating part 121 of the device 1*d* according to the fifth exemplary embodiment as depicted in FIGS. 43 to 53 is provided with two securing members 123, each of the securing members 123 being realized as teeth-like extensions.

On the other hand, the housing part 151, which may be utilized in the device 1*d* according to the fifth exemplary embodiment, is provided with corresponding grooves 122 located on opposite sides of the housing part 115. Each of these grooves 122 is adapted to receive one of the teeth-like extensions 123. In this respect, reference is made, for example, to FIGS. 44*a, b* and 45.

When manipulating the manipulating mechanism 40*d* of the device 1*d* according to the fifth embodiment, i.e. when moving the cup-shaped manipulating part 121 relative to the housing part 115, the teeth-like extensions 123 provided at the manipulating part 121 slide in the corresponding grooves 122 located on opposite sides of the housing part 115. In particular, the teeth-like extensions 123 slide till they reach the edge of the housing part 115 and lock in place. At this stage, the internal cross-sectional diameter of the compressing mechanism 10*d* has been reduced to an intermediate diameter which is between the minimal cross-sectional diameter of the compressing mechanism 10*d* after complete activation of the manipulating mechanism 40*d* and the internal cross-sectional diameter of the compressing mechanism 10*d* prior to activation of the manipulating mechanism 40*d*. Hence, a stent 100 accommodated within the compressing mechanism 10*d* is crimped to an intermediate diameter while being secured inside the housing part 115.

Since the manipulating part 121 is locked in place due to the at least one securing member 123 shaped, for example, as teeth-like extension, the operator of the device 1*d* is now free to insert a catheter tip 105.1, 105.2 of a catheter delivery system into the receptacle formed by the clamping jaws 110.1 to 110.*n* of the compressing mechanism 10*d*.

Thereafter, the operator of the device 1*d* should move the manipulating part 121 further relative to the housing part 115 thereby adjusting the internal cross-sectional diameter of the compressing mechanism 10*d* to its minimal diameter. At the same time, the stent 100 accommodated within the compressing mechanism 10*d* is further crimped to a final diameter.

Thereafter, the operator of the device 1*d* should press the plunger mechanism which forces the stent 100 to go through the conical section 120 of the housing part 115 that it further reduces the stent diameter and will allow it to load onto the delivery system head.

It is important to note that, for releasing the manipulating part 121 from the housing part 115, the operator needs to bend both securing members 123 forcing the teeth-like extensions to be on or above the plane of the grooves 122, and then pull back the manipulating part 121.

Briefly summarized, the device 1*d* according to the fifth exemplary embodiment may comprise a compressing mechanism 10*d* having a housing part 115 and a plurality of preferably wedge-shaped clamping jaws 110.1 to 110.*n*. Furthermore, the fifth exemplary embodiment of the device 1*d* may comprise a manipulating part 121 belonging to a manipulating mechanism 40*d*.

The device 1*d* according to the fifth exemplary embodiment functions as follows:

First of all, the operator should load the stent 100 to be compressed into the housing part 115 of the compressing mechanism 10*d*. By using the cup-shaped manipulating part 121 of the manipulating mechanism 40*d*, the stent 100 may be locked in place. The cup-shaped manipulating part 121 has dedicated slits 125 to secure the stent 100 accommodated in the housing part 115 and to allow only minimal stresses when advancing the manipulating mechanism 40*d* of the device 1*d*, i.e. when moving/pushing the manipulating part 121 of the manipulating mechanism 40*d* in the longitudinal direction L of the device 1*d* relative to the compressing mechanism 10*d* in order to move the preferably wedge-shaped clamping jaws 110.1 to 110.*n* in the radial direction of the device 1*d* thereby adjusting the internal cross-sectional diameter of the compressing mechanism 10*d*.

In particular, for manipulating the preferably wedge-shaped clamping jaws 110.1 to 110.*n* of the compressing mechanism 10*d*, the preferably cup-shaped manipulating part 121 has dedicated slits 125 to fit the head portions 114 of the preferably wedge-shaped clamping jaws 110.1 to 110.*n* and to lock them in place.

In detail, for manipulating the preferably wedge-shaped clamping jaws 110.1 to 110.*n* of the compressing mechanism 10*d*, the operator should push forward the cup-shaped manipulating part 121 relative to the housing part 115. This will cause the clamping jaws 110.1 to 110.*n* to slide forward in the longitudinal direction L of the device L relative to the housing part 115 of the compressing mechanism 10 and along with the cup-shaped manipulating part 121 of the manipulating mechanism 40*d*.

As already discussed, when activating the manipulating mechanism 40*d*, the clamping jaws 110.1 to 110.*n* slide inside the housing part 115 of the compressing mechanism 10*d* in dedicated angled rails 80. This design causes continues inner diameter reduction while the cup-shaped manipulating part 121 is pushed forward.

According to the fifth exemplary embodiment of the device 1*d* for compressing a stent 100, the stent 100 accommodated in the compressing mechanism 10*d* of the device 1*d* will be crimped in a combined motion: diameter reduction while being advanced forward.

Preferably, the device 1*b-d* according to the third, fourth and fifth embodiments comprise a plurality of clamping jaws 70.1-70.*n*; 90.1-90.*n*, 100.1-100.*n* in particular, more than six clamping jaws, which are circumferentially arranged such that the respective wedge surfaces 71; 91; 111 of the of clamping jaws 70.1-70.*n*; 90.1-90.*n*; 100.1-100.*n* encircle a cavity which serves as receptacle within which a stent 100 to be compressed can be at least partly accommodated. In this regard, the compressive force exerted in radial direction on at least parts of a stent 100 accommodated within the receptacle of the compressing mechanism 10*c-d* can be equally distributed of the circumferential surface of the stent 100, when reducing the cross-section of the stent 100 to a predefinable value at least at certain areas.

In general, the individual components of the embodiments described herein can be made, at least partly, of plastic material. The components made of plastic material can at least partly be manufactured by injection moulding. This applies for all embodiments of the device 1, 1*a*, 1*b*, 1*c*, 1*d* disclosed herein.

On the other hand, at least some of the individual components may be made of another material, for example, stainless steel, and in particular acid- and corrosion-resistant steel. Also, this applies for all embodiments of the device 1, 1*a*, 1*b*, 1*c*, 1*d* disclosed herein.

Figure 11A:
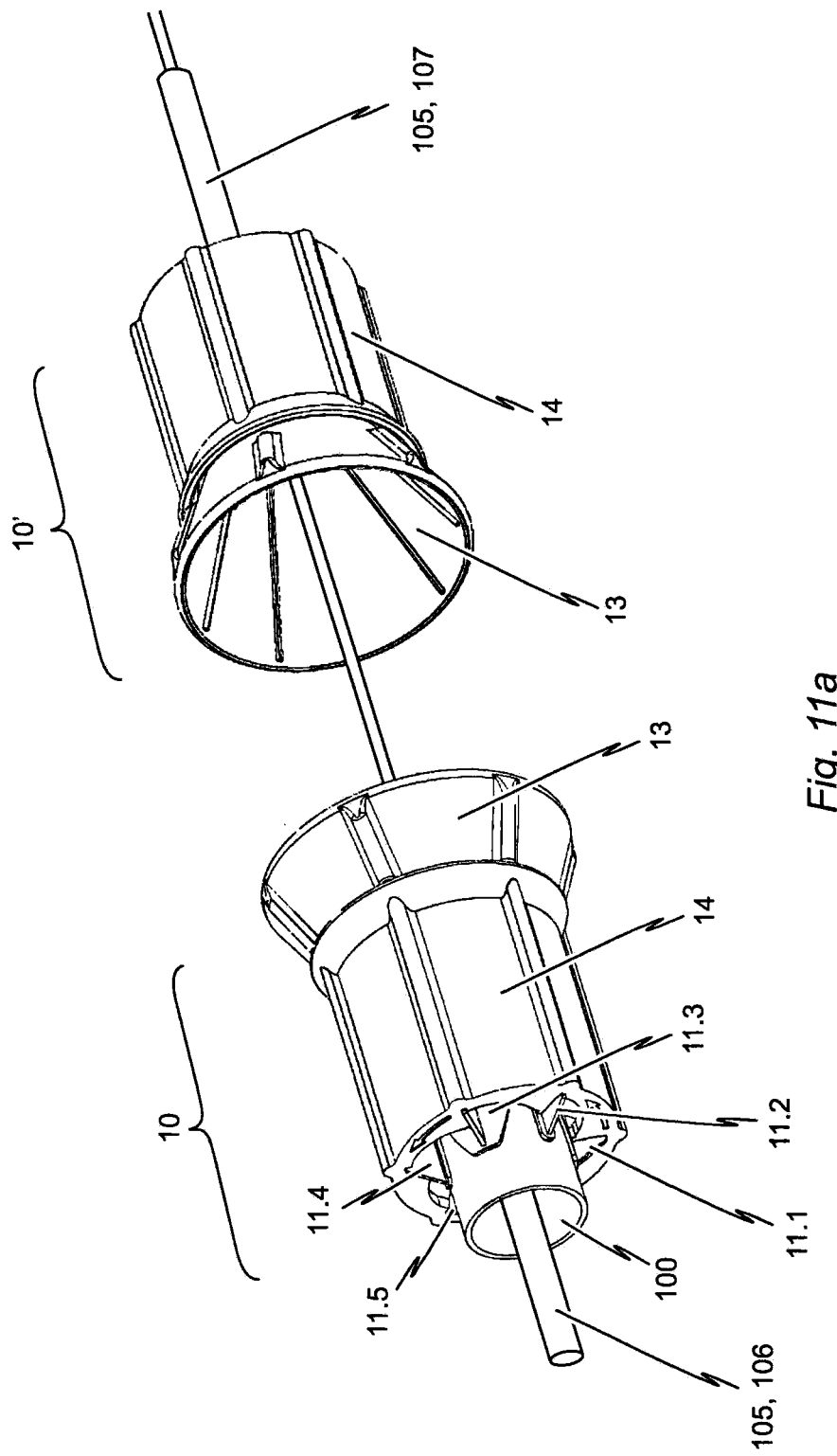
FIG. 11a-c perspective views of an exemplary embodiment of the system illustrating the loading of a stent into the catheter tip of a medical delivery system.
Figure 11B:
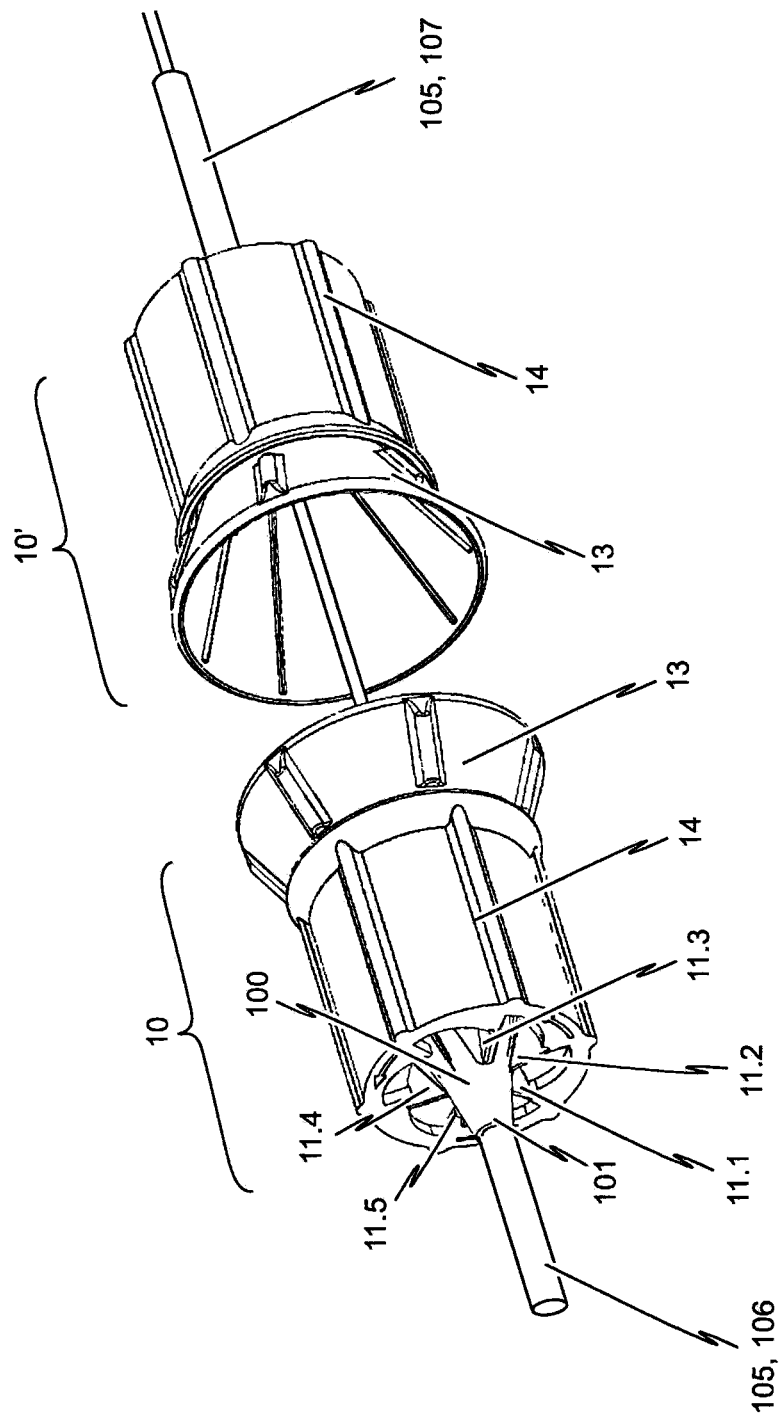
Figure 11C:
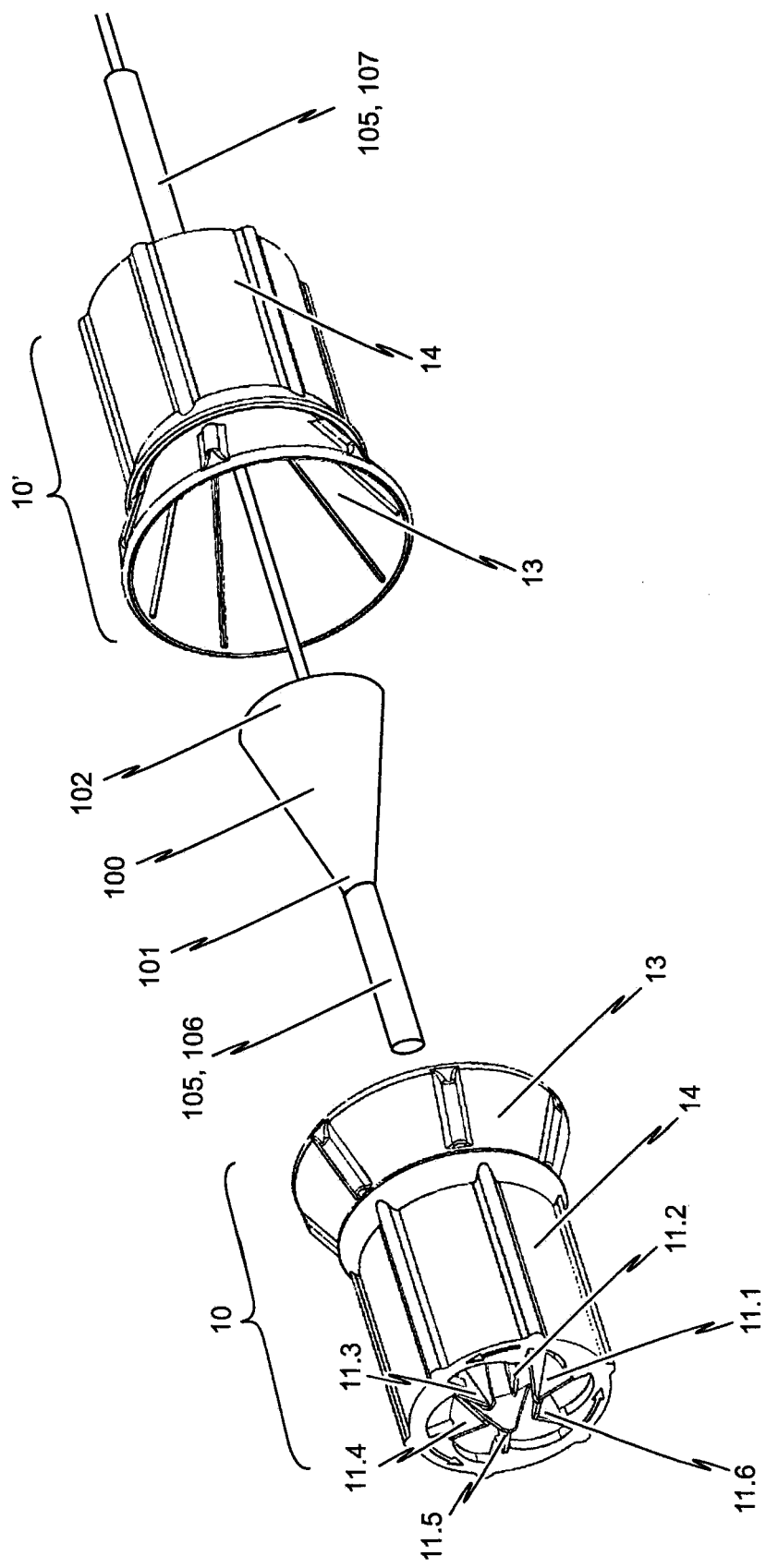

The functioning of an exemplary embodiment of the system for loading a stent 100 into the catheter tip 105 of a medical delivery system will be described in the following referencing the FIG. 1*la* to FIG. 11*c* representations. Elements in FIGS. 1*la* to 11*c* that are generally similar to previously described elements have the same reference numbers compared with the reference numbers in FIGS. 1 to 10 and FIGS. 12 to 42 previously used for the similar elements.

In the exemplary embodiment depicted in FIGS. 1*la* to 11*c*, a stent 100 is loaded in the catheter tip 105 of a medical delivery system designed for a transapical approach, although the system for loading a stent is of course also designed for a transfemoral or transarterial delivery system. In a medical delivery system designed for a transapical approach, the stent 100, as needed with the prosthetic heart valve affixed thereto, is advanced from the apex of the heart to the implantation site in the heart. In a medical delivery system designed for a transarterial or transfemoral approach, the stent 100, as needed with the prosthetic heart valve likewise affixed thereto, is advanced to the implantation site through the aorta of a patient to be treated.

The exemplary embodiment of the system for loading a stent 100 into the catheter tip 105 of a medical delivery system as depicted in FIGS. 1*la* to 11*c* comprises a device 1 as previously described when referencing the representations provided in FIGS. 1 to 10. A device 1 is thus used to compress a stent 100, whereby the device 1 comprises a compressing mechanism 10 as well as a gripping mechanism 20.

To load the stent 100 into the catheter tip 105 of the medical delivery system, the gripping mechanism 20 first inserts the stent 100 into the compressing mechanism 10, as has been described in detail referencing FIGS. 10*a* to 10*f*.

Prior to the compressing mechanism 10 effecting the compressing of the stent 100, the catheter tip 105 of the medical delivery system is first introduced through the compressing mechanism 10 and then the precompressed stent 100 in the compressing mechanism 10. Not until that point is the stent 100 accommodated in the compressing mechanism 10 actually compressed by manipulating the clamping jaws 11.1 to 11.6, as described above referencing FIGS. 6 to 9*b*.

As depicted in FIG. 11*b*, the clamping area 14 of the compressing mechanism 10 is displaced relative the funnel-shaped area 13—after the catheter tip 105 of the medical delivery system has been inserted at least partly through the compressing mechanism—such that the upper end 101 of the stent 100 accommodated in the compressing mechanism 10 is compressed to its final external diameter. The final external diameter of the upper end section 101 of stent 100 is dependent on the respective catheter tip 105.

After the upper end section 101 of stent 100 has been compressed to its final diameter by means of the compressing mechanism 10, the upper end section 101 of stent 100—as shown in FIG. 10*b*—is releasably affixed to the catheter tip 105.

For example, it is conceivable for the catheter tip 105—as will be described below referencing the depictions provided in FIGS. 54 and 55—to comprise a stent holder 150 for releasably fixing the upper end section 101 of the stent 100. The distal end section 101 of stent 100 compressed to its final diameter can then be introduced into stent holder 150 (cf. FIGS. 54 and 55) by means of the compressing mechanism 10 and fixed there.

To releasably fix the upper end section 101 of stent 100 to the catheter tip 105, it is for example further conceivable to make use of a first sleeve-shaped element 106 (cf. FIGS. 11*a* to 11*c*) which draws over the upper end section 101 of the stent 100 as soon as the upper end section 101 of the stent 100 is affixed to the catheter tip 105. The examples of the catheter tips 105-1 and 105-2 depicted in FIGS. 54 and 55 respectively provide for the upper end section 101 of stent 100 compressed to its final diameter by means of the compressing mechanism 10 to be introduced into the stent holder 150 and thereafter a sleeve-shaped receiving area (first receiving area 111) to draw over the stent holder 150.

After the compressed upper end section 101 of stent 100 is fixed to the catheter tip 105 by means of the compressing mechanism 10, the compressing mechanism 10 is—as shown in FIG. 11*c*—removed from the catheter tip 105 of the medical delivery system. To this end, the clamping jaws 11.1 to 11.6 of the compressing mechanism 10 are manipulated such that the clamping jaws 11.1 to 11.6 are radially moved perpendicular to the longitudinal axis of the compressing mechanism 10 relative said compressing mechanism 10. This occurs in that the clamping area 14 of the compressing mechanism 10 is again rotated relative the funnel-shaped area 13, whereby however this time the direction of rotation is different from the direction of rotation when compressing the stent 100.

In order to also have the proximal end section 102 of the stent 100 be compressed and be accommodated in the catheter tip 105 of the medical delivery system, the system as depicted in FIGS. 11*a* to 11*c* comprises a further compressing mechanism 10'. Structurally and functionally, this supplementary compressing mechanism 10' can be configured similar to the compressing mechanism 10 employed in the exemplary embodiment of the device 1 as described previously referencing the representations of FIGS. 1 to 9*b*.

In order to be able to load a stent 100 into the catheter tip 105 of a medical delivery system designed for a transapical approach, the catheter tip 105 of the medical delivery system first needs to be guided through the supplementary compressing mechanism 10' and thereafter through the compressing mechanism 10, within which the already precompressed stent 100 is accommodated, as shown in FIGS. 11*a* to 11*c*. In detail, the supplementary compressing mechanism 10' is positioned relative the compressing mechanism 10 such that the supplementary compressing mechanism 10' abuts the proximal end section 102 of the stent 100 accommodated at least partly inside the compressing mechanism 10.

After the compressing mechanism 10 is removed from the catheter tip 105 of the medical delivery system—as shown in FIG. 11*c*—the supplementary compressing mechanism 10' is moved toward the proximal end section 102 of the stent 100 such that at least the proximal end section 102 of the stent 100 is accommodated at least partly within said supplementary compressing mechanism 10'. The proximal end section 102 of stent 100 can then be compressed, which is done by the clamping jaws 11.1 to 11.6 manipulating the supplementary compressing mechanism 10' such that said clamping jaws 11.1 to 11.6 move radially relative the supplementary compressing mechanism 10' in the direction of the longitudinal axis of said supplementary compressing mechanism 10'. The proximal end section 102 of stent 100 thus compressed to the desired diameter can then be accommodated in the catheter tip 105 of the medical delivery system. For example, it is conceivable to provide at least one second sleeve-shaped element 107 guided over the compressed proximal end section 102 of stent 100 such that the proximal end section 102 of stent 100 is held in its compressed form and connected to the catheter tip 105 of the medical delivery system.

Figure 54:
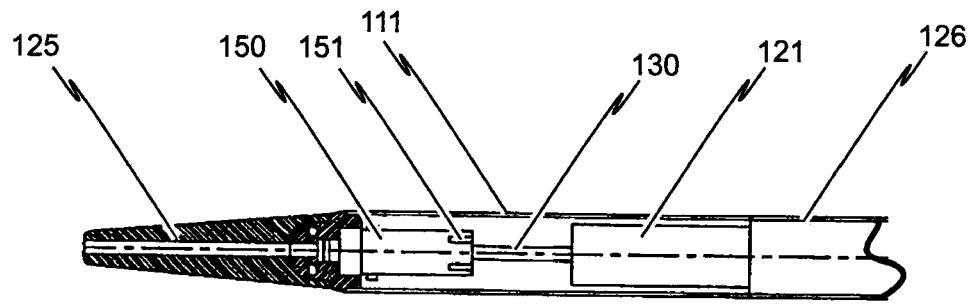
FIG. 54 a side view of an exemplary embodiment of a catheter tip of a medical delivery system for transapically introducing a stent.
Figure 55:
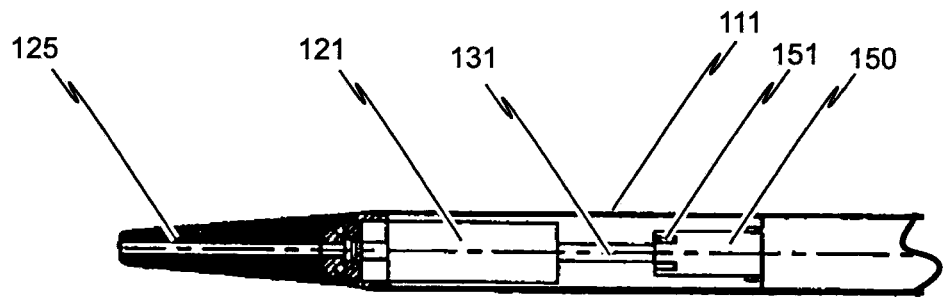
FIG. 55 a side view of an exemplary embodiment of a catheter tip of a medical delivery system for transfemorally/transarterially introducing a stent

The examples of the catheter tips 105-1 and 105-2 depicted in FIGS. 54 and 55 respectively provide for the proximal end section 102 of stent 100 compressed to its final diameter by means of the supplementary compressing mechanism 10' to be kept in its compressed state by means of a further sleeve-shaped receiving area (second receiving area 121).

After the compressed proximal end section 102 of stent 100 is loaded for example into the second sleeve-shaped element 107 of the catheter tip 105, the supplementary compressing mechanism 10' is removed from the catheter tip 105 by manipulating the clamping jaws 11.1 to 11.6 of the supplementary compressing mechanism 10' such that the clamping jaws 11.1 to 11.6 move radially outward perpendicular to the longitudinal axis of the supplementary compressing mechanism 10'.

However, the present invention is not limited to a system of the kind as the exemplary embodiment depicted in FIGS. 11*a* to 11*c*. Rather, the system for loading a stent 100 into the catheter tip 105 of a medical delivery system may also a device 1 according the second, third, fourth or fifth exemplary embodiment as previously described when referencing the representations provided in FIGS. 12 to 53. Hence, a device 1 may be thus used to compress a stent 100, whereby the device 1 comprises a compressing mechanism 10 as well as a manipulating mechanism 40.

In particular, the system for loading a stent 100 or a stent 100 with a prosthetic heart valve affixed thereto into a medical delivery system, in particular a catheter tip 105 of a medical delivery system, may comprise a device 1 in accordance with any one of the previously described exemplary embodiments and a supplementary compressing mechanism for further compressing at least parts of the stent 100, wherein the supplementary compressing mechanism shall be configured analogously to the compressing mechanism 10 of the device according to the previously described exemplary embodiments.

An exemplary embodiment of a catheter tip 105-1 of a medical delivery system for transapically introducing an expanded stent into the body of a patient will be described below referencing FIG. 54. The system described above for example with reference to FIGS. 11a to 11c is suited to loading a stent 100 into the catheter tip 105-1 depicted in FIG. 54; although the disclosure is in no way limited to the use of the system in combination with the catheter tip 105-1 shown in FIG. 54. Rather, the following description only serves to present an example of the design of a catheter tip 105-1 of a medical delivery system designed for a transapical approach, whereby the system aids in loading a stent 100, as needed with a prosthetic heart valve affixed thereto, into said catheter tip 105-1.

The catheter tip 105-1 depicted in FIG. 54 is part of a medical delivery system (not further shown in FIG. 54) which is suited for a transapical approach to a heart valve to be treated, such as for example an aortic valve.

The medical delivery system enables an expandable heart valve stent to be implanted transapically in a patient's body; i.e. advanced from the apex of the heart. To this end, the delivery system comprises a catheter system (not shown in FIG. 43) by means of which the stent (likewise not depicted in FIG. 54) can be positioned in its folded state in the patient's body.

The catheter tip 105-1 shown in FIG. 54 is disposed at the proximal end section of the catheter system where the stent to be implanted in the patient's body can be accommodated. A handle (not shown in FIG. 54) can be provided at the distal end section of the catheter system with which the catheter tip 105-1 can be manipulated.

In detail, the catheter tip 105-1 of the medical delivery system designed for transapical approach comprises a stent holder 150 by means of which the distal end section 101 of a stent 100 to be implanted into the body of the patient can be releasably fixed to the catheter tip 105-1. The catheter tip 105-1 further comprises receiving means for receiving at least the proximal end section 102 of the stent 100. Specifically, the receiving means for the catheter tip 105-1 exemplarily depicted in FIG. 54 consists of a first receiving area 111 and a second receiving area 121.

As FIG. 54 indicates, the medical delivery system designed for a transapical approach provides for the first receiving area 111 of catheter tip 105-1 to be configured as a stent sheath connected to the proximal end tip 125 of catheter tip 105-1 with its opening pointing toward the distal end section 126 of catheter tip 105-1. The first receiving area 111 configured as a stent sheath forms the outer lateral surface of the catheter tip 105-1 when the latter—as shown in FIG. 54—is in its closed state.

In the catheter tip 105-1 of the delivery system designed for a transapical approach, the second receiving area 121 of catheter tip 105-1 is configured as a stent funnel with its opening pointing toward the proximal end tip 125 of catheter tip 105-1. The proximal end section 102 of a stent 100 to be implanted (not shown in FIG. 54) can for example be received within the second receiving area 121 configured as a stent funnel after the system has been used—as described above referencing FIGS. 11a to 11c—to compress the proximal end section 102 of stent 100 accordingly.

For example, it is conceivable for the proximal end section 102 of stent 100 to comprise retaining holders to which a prosthetic heart valve is affixed as needed. In such a case, the retaining holders of stent 100, and the prosthetic heart valve affixed as needed to the retaining holders, are accommodated within the second receiving area 121 of catheter tip 105-1 configured as a stent funnel.

In the closed state of catheter tip 105-1 (cf. FIG. 54), the second receiving area 121 configured as a stent funnel is telescopically received by the first receiving area 111 configured as a stent sheath, whereby positioning holders of the stent can for example be arranged between the outer lateral surface of the stent funnel and the inner lateral surface of the stent sheath when a corresponding heart valve stent is accommodated in the catheter tip 105-1.

In the catheter tip 105-1 of a medical delivery system designed for a transapical approach as depicted in FIG. 54, the second receiving area 121 of the catheter tip 105-1 is—as noted above—configured as a stent funnel in the form of a tubular or sleeve-like element. The stent funnel (second receiving area 121) can be connected to actuating means of a handle via a force transfer means (not explicitly shown in FIG. 54) so that pulling or pushing forces can be transferred to the second receiving area 121 of the catheter tip 105-1 upon the actuating of the actuating means. In this way, the second receiving area 121 of the catheter tip 105-1 configured as a stent funnel can be displaced in the longitudinal direction of the catheter tip 105-1 relative the stent holder 150 on the one hand and, on the other, the first receiving area 111 configured as a stent sheath.

As indicated above, it is preferred for the first receiving area 111 of the catheter tip 105-1 of the medical delivery system designed for a transapical approach to be configured as a stent sheath, for example in the form of an elongated tube. The second receiving area 121 is preferably configured as a stent funnel, likewise for example in the form of an elongated tube. The inner diameter of the tubular or sleeve-shaped first receiving area 111 should thereby be selected to be larger than the outer diameter of the likewise tubular or sleeve-shaped second receiving area 121 such that the second receiving area 121 can be telescopically received inside the first receiving area 111.

The stent holder 150 of the catheter tip 105-1 for a medical delivery system designed for a transapical approach as depicted in FIG. 54 is configured as a cylindrical element furnished with appropriate retaining elements 151. The retaining elements 151 serve to create a releasable connection to a retaining section of a heart valve stent 100 not shown in FIG. 54 when the stent 100 is accommodated in the catheter tip 105-1. Conceivable here would be to configure the retaining elements 151 of the stent holder 150 such that they can releasably engage with the retaining elements of stent 100.

In FIG. 54, the retaining elements 151 of stent holder 150 are for example configured as projecting elements which can be brought into engagement with retaining grommets of a stent 100 configured correspondingly complementary thereto. It would however also be conceivable for the retaining elements 151 of stent holder 150 to be configured as cavities or recesses introduced into the cylindrical body of the stent holder 150 and designed to receive correspondingly complementary configured retaining elements of the heart valve stent 100.

The procedure for loading a heart valve stent 100 into the example of the catheter tip 105-1 as depicted in FIG. 54 corresponds to the method described above with reference to the representations of FIGS. 11a to 11c. To avoid repetition, the loading procedure will not be reiterated in detail here; reference is instead made to the previous remarks.

With the catheter tip 105-1 for a medical delivery system designed for a transapical approach shown as an example in FIG. 54, the stent holder 150 is arranged to be stationary relative the (not shown) handle of the medical delivery system such that upon a rotation of the handle about the longitudinal axis of the medical delivery system, for example, the stent holder 150 will also be engaged in the rotational motion. It is hereby conceivable for the stent holder 150 to be connected to the handle via connecting means fixedly attached to the body of the handle.

On the other hand, the first receiving area 111 of the catheter tip 105-1 is also movable in the longitudinal direction of the catheter tip 105-1 relative the stent holder 150 by means of appropriately manipulating a force transfer means. With the catheter tip 105-1 shown for example in FIG. 54, an inner catheter 130 configured as a cannula tube extending from a distal end section of a handle (not shown in FIG. 54) to the proximal-side end tip 125 of the catheter tip 105-1 is employed as the force transfer means.

As indicated above, it is provided in the case of the catheter tip 105-1 for a medical delivery system designed for a transapical approach for the stent holder 150 of the catheter tip 105-1 to preferably be fixedly connected to a handle, a body of the handle respectively, so as to in particular freeze the freedom of rotational motion about the longitudinal axis of the medical delivery system respective the stent holder 150 as well as the freedom of motion in the direction of the longitudinal axis of the medical delivery system. Accordingly, the stent holder 150 is restricted from moving at least in the longitudinal direction of the medical delivery system relative the body of the handle. Rotational motion of the stent holder 150 about the longitudinal axis relative the handle is likewise eliminated.

It is to be emphasized that the system for loading a stent 100, as needed with a prosthetic heart valve 100 affixed thereto, into the tip of a catheter of a medical delivery system as disclosed above is not only applicable to a catheter tip 105-1 for a medical delivery system designed for a transapical approach. In fact, it is equally possible to also use the system to load a stent system into a catheter tip of a medical delivery system designed for a transfemoral/transarterial approach.

The following, referencing FIG. 55, will describe the design of an exemplary embodiment of a catheter tip 105-2 of a medical delivery system designed to transfemorally/transarterially introduce an expandable stent into the body of a patient. To be considered here is that the previously described example of a system referencing FIGS. 11a to 11c is also suited to load a stent 100 into the catheter tip 105-2 depicted in FIG. 55. The following description serves to present an example of a catheter tip 105-2 of a medical delivery system designed for a transfemoral/transarterial approach, whereby the system can be employed to load a stent, as needed with a prosthetic heart valve affixed thereto, into said catheter tip 105-2.

The catheter tip 105-2 depicted in FIG. 55 is part of a medical delivery system (not further shown) applicable for transfemorally/transarterially approaching a heart valve to be treated such as an aortic valve, for example. The medical delivery system enables an expandable heart valve stent to be implanted into the body of a patient transfemorally or transartially, i.e. from the aortic arch. To this end, the delivery system comprises a catheter system (not shown in FIG. 55), by means of which the heart valve stent (likewise not shown in FIG. 55) can be introduced into the body of the patient in its folded state.

The embodiment of the medical delivery system suited for a transarterial or transfemoral approach differs from the delivery system designed for transapical approach as described above referencing the FIG. 54 representation by the catheter tip 105-2 exhibiting a modified design to allow the transarterial approach to the site of implantation.

With regard to the design of the catheter tip 105-2 allowing the transarterial or transfemoral approach for the stent accommodated in the catheter tip 105-2 to the site of implantation, it can be seen from FIG. 55 that the catheter tip 105-2—just like the catheter tip 105-1 of the delivery system designed for a transapical approach—comprises a stent holder 150 for releasably fixing for example the distal end section 101 of a stent 100 which can be accommodated in the catheter tip 105-2. Compared to the catheter tip 105-1 for the delivery system designed for a transapical approach, the retaining elements 151 of the stent holder 150 configured as a crown are here provided at the distal end of the stent holder 150.

Furthermore, the catheter tip 105-2 of the delivery system designed for a transarterial/transfemoral approach comprises receiving means to receive a heart valve stent with the prosthetic heart valve affixed thereto as needed. Specifically, the receiving means of the catheter tip 105-2 consists of a first receiving area 111 to receive the distal end section 101 of a stent 100, in particular the positioning holder of a stent, and a second receiving area 121 to receive the proximal end section 102 of the stent 100, in particular the retaining holder of the stent with the prosthetic heart valve affixed thereto as needed.

As distinguished from the catheter tip 105-1 of the medical delivery system designed for a transapical approach as described with reference to FIG. 54, in the catheter tip 105-2 of the medical delivery system designed for a transarterial/transfemoral approach pursuant FIG. 55, the second receiving area 121 (stent funnel) serving to receive the proximal end section 102 of the stent 100, and in particular the retaining holder of the stent with the prosthetic heart valve affixed as needed thereto, is arranged on the proximal end section 125 of the catheter tip 105-2 while the first receiving area 111 (stent sleeve) is arranged between the second receiving area 121 and a handle (not shown in FIG. 55).

In the catheter tip 105-2 of the medical delivery system as depicted in FIG. 55 designed for the transarterial approach to an insufficient or stenosed native heart valve, it is preferable to configure force transfer means, which connect actuating means of the handle to the second receiving area 121 (stent funnel) of the catheter tip 105-2, as an inner catheter 131 extending through the interior of an outer catheter or a sheath system. A further force transfer means which connects further actuating means of the handle to the first receiving area 111 (stent sleeve) of the catheter tip 105-2, is configured as an outer catheter, through the interior of which runs the other force transfer means configured as the inner catheter.

Upon the actuating of the associated actuating means, the second receiving area 121 (stent funnel) is movable in the longitudinal direction of the catheter tip 105-2 relative the stent holder 150 in the proximal direction; i.e. away from the (not shown) handle, while the first receiving area 111 of catheter tip 105-2 is movable, upon the actuating of the correspondingly associated actuating means of the handle, in the longitudinal direction of the catheter tip 105-2 relative stent holder 150 in the distal direction; i.e. toward the handle not shown in FIG. 55.

The manipulations of the respective receiving areas 111, 121 of the catheter tip 105-2 of the delivery system designed for a transarterial/transfemoral approach effected by the actuating of the respective actuating means enables a sequential release of a stent 100 accommodated in the catheter tip 105-2, preferably at the site of implantation in the patient's heart.

The procedure for loading a heart valve stent 100 into the catheter tip 105-2 depicted as an example in FIG. 55 corresponds to the following method described hereinafter:

For loading a stent 100 or a stent 100 with a prosthetic heart valve affixed thereto into a medical delivery system, in particular into a catheter tip 105 of a medical delivery system, the method shall comprises the following method steps:

i) furnishing a device (1) in accordance with any one of the previously described second third and fourth exemplary embodiments of the present invention or a system in accordance with the present invention;

i) inserting a stent 100 or a stent 100 with a prosthetic heart valve affixed thereto into the compressing mechanism 10 of the device 1 such that the stent 100 is at least partly accommodated in the compressing mechanism 10 of the device;

iii) moving the manipulating mechanism 40 of the device 1 relative to the compressing mechanism 10 thereby moving the at least one clamping means 50, 70.1 to 70.n, 90.1 to 90.n of the compressing mechanism 10 in the radial direction for adjusting the internal cross-sectional diameter of the compressing mechanism 10 such that at least parts of the stent 100, in particular parts of the upper end section of the stent 100, are at least partly compressed; and iv) inserting the at least partly compressed stent 100 into a first sleeve-shaped element 106 of the catheter tip 105.1 or 105.2 of the medical delivery system.

Prior to the inserting at least partly compressed stent 100 into a first sleeve-shaped element 106 of the catheter tip 105.1 or 105.2, it is conceivable to further reduce the cross-sectional diameter of the stent 100. For this purpose, a compressing mechanism 10 as described in conjunction with one of the second, third or fourth exemplary embodiments may be used.

In particular, the operator may insert the at least partly compressed stent 10 into a supplementary compressing mechanism of a compressing device which is configured analogously to the device 1 in accordance with any of the second, third or fourth exemplary embodiments of the device as described above. Thereafter, the operator shall move the manipulating mechanism of the supplementary compressing device relative to the compressing mechanism of the supplementary compressing device in order to move the at least one clamping means of the supplementary compressing device in the radial direction for adjusting the internal cross-sectional diameter of the compressing mechanism of the supplementary compressing device and for at least partly further compressing the stent 100 by exerting a compressive force in radial direction on at least parts of the stent 100 accommodated in the compressing mechanism 10 of the supplementary compressing device.

Furthermore, it is conceivable to force the at least party compressed stent 100 such as that the at least party compressed stent 100 passes through a cone 83 thereby further reducing the cross-sectional diameter of the stent 100. For example, the at least partly compressed stent 100 may be pushed through the cone 83 by using a push rod 2a, 2b.

In order to be able to load a stent 100 into the catheter tip 105-2 of a medical delivery system designed for a transfemoral/transarterial approach, however, it is conceivable to insert the catheter tip 105 of the medical delivery system through the compressing mechanism 10, within which the already precompressed stent 100 is accommodated. The distal end section 101 of the stent 100 can then be further compressed and brought into engagement with the stent holder 150 of the catheter tip 105-2. The compressing mechanism 10 can thereafter be removed from the catheter tip 105-2 of the medical delivery system. However, the disclosed solution is not limited to a specific type of stent or a specific type of catheter tip. Rather, the disclosed device is also applicable for stents different from the stents as described herein. In particular, the disclosed device may also be used for compressing a stent where the top of the stent is not compressed first.

In summary, it remains to be noted that the above disclosure transforms a stent, as needed with a prosthetic heart valve affixed thereto, from its expanded state into a compressed state in particularly smooth manner. The above disclosure is not only suited to compressing stents, but also grasping a stent in the catheter tip of a transapical or transfemoral medical delivery system. The degree of compression is adjustable at will.

The disclosed solution is not limited to the embodiments described with reference to the accompanying drawings. Also just as conceivable in fact are combinations of the individual features as specifically described.

LIST OF REFERENCE NUMERALS

| List of reference numerals | |
|---|---|
| 1, 1a to 1d | compressing device |
| 2a, 2b | push rod |
| 3 | gripper-like mechanism |
| 4 | first gripper arm |
| 5 | second gripper arm |
| 6 | bolt |
| 7.1, 7.2 | mounting part |
| 8 | bolt |
| 9 | hole |
| 10, 10a to 10d | compressing mechanism |
| 11.1 to 11.6 | clamping jaw |
| 12 | guiding element |
| 13 | funnel-shaped area |
| 14 | clamping area |
| 15, 15.1 to 15.6 | contact surface |
| 16.1 to 16.6 | grooved guide |
| 17.1 to 17.6 | guiding surface |
| 18.1 to 18.6 | guiding web |
| 19.1 to 19.6 | stop |
| 20 | gripping mechanism |
| 21 | actuating element |
| 22 | claw |
| 23 | guiding sleeve |
| 25 | retaining section |
| 26 | pushbutton |
| 27.1 to 27.3 | gripper arm |
| 28.1 to 28.3 | fastening means |
| 29 | guiding shaft |
| 29a | first end of guiding shaft |
| 29b | second end of guiding shaft |
| 30 | guide means |
| 31 | helical compression spring |
| 32 | underface of retaining section |
| 33 | connecting area |
| 40, 40a to 40d | manipulating mechanism |
| 41 | dedicated groove |
| 42 | manipulating part |
| 43 | guiding surface |
| 50 | strip/flat strip |
| 51 | first end section of strip |
| 52 | second end section of strip |
| 53 | slit in first end section of strip |
| 54 | housing part |
| 55 | first slit-like opening |
| 56 | second slit-like opening |
| 57 | body of manipulating mechanism |
| 58 | plain cover |
| 59 | engagement means |
| 60 | complementary engagement means |
| 61 | center opening of plain cover |
| 62 | cutout |
| 63 | protruding segment |
| 64 | latching means |

-continued

| List of reference numerals | |
|---|---|
| 65 | window area |
| 66 | complementary engagement means |
| 70.1 to 70.n | clamping jaw |
| 71 | wedge surface |
| 72 | opposite surface |
| 73 | protruding part |
| 74 | head portion |
| 75 | housing part |
| 76 | guiding slit |
| 77 | first housing section |
| 78 | second housing section |
| 79 | third housing section |
| 80 | rail element |
| 81 | main surface of rail element |
| 82 | guiding surface of rail element |
| 83 | cone |
| 84 | manipulating part |
| 85 | dedicated groove of manipulating part |
| 86 | push rod lead-through |
| 90.1 to 90.n | clamping jaw |
| 91 | wedge surface |
| 92 | flange surface of clamping jaw |
| 93 | front surface of clamping jaw |
| 94 | protruding part of clamping jaw |
| 95 | stop member of clamping jaw |
| 96 | housing part |
| 97 | guiding slit |
| 98 | disk-like part of housing part |
| 99 | ring-shaped part of housing part |
| 100 | stent |
| 101 | upper end section of stent |
| 102 | lower end section of stent |
| 105.1, 105.2 | catheter tip |
| 106 | first sleeve shaped element |
| 107 | second sleeve shaped element |
| 110.1 to 110.n | clamping jaw |
| 111 | wedge surface of clamping jaw |
| 112 | opposite surface of clamping jaw |
| 113 | protruding part of clamping jaw |
| 114 | head portion of clamping jaw |
| 115 | housing part |
| 116 | guiding slit |
| 117 | first housing section |
| 118 | second housing section |
| 119 | guiding surface |
| 120 | cone |
| 121 | manipulating part |
| 122 | groove |
| 123 | securing means/teeth like element |
| 124 | lead through |
| 125 | dedicated slit |
| 126 | bolt like part |
| 127 | spring |
| 128 | locking disk |
| 130.1 to 130.n | radial arms of part 84 |
| 131.1 to 131.m | radial arms of part 121 |
| 150 | stent holder |
| L | longitudinal direction of device |
| L' | longitudinal direction of compressing mechanism |
| L" | longitudinal direction of manipulating part |
| α | angle between wedge surface and opposite surface of clamping jaw |

The invention claimed is:

1. A device for compressing a stent, comprising:
a compressing mechanism configured to at least partially accommodate a stent, the compressing mechanism including
at least one clamping element configured to selectively exert a compressive force in a radial direction on the stent to reduce the cross-sectional dimension of at least a portion of the stent; and
a housing including a first housing section and a second housing section, wherein an inner circumferential surface of the first housing section includes a plurality of slits, the inner circumferential surface of the first housing being tapered towards the second housing section; and
a manipulating mechanism configured to manipulate the at least one clamping element, the manipulating mechanism being moveable relative to the compressing mechanism for affecting movement of the at least one clamping element in the radial direction.

2. The device according to claim 1, wherein the at least one clamping element includes a plurality of jaws circumferentially arranged such that respective radial inward surfaces of the jaws define a cavity at least partially surrounding the stent.

3. The device according to claim 2, wherein the jaws are mounted in the housing and configured to be moveable in a longitudinal direction of the compressing mechanism relative to the housing.

4. The device according to claim 3, wherein each slit extends in the longitudinal direction of the compressing mechanism, wherein each of the plurality of slits interacts with one of the plurality of jaws to guide a respective jaw during at least a portion of the movement of the jaw in the longitudinal direction of the compressing mechanism relative to the housing.

5. The device according to claim 4, wherein each of the plurality of jaws further includes at least one head portion disposed on a radial outward surface of the jaw opposite the radial inward surface, each head portion configured to be engaged with a respective one of the plurality of slits.

6. The device according to claim 4, wherein the inner circumferential surface of the first housing section is inclined at a first angle relative to the longitudinal direction of the compressing mechanism that is substantially the same as a second angle formed between a radial inward surface and a radial outward surface of one of the plurality of jaws.

7. The device according to claim 6, wherein an inner circumferential surface of the second housing section is inclined at a third angle that is substantially the same as the second angle.

8. The device according to claim 6, wherein the second housing section includes a plurality of rail elements disposed on an inner circumferential surface of the second housing, each rail element having an inner surface connected to the inner circumferential surface of the second housing section and an outer surface opposite to the inner surface configured to selectively engage the jaw when the jaw is moved in the longitudinal direction of the compressing mechanism relative to the housing.

9. The device according to claim 8, wherein the outer surface of each of the plurality of rail elements is inclined at a fourth angle relative to the inner circumferential surface of the second housing, the fourth angle being substantially the same as the second angle.

10. The device according to claim 1, wherein the housing further includes a third housing section disposed on a longitudinal side of the second housing section opposite the first housing section, the third housing section including a cone.

11. The device according to claim 3, wherein the manipulating mechanism interacts with the plurality of jaws such that, by moving the manipulating mechanism in the longitudinal direction relative to the housing, the plurality of jaws are moved in both the longitudinal and radial directions relative to the housing thereby reducing the cross-sectional diameter of at least a portion of the stent accommodated within the cavity defined by the plurality of jaws.

12. The device according to claim 3, wherein the manipulating mechanism includes a cup-shape and is configured to at least partially surround the housing in a releasable manner, and wherein each of the plurality of jaws includes at least one head portion disposed on a sliding surface of the clamping jaw opposite to the radial inward surface, each head portion protruding from the outer circumferential surface of the housing.

13. The device according to claim 1, wherein the compressing mechanism and the manipulating mechanism each includes a reduced diameter portion, wherein the reduced diameter portion of the compressing mechanism is axially aligned with the reduced diameter portion of the manipulating mechanism to permit a push rod to pass through the device.

14. The device according to claim 13, wherein the reduced diameter portion of the compressing mechanism is disposed at a first axial end of the device and the reduced diameter portion of the manipulating mechanism is disposed at a second axial end of the device.

15. The device according to claim 1, further comprising a stent accommodated within the compressing mechanism.

16. The device according to claim 15, wherein a prosthetic valve is connected to the stent.

17. The device according to claim 1, wherein the manipulating mechanism further includes at least one arm extending radially inward relative to an inner circumferential surface of the manipulating mechanism, the at least one arm circumferentially aligned with the at least one clamping element.

18. The device according to claim 2, wherein the manipulating mechanism further includes a plurality of arms extending radially inward relative to an inner circumferential surface of the manipulating mechanism, wherein each of the plurality of arms is circumferentially aligned with a respective one of the plurality of jaws.

19. A device for compressing a stent, comprising:
a compressing mechanism configured to at least partially accommodate a stent, the compressing mechanism including at least one clamping element configured to selectively exert a compressive force in a radial direction on the stent to reduce the cross-sectional dimension of at least a portion of the stent, the at least one clamping element including a plurality of jaws circumferentially arranged such that respective radial inward surfaces of the jaws define a cavity at least partially surrounding the stent; and
a manipulating mechanism configured to manipulate the at least one clamping element, the manipulating mechanism being moveable relative to the compressing mechanism for affecting movement of the at least one clamping element in the radial direction, wherein an inner surface of the manipulating mechanism includes a plurality of grooves, each groove extending in a longitudinal direction of the manipulating mechanism and configured to receive a respective head portion of one of the jaws.

20. A device for compressing a stent, comprising:
a compressing mechanism having a longitudinal axis, a housing, and a plurality of jaws;
a plurality of slits disposed in a first section of the housing, the plurality of slits being arranged circumferentially about the longitudinal axis of the compressing mechanism, the plurality of jaws respectively disposed within the plurality of slits;
a plurality of rails disposed in a second section of the housing, the plurality of rails being arranged circumferentially about the longitudinal axis of the compressing mechanism; and
a manipulating mechanism at least partially surrounding the housing and engaging the plurality of jaws;
wherein the manipulating mechanism is configured to move longitudinally relative to the housing and affect longitudinal movement of the plurality of jaws from the first section of the housing to the second section of the housing; and
wherein the plurality of jaws are configured to respectively engage the plurality of rails during movement from the first section of the housing to the second section of the housing and move radially inward toward the longitudinal axis of the compressing mechanism thereby reducing the cross sectional size of at least a portion of a stent accommodated radially within the plurality of jaws.

* * * * *